United States Patent
Zhang

(10) Patent No.: US 6,653,485 B2
(45) Date of Patent: Nov. 25, 2003

(54) ORTHO SUBSTITUTED CHIRAL PHOSPHINES AND PHOSPHINITES AND THEIR USE IN ASYMMETRIC CATALYTIC REACTIONS

(75) Inventor: Xumu Zhang, State College, PA (US)

(73) Assignee: The Penn State Research Foundation, University Park, PA (US)

(*) Notice: Subject to any disclaimer, the term of this patent is extended or adjusted under 35 U.S.C. 154(b) by 0 days.

(21) Appl. No.: 09/991,261

(22) Filed: Nov. 16, 2001

(65) Prior Publication Data

US 2002/0128501 A1 Sep. 12, 2002

Related U.S. Application Data

(60) Provisional application No. 60/301,221, filed on Jun. 27, 2001, and provisional application No. 60/249,537, filed on Nov. 17, 2000.

(51) Int. Cl.[7] .................................................. C07F 9/50
(52) U.S. Cl. ........................... 549/221; 568/17; 568/12; 568/13; 548/112; 546/22; 544/542; 556/13
(58) Field of Search ............................... 568/13, 16, 17; 549/5, 6, 7, 9, 10, 11, 13, 14, 20, 216, 218, 221; 548/956, 112; 546/22; 544/542

(56) References Cited

U.S. PATENT DOCUMENTS

| | | | | |
|---|---|---|---|---|
| 5,312,996 A | * | 5/1994 | Packett | 568/454 |
| 5,710,339 A | * | 1/1998 | Laue et al. | 568/16 |
| 5,728,886 A | * | 3/1998 | Naumann et al. | 568/17 |
| 5,847,222 A | * | 12/1998 | Yokozawa et al. | 568/16 |
| 5,872,273 A | * | 2/1999 | Saito et al. | 556/21 |
| 5,972,825 A | * | 10/1999 | Regnat et al. | 502/164 |
| 6,162,951 A | * | 12/2000 | Polywka et al. | 568/13 |
| 6,333,291 B1 | * | 12/2001 | Yokozawa et al. | 502/162 |

FOREIGN PATENT DOCUMENTS

| WO | WO 92/16536 | 10/1992 | ........... C07F/9/655 |
|---|---|---|---|
| WO | WO 93/15089 | 8/1993 | ............. C07F/9/50 |

OTHER PUBLICATIONS

CA:134:326631 abs of EP 1095946 May 2001.*
Simonsen et al., "A simple synthetic approach to 3,3'–diaryl BINOLs." *J. Org. Chem.* 1998, 63, 7536–7538.
Xiao et al. "Synthesis of a novel chiral binaphthyl phospholane and its application in the highly enantioselective dydrogenation of enamides." *Organic Letters.* 1999, vol. 1, No. 10, 1679–1681.
Zhu et al. "Highly efficient asymmetric synthesis of β–amino acid derivatives via rhodium–catalyzed hydrogenation of β–(acylamino)acrylates." *J. Org. Chem.* 1999, 64, 6907–6910.
Tschaen et al. "Asymmetric synthesis of MK–0499." *J. Org. Chem.* 1995, 60, 4324–4330.
Lubell et al. "Enantioselevtive synthesis of β–amino acids based on BINAP–ruthenium (II) catalyzed hydrogenation." *Tetrahedron Asymmetry.* vol. 2, No. 7, 543–554, 1991.
Tamao et al. "Optically active 2,2'–bis(diphenylphosphinomethyl)–1,1'–binaphthyl: A new chiral bidentate phosphine Ligand for transition–metal complex catalyzed asymmetric reactions." *Tetrahedron Letters.* No. 16, 1389–1392, 1977.
Zhang et al. "Asymmetric synthesis of chiral amine derivatives through enantioselective hydrogenation with a highly effective rhodium catalyst containing a chiral bisaminophosphine ligand." *J. Am. Chem. Soc.,* 1998, 120, 5808–5809.
Cox et al. "Expedient route to 3– and 3,3'–substituted 1,1'–Bi–2–naphthols by directed ortho metalation and suzuki cross coupling methods." *Tetrahedron Letters.* vol. 33, No. 17, 2253–2256, 1992.
Grubbs et al. "Asymmetric hydrogentaion by an atropisomeric diphosphinite rhodium complex." *Tetrahedron Letters.* No. 22, 1879–1880, 1977.
Schmid et al. "New developments in enantioselective hydrogenation." *Pure & Appl. Chem.* vol. 68, No. 1, 131–138, 1996.
Noyori et al., "BINAP: An efficient chiral elemant for asymmetric catalysis." *Acc. Chem. Res.,* 1990, 23, 345–350.
Ohkuma et al. "Asymmetric hydrogenation of Alkenyl, Cyclopropyl, and Aryl Ketones. $RuCl_2$(xylbinap) (1,2–diamine) as a precatalyst exhibiting a wide scope." *J. Am. Chem. Soc.* 1998, 120, 13529–13530.
Zhang et al. "Highly enantioselective hydrogenation of α, β–unsaturated carboxylic acids catalyzed by $H_8$_BINAP–Ru(II) complexes." *Synlett.* Jul. 1994, 501–503.
Schmid et al. "Axially dissymmetric bis(triaryl)phosphines in the biphenyl series: Synthesis of(6,6'–dimethylbiphenyl–2,2'–diyl)bis(diphenylphosphine)('BIPHEMP') and analogues, and their use in Rh(I)–catalyzed asymmetric isomerizations of N,N–Diethylnerylamine." *Helvetica Chmica Acta.* vol. 71 (1998) 897–929.
CA:136:37900. Sirges, W. et al. "Method for the Preparation of optically active trimethylactic acid and its esters." EP1160237, Dec. 5, 2001.
CA:133:30992. Zhang et tal. "Synthesis of Chiral Bisphosphines with Tunable Bite Angles and Their Applications in Asymmetric Hydrogenation of .beta.–Ketoesters."

* cited by examiner

Primary Examiner—Jean F. Vollano
(74) Attorney, Agent, or Firm—Ohlandt, Greeley, Ruggiero & Perle, L.L.P

(57) ABSTRACT

3,3'-Substituted chiral biaryl phosphine and phosphinite ligands and metal complexes based on such chiral ligands useful in asymmetric catalysis are disclosed. The metal complexes are useful as catalysts in asymmetric reactions, such as, hydrogenation, hydride transfer, allylic alkylation, hydrosilylation, hydroboration, hydrovinylation, hydroformylation, olefin metathesis, hydrocarboxylation, isomerization, cyclopropanation, Diels-Alder reaction, Heck reaction, isomerization, Aldol reaction, Michael addition, epoxidation, kinetic resolution and [m+n] cycloaddition. The metal complexes are particularly effective in Ru-catalyzed asymmetric hydrogenation of beta-ketoesters to beta-hydroxyesters and Ru-catalyzed asymmetric hydrogenation of enamides to beta amino acids.

17 Claims, No Drawings

ORTHO SUBSTITUTED CHIRAL PHOSPHINES AND PHOSPHINITES AND THEIR USE IN ASYMMETRIC CATALYTIC REACTIONS

This application claims priority from U.S. Provisional Application Serial No. 60/249,537, filed Nov. 17, 2000, and U.S. Provisional Application Serial No. 60/301221, filed Jun. 27, 2001.

BACKGROUND OF THE INVENTION

1. Field of the Invention

The present invention relates to novel chiral ligands derived from 3,3'-substituted biaryl phosphines and phosphinites. More particularly, the present invention relates to transition metal complexes of these chiral phosphine ligands. The transition metal complexes are useful as catalysts in asymmetric reactions, such as, hydrogenation, hydride transfer, allylic alkylation, hydrosilylation, hydroboration, hydrovinylation, hydroformylation, olefin metathesis, hydrocarboxylation, isomerization, cyclopropanation, Diels-Alder reaction, Heck reaction, isomerization, Aldol reaction, Michael addition, epoxidation, kinetic resolution and [m+n] cycloaddition.

2. Description of the Prior Art

Discovery of new chiral ligands is crucial in developing highly enantioselective transition metal-catalyzed reactions. Many chiral ligands have been made for applications in asymmetric catalysis, however, relatively few of these chiral ligands are commonly used in industry for the synthesis of chiral molecules.

Several chiral ligands having a biaryl backbone are known in the prior art. These are summarized below:

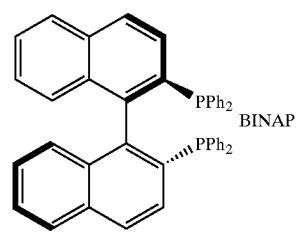

(1) BINAP

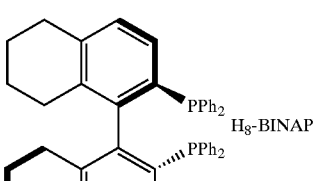

(2) H8-BINAP

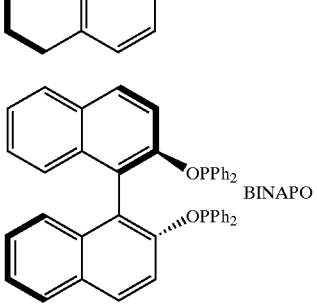

(3) BINAPO

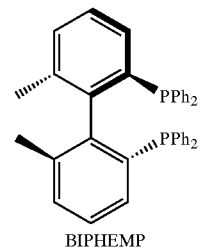

(4) BIPHEMP

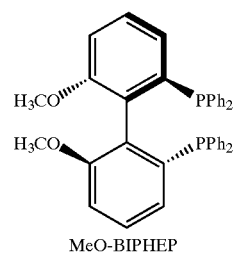

(5) MeO-BIPHEP

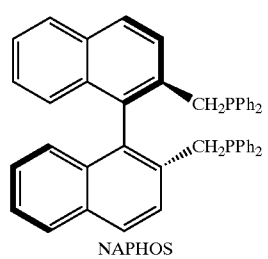

(6) NAPHOS

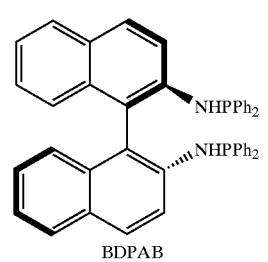

(7) BDPAB

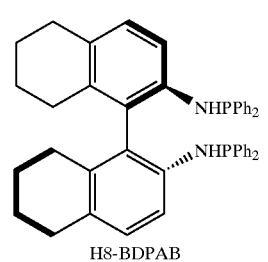

(8) H8-BDPAB

Among these ligands, BINAP (1) is one of the most frequently used chiral ligands. The axially dissymmetric, fully aromatic BINAP has demonstrated to be highly effective for many asymmetric reactions (Noyori, R. et al. *Acc. Chem. Res.* 1990, 23, 345, Ohkuma, T. et al. *J. Am. Chem. Soc.* 1998, 120, 13529). Recent results show that partially hydrogenated BINAP with a larger bite angle, H8-BINAP (2), is a better ligand for certain asymmetric reactions due to restriction of conformational flexibility (Zhang X. et al. *Synlett* 1994, 501). Chiral BINAPO (3) was made and it was not effective due to the conformational flexibility (Grubbs, R. et al. *Tetrahedron Lett.* 1977, 1879). Other axially dissymmetric ligands such as BIPHEMP (4) and MeO-BIPHEP (5) were developed and used for a number of asymmetric reactions (Schmid, R. et al. *Pure & Appl. Chem.* 1996, 68, 131; Schmide, R. et al. *Helv. Chim. Acta,* 1988, 71, 897). However, the present inventor is not aware of any examples of related 3,3' substituted chiral biaryl phosphines, the subject of the present invention, being disclosed in the prior art (Broger, E. A. et al., WO 92/16536 and Broger, E. A. et al., WO93/15089). NAPHOS (6), another example of a prior art compound has been prepared (Tamao, K. et al. *Tetrahedron Lett.* 1977, 1389) and was found to be not effective for asymmetric hydrogenation reaction. The corresponding ligands with the N linker, BDPAB (7) and H8-BDPAB (8) have also been made and tested for asymmetric hydrogenation reactions (Zhang, F. et al. *J. Am. Chem. Soc.* 1998, 120, 5808).

SUMMARY OF THE INVENTION

The present invention includes a ligand represented by the formula or its enantiomer:

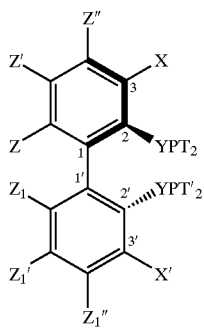

wherein each X and X' is independently selected from the group consisting of: alkyl, aryl, substituted alkyl, substituted aryl, OR, SR, $NR_2$, COOR, halide, $SiR_3$, $P(O)R_2$, $P(O)(OR)_2$ and $P(OR)_2$;

wherein each Z and $Z_1$ is independently selected from the group consisting of: alkyl, aryl, substituted alkyl, substituted aryl, OR, SR, $NR_2$, COOR, halide, $SiR_3$, $P(O)R_2$, $P(O)(OR)_2$ and $P(OR)_2$; or wherein Z and $Z_1$ together form the bridging group A-B-$A_1$;

wherein each Z', Z'', $Z_1$' and $Z_1$'' is independently selected from the group consisting of: H, alkyl, aryl, substituted alkyl, substituted aryl, OR, SR, $NR_2$, COOR, halide, $SiR_3$, $P(O)R_2$, $P(O)(OR)_2$ and $P(OR)_2$, or wherein Z' and Z together form the bridging group A'-B-A; Z' and Z together form a fused cycloaliphatic or aromatic group; $Z_1$ and $Z_1$' together form the bridging group $A_1$-$B_1$-$A_1$'; and/or $Z_1$ and $Z_1$' together form a fused cycloaliphatic or aromatic group;

wherein each A, A', $A_1$ and $A_1$' is independently selected from the group consisting of: O, $CH_2$, NH, NR, S, CO and a bond;

wherein each B and $B_1$ is independently selected from the group consisting of: linear, branched or cyclic alkylene of 1 to 6 carbon atoms, arylene of 6 to 12 carbon atoms, O, $CH_2$, NH, NR, S, CO, $SO_2$, P(O)R, P(O)OR, POR, $SiR_2$ and a bond;

wherein each T is independently selected from the group consisting of: alkyl, substituted alkyl, aryl, substituted aryl, alkoxide, aryloxide, R, R', R'', YR', YR'', Y'R' and Y''R''; or wherein two T groups together form an alkylene, arylene, alkylenediamino, arylenediamino, alkelenedioxyl or arylenedioxyl;

wherein each T' is independently selected from the group consisting of: alkyl, substituted alkyl, aryl, substituted aryl, alkoxide, aryloxide, R, R', R'', YR', YR'', Y'R' and Y''R''; or wherein two T' groups together form an alkylene, arylene, alkylenediamino, arylenediamino, alkelenedioxyl or arylenedioxyl;

wherein each R, R' and R'' is independently selected from the group consisting of: alkyl, substituted alkyl, aryl, aralkyl and alkaryl of 1 to 22 carbon atoms; or wherein two R groups, two R' groups or two R'' group together form an alkylene or arelene group; and wherein each Y, Y' and Y'' is independently selected from the group consisting of: O, $CH_2$, NH, S and a bond between carbon and phosphorus; with the proviso that when the Y group at the 2' position is a bond between carbon and phosphorus, X' is hydrogen.

The present invention further includes a catalyst prepared by a process, which includes: contacting a transition metal salt, or a complex thereof, and a ligand according to the present invention.

The present invention still further includes a process for preparation of an asymmetric compound including: contacting a substrate capable of forming an asymmetric product by an asymmetric reaction and a catalyst prepared by a process including: contacting a transition metal salt, or a complex thereof, and a ligand according to the present invention.

The metal complexes are useful as catalysts in asymmetric reactions, such as, hydrogenation, hydride transfer, allylic alkylation, hydrosilylation, hydroboration, hydrovinylation, hydroformylation, olefin metathesis, hydrocarboxylation, isomerization, cyclopropanation, Diels-Alder reaction, Heck reaction, isomerization, Aldol reaction, Michael addition, epoxidation, kinetic resolution and [m+n] cycloaddition. The metal complexes are particularly effective in Ru-catalyzed asymmetric hydrogenation of beta-ketoesters to beta-hydroxyesters and Ru-catalyzed asymmetric hydrogenation of enamides to beta amino acids.

DETAILED DESCRIPTION OF THE INVENTION

The present invention includes 3,3'-substituted chiral biaryl phosphines and phosphinites and related ligands for applications in asymmetric catalysis. Introduction of 3,3'-substituted groups can restrict the rotation of substituents adjacent to the phosphines. Control of orientations of these groups around the phosphine can lead to effective chiral induction for asymmetric reactions. Metal complexes of these phosphines, phosphinites and related non-$C_2$ symmetric ligands with ortho substitution are useful for a large variety of asymmetric reactions. A number of chiral ligands can be made having the desired structure in which the 3,3' positions are substituted, with the proviso that at least one ortho position is occupied by a group other than H atom.

In the non-$C_2$ symmetric ligands, ortho substituted groups play an important role for asymmetric catalysis. The 3,3' substituted chiral biaryl phosphines, phosphinites and related ligands of the present invention are described below. An important feature of these ligands is that at least one of the 3 and 3' positions must be occupied by a group other than hydrogen.

The ligands are represented by the formula:

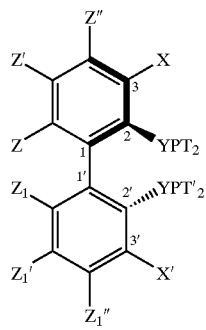

wherein each X and X' is independently selected from the group consisting of: alkyl, aryl, substituted alkyl, substituted aryl, OR, SR, $NR_2$, COOR, halide, $SiR_3$, $P(O)R_2$, $P(O)(OR)_2$ and $P(OR)_2$;

wherein each Z and $Z_1$ is independently selected from the group consisting of: alkyl, aryl, substituted alkyl, substituted aryl, OR, SR, $NR_2$, COOR, halide, $SiR_3$, $P(O)R_2$, $P(O)(OR)_2$ and $P(OR)_2$; or wherein Z and $Z_1$ together form the bridging group A-B-$A_1$;

wherein each Z', Z", $Z_1$' and $Z_1$" is independently selected from the group consisting of: H, alkyl, aryl, substituted alkyl, substituted aryl, OR, SR, $NR_2$, COOR, halide, $SiR_3$, $P(O)R_2$, $P(O)(OR)_2$ and $P(OR)_2$ or wherein Z' and Z together form the bridging group A'-B-A; Z' and Z together form a fused cycloaliphatic or aromatic group; $Z_1$ and $Z_1$' together form the bridging group $A_1$-$B_1$-$A_1$'; and/or $Z_1$ and $Z_1$' together form a fused cycloaliphatic or aromatic group;

wherein each A, A', $A_1$ and $A_1$' is independently selected from the group consisting of: O, $CH_2$, NH, NR, S, CO and a bond;

wherein each B and $B_1$ is independently selected from the group consisting of: linear, branched or cyclic alkylene of 1 to 6 carbon atoms, arylene of 6 to 12 carbon atoms, O, $CH_2$, NH, NR, S, CO, $SO_2$, P(O)R, P(O)OR, POR, $SiR_2$ and a bond;

wherein each T is independently selected from the group consisting of: alkyl, substituted alkyl, aryl, substituted aryl, alkoxide, aryloxide, R, R', R", YR', YR", Y'R' and Y"R"; or wherein two T groups together form an alkylene, arylene, alkylenediamino, arylenediamino, alkelenedioxyl or arylenedioxyl;

wherein each T' is independently selected from the group consisting of: alkyl, substituted alkyl, aryl, substituted aryl, alkoxide, aryloxide, R, R', R", YR', YR", Y'R' and Y"R"; or wherein two T groups together form an alkylene, arylene, alkylenediamino, arylenediamino, alkelenedioxyl or arylenedioxyl;

wherein each R, R' and R" is independently selected from the group consisting of: alkyl, substituted alkyl, aryl, aralkyl and alkaryl of 1 to 22 carbon atoms; or wherein two R groups, two R' groups or two R" group together form an alkylene or arelene group; and wherein each Y, Y' and Y" is independently selected from the group consisting of: O, $CH_2$, NH, S and a bond between carbon and phosphorus; with the proviso that when the Y group at the 2' position is a bond between carbon and phosphorus, X' is hydrogen. Preferably the alkylene group includes compounds represented by the formula: —$(CH_2)_n$—, wherein n is an integer in the range of from 1 to 8. The present invention also includes the corresponding enantiomer of each of the above ligands.

The substituted alkyl group can have one or more substituents and each substituent can independently be halogen, ester, ketone, carboxylic acid, hydroxy, alkoxy, aryloxy, thiol, alkylthio or dialkylamino. The aryl groups can optionally have one or more substituents, each of which can independently be halogen, ester, ketone, sulfonate, phosphonate, hydroxy, alkoxy, aryloxy, thiol, alkylthiol, nitro, amino, vinyl, substituted vinyl, carboxylic acid, sulfonic acid or phosphine. The arylene groups optionally can have one or more substituents, each of which can independently be halogen, ester, ketone, sulfonate, phosphonate, hydroxy, alkoxy, aryloxy, thiol, alkylthiol, nitro, amino, vinyl, substituted vinyl, carboxylic acid, sulfonic acid or phosphine. Preferably, each of the arylene groups can be 1,2-divalent phenyl, 2,2'-divalent-1,1'-biphenyl, 2,2'-divalent-1,1'-binaphthyl or ferrocene, i.e., a —Fc— group.

In a preferred embodiment, the present invention includes compounds represented by the following formulas:

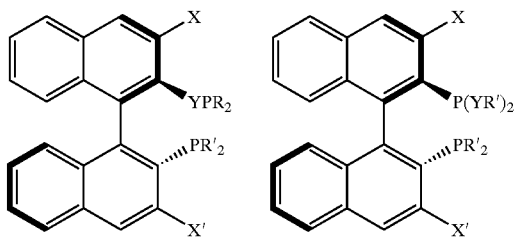

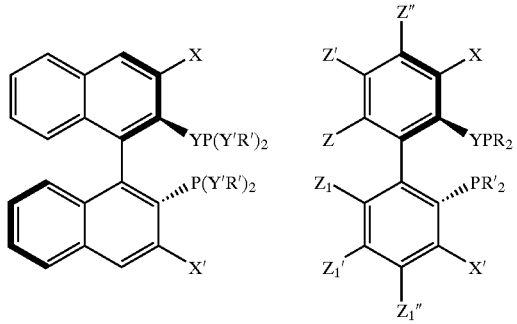

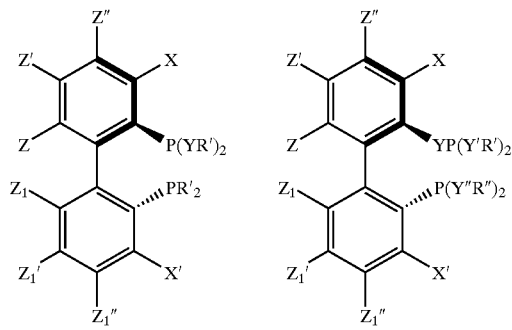

-continued

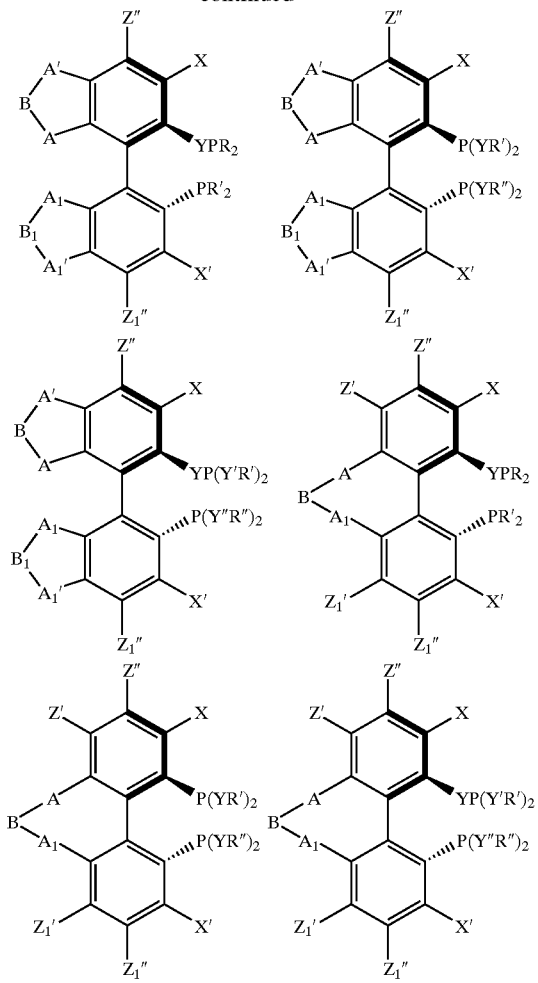

wherein each X and X' is independently selected from the group consisting of: alkyl, aryl, substituted alkyl, substituted aryl, OR, SR, NR$_2$, COOR, halide, SiR$_3$, P(O)R$_2$, P(O)(OR)$_2$ and P(OR)$_2$;

wherein each Z and Z$_1$ is independently selected from the group consisting of: alkyl, aryl, substituted alkyl, substituted aryl, OR, SR, NR$_2$, COOR, halide, SiR$_3$, P(O)R$_2$, P(O)(OR)$_2$ and P(OR)$_2$; or wherein Z and Z$_1$ together form the bridging group A-B-A$_1$;

wherein each Z', Z'', Z$_1$' and Z$_1$'' is independently selected from the group consisting of: H, alkyl, aryl, substituted alkyl, substituted aryl, OR, SR, NR$_2$, COOR, halide, SiR$_3$, P(O)R$_2$, P(O)(OR)$_2$ and P(OR)$_2$; or wherein Z' and Z together form the bridging group A'-B-A; Z' and Z together form a fused cycloaliphatic or aromatic group; Z$_1$ and Z$_1$' together form the bridging group A$_1$-B$_1$-A$_1$'; and/or Z$_1$ and Z$_1$' together form a fused cycloaliphatic or aromatic group;

wherein each A, A', A$_1$ and A$_1$' is independently selected from the group consisting of: O, CH$_2$, NH, NR, S, CO and a bond;

wherein each B and B$_1$ is independently selected from the group consisting of: linear, branched or cyclic alkylene of 1 to 6 carbon atoms, arylene of 6 to 12 carbon atoms, O, CH$_2$, NH, NR, S, CO, SO$_2$, P(O)R, P(O)OR, POR, SiR$_2$ and a bond;

wherein each YR', YR'', Y'R' and Y''R'' is independently selected from the group consisting of: alkyl, substituted alkyl, aryl, substituted aryl, alkoxide and aryloxide; or wherein two YR', YR'', Y'R' or Y''R'' groups together form an alkylene, arylene, alkylenediamino, arylenediamino, alkelenedioxyl or arylenedioxyl;

wherein each R, R' and R'' is independently selected from the group consisting of: alkyl, substituted alkyl, aryl, aralkyl and alkaryl of 1 to 22 carbon atoms; or wherein two R groups, two R' groups or two R'' group together form an alkylene or arelene group; and wherein each Y, Y' and Y'' is independently selected from the group consisting of: O, CH$_2$, NH, S and a bond between carbon and phosphorus; with the proviso that when the Y group at the 2' position is a bond between carbon and phosphorus, X' is hydrogen.

In another preferred embodiment, the present invention includes compounds represented by the following formulas:

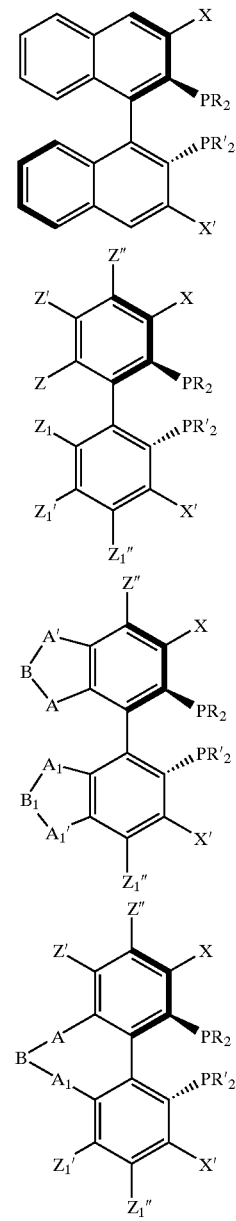

wherein each X is independently selected from the group consisting of: alkyl, aryl, substituted alkyl, substituted aryl, OR, SR, NR$_2$, COOR, halide, SiR$_3$, P(O)R$_2$, P(O)(OR)$_2$ and P(OR)$_2$;

wherein each X' is independently selected from the group consisting of: hydrogen, alkyl, aryl, substituted alkyl, substituted aryl, OR, SR, NR$_2$, COOR, halide, SiR$_3$, P(O)R$_2$, P(O)(OR)$_2$ and P(OR)$_2$;

wherein each Z and Z$_1$ is independently selected from the group consisting of: alkyl, aryl, substituted alkyl, substituted aryl, OR, SR, NR$_2$, COOR, halide, SiR$_3$, P(O)R$_2$, P(O)(OR)$_2$ and P(OR)$_2$;

wherein each Z', Z'', Z$_1$' and Z$_1$'' is independently selected from the group consisting of: H, alkyl, aryl, substituted alkyl, substituted aryl, OR, SR, NR$_2$, COOR, halide, SiR$_3$, P(O)R$_2$, P(O)(OR)$_2$ and P(OR)$_2$;

wherein each A, A', A$_1$ and A$_1$' is independently selected from the group consisting of: O, CH$_2$, NH, NR, S, CO and a bond;

wherein each B and B$_1$ is independently selected from the group consisting of: linear, branched or cyclic alkylene of 1 to 6 carbon atoms, arylene of 6 to 12 carbon atoms, O, CH$_2$, NH, NR, S, CO, SO$_2$, P(O)R, P(O)OR, POR, SiR$_2$ and a bond;

wherein each R and R' is independently selected from the group consisting of: alkyl, substituted alkyl, aryl, substituted aryl, aralkyl and alkaryl of 1 to 22 carbon atoms, alkoxide and aryloxide; or wherein two R groups or two R' groups together form an alkylene, arelene, alkylenediamino, arylenediamino, alkelenedioxyl or arylenedioxyl groups.

The ligands of the present invention can be a racemic mixture of enantiomers. Preferably, the ligand is a non-racemic mixture of enantiomers, and more preferably, the ligand is one of the enantiomers. Preferably, the ligand has an optical purity of at least 85% ee, and more preferably, the ligand has an optical purity of at least 95% ee.

Selected examples of the chiral ligands according to the present invention are represented by the following formulas:

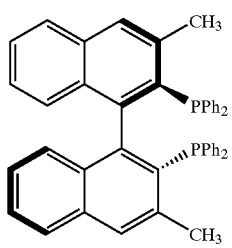

L1

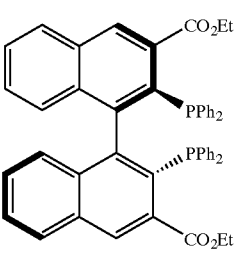

L2

-continued

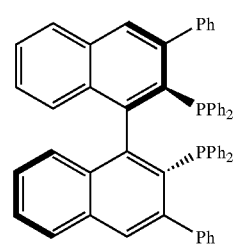

L3

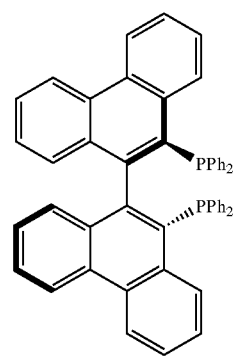

L4

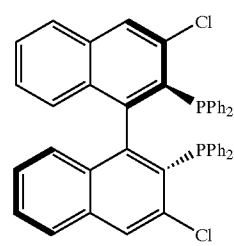

L5

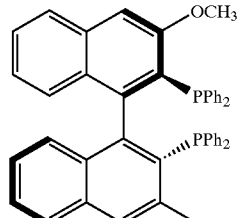

L6

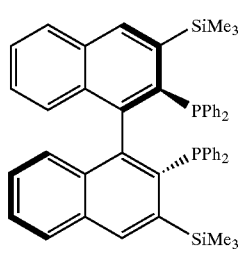

L7

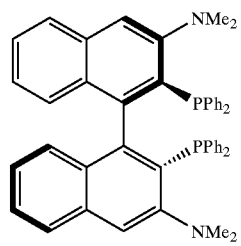

L8

-continued
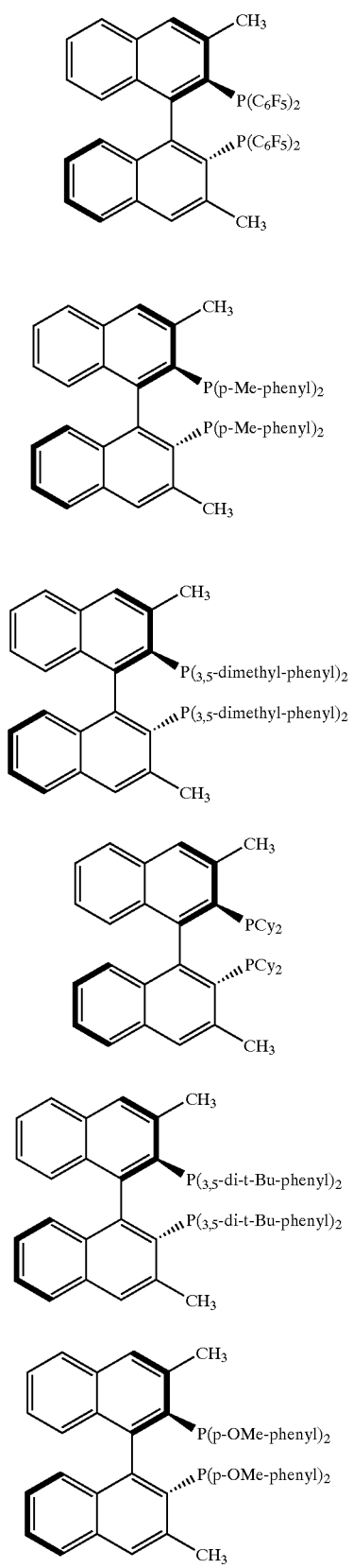
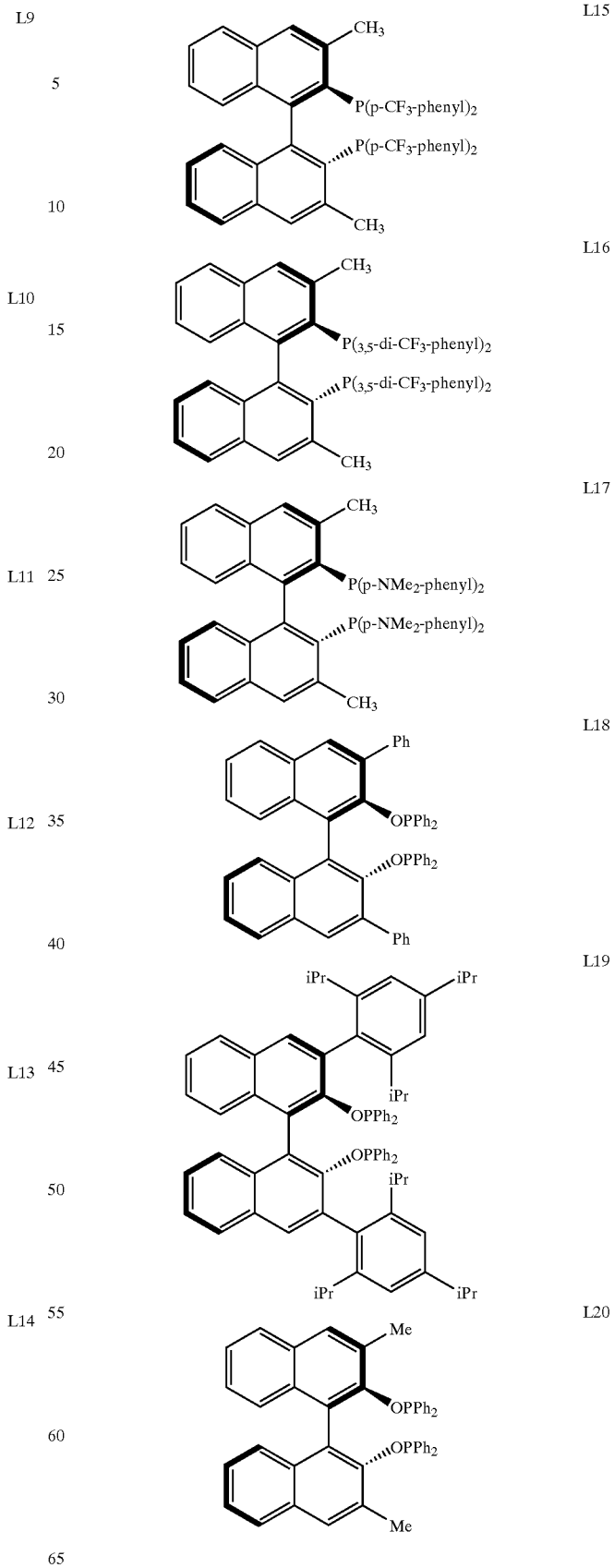

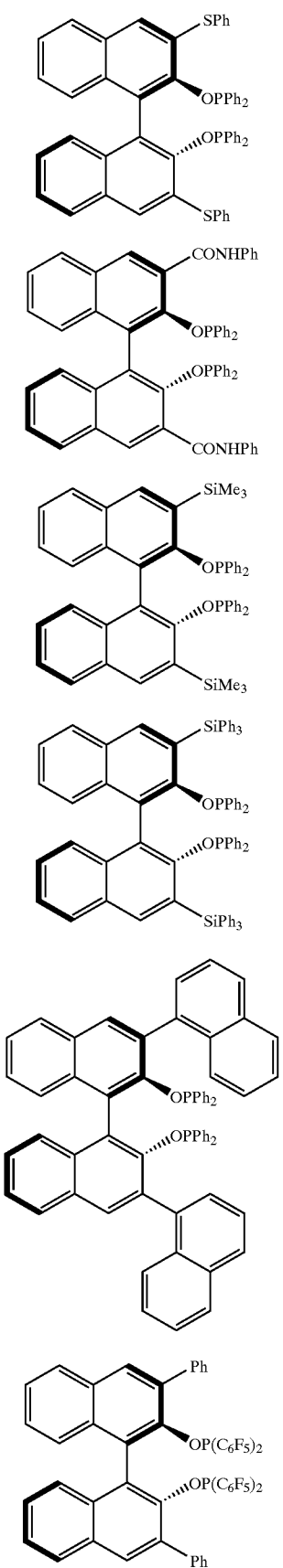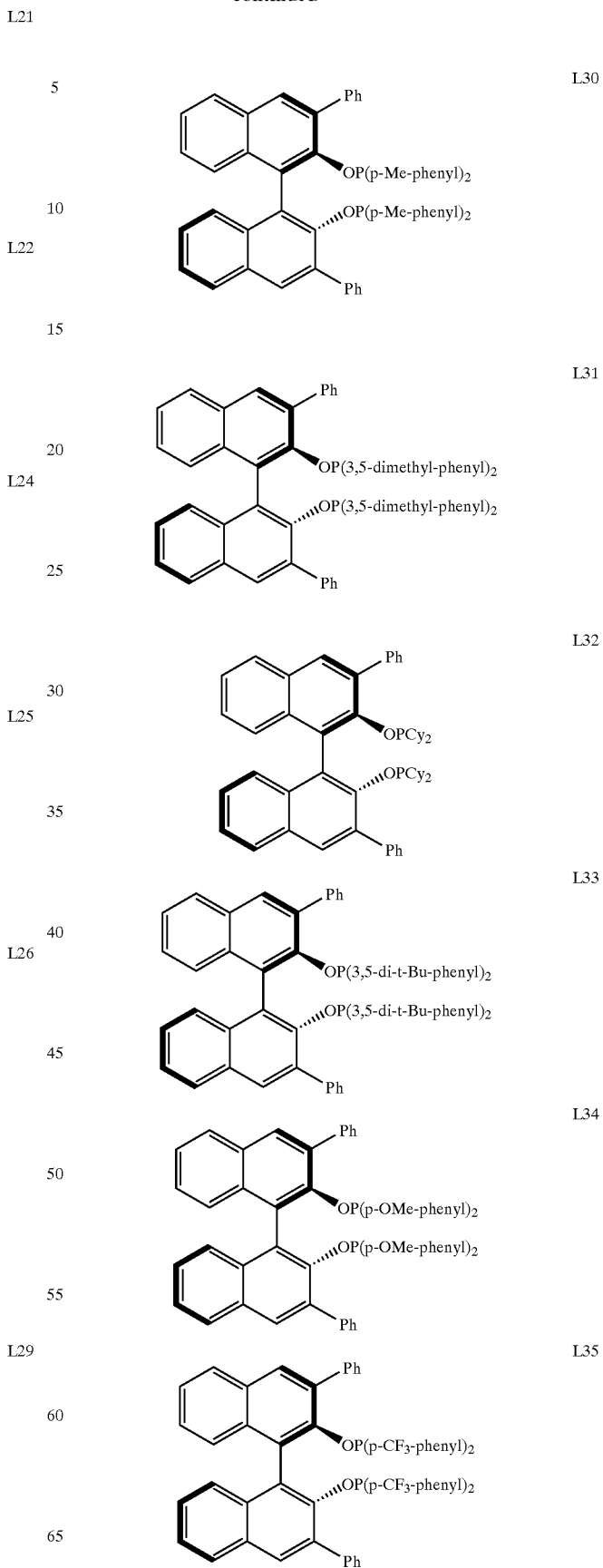

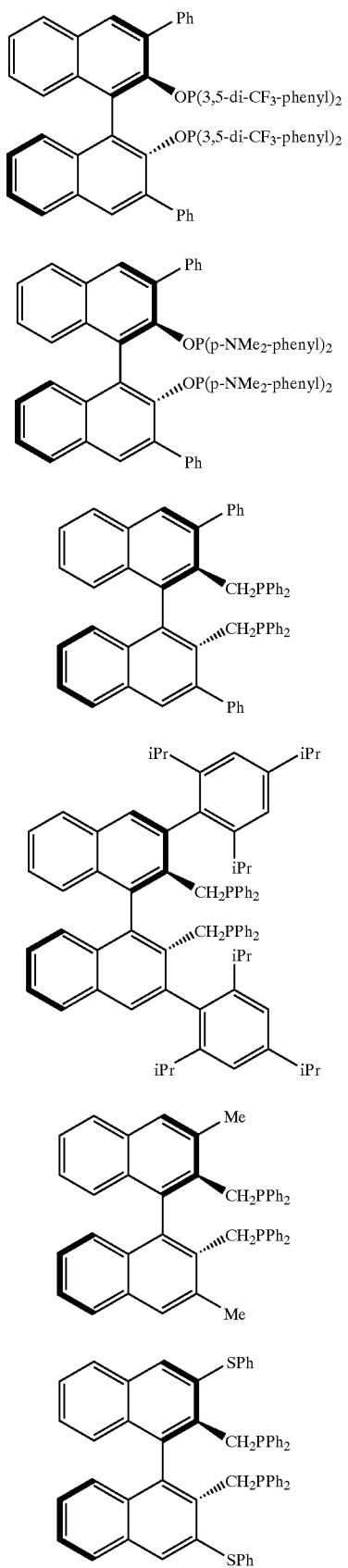
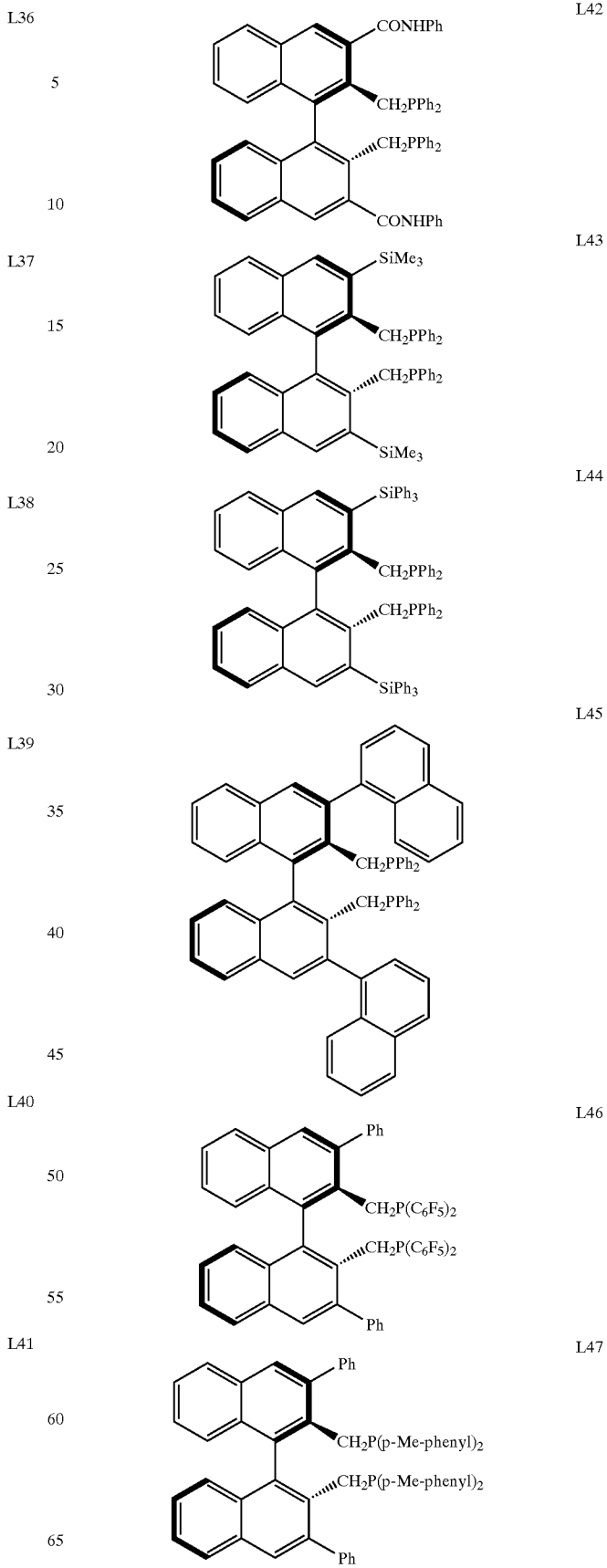

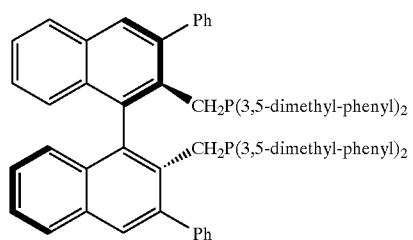
L48
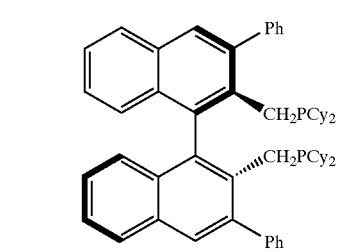
L49
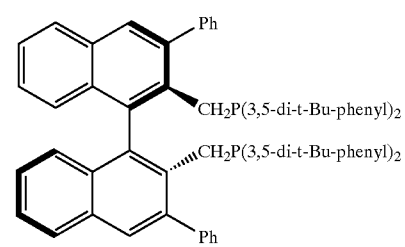
L50
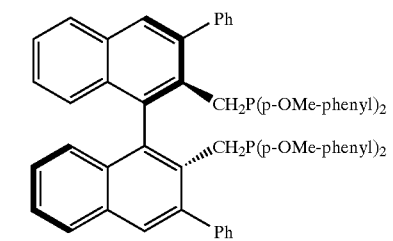
L51
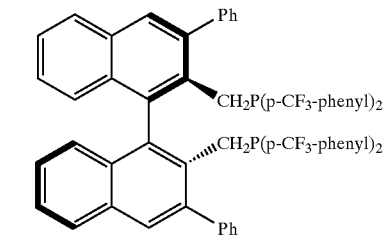
L52
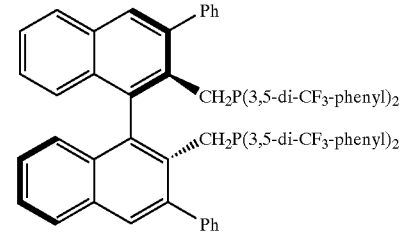
L53
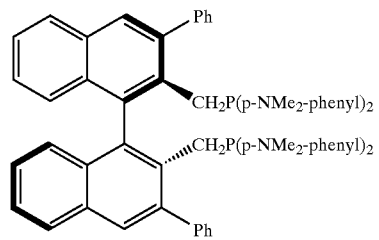
L54
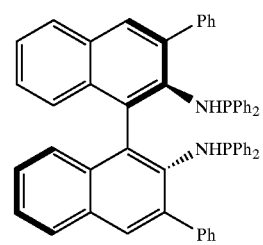
L55
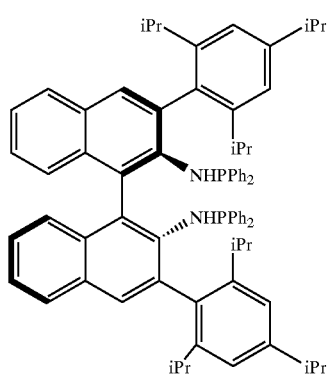
L56
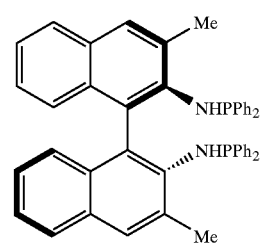
L57
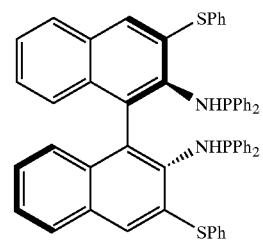
L58
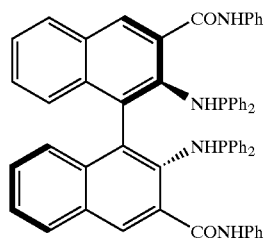
L59

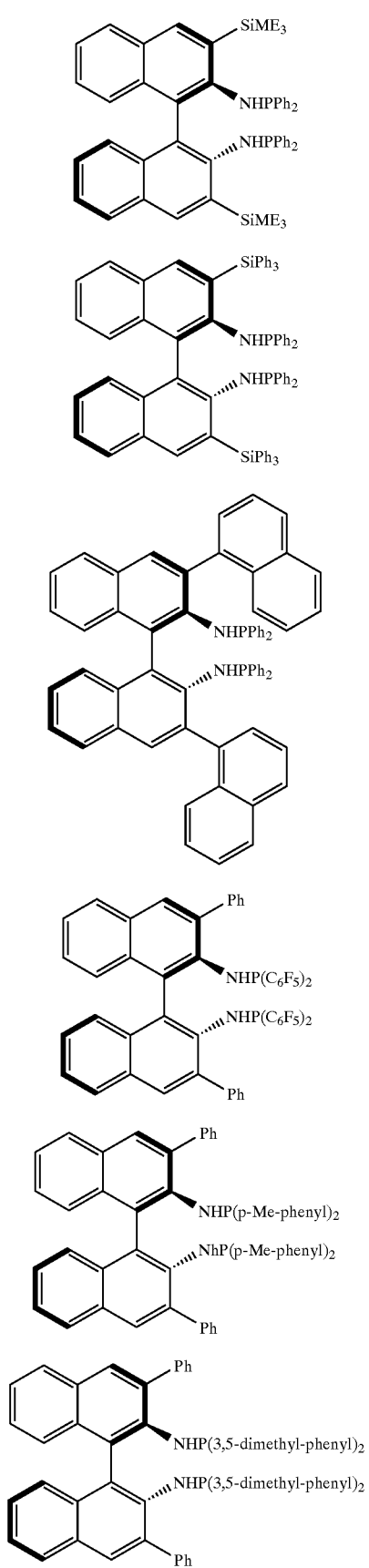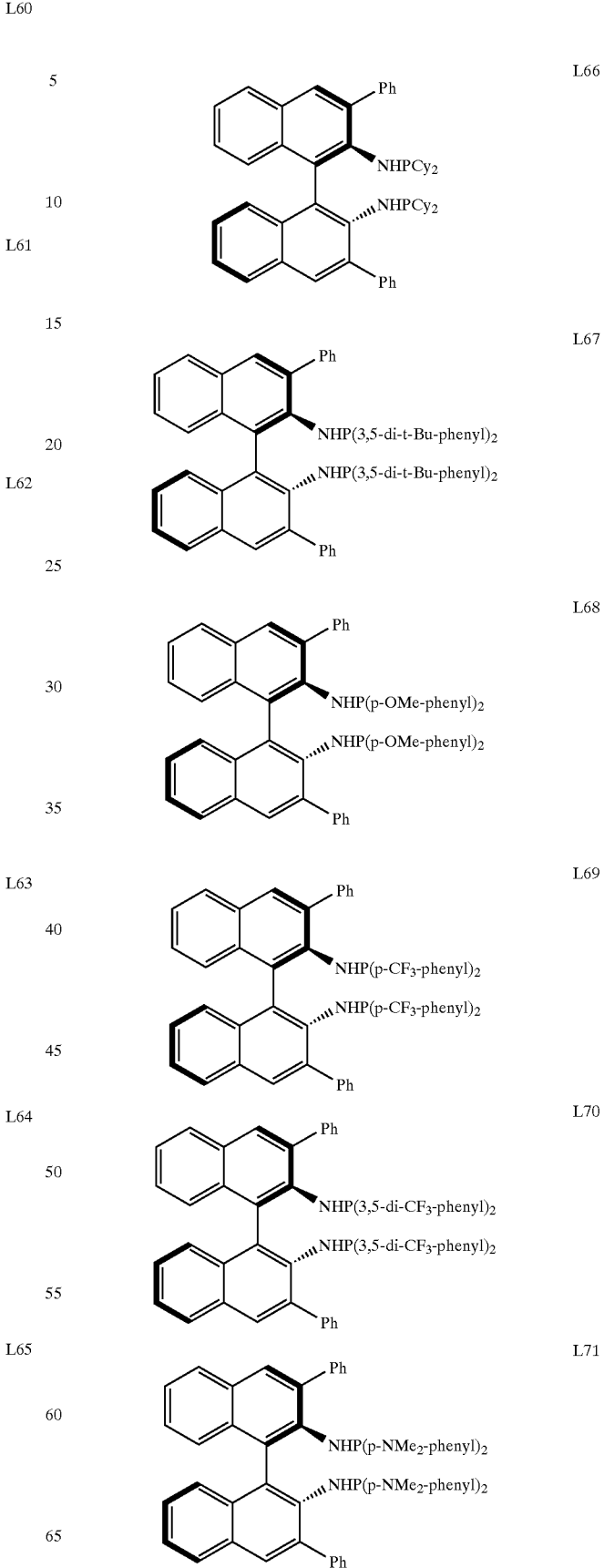

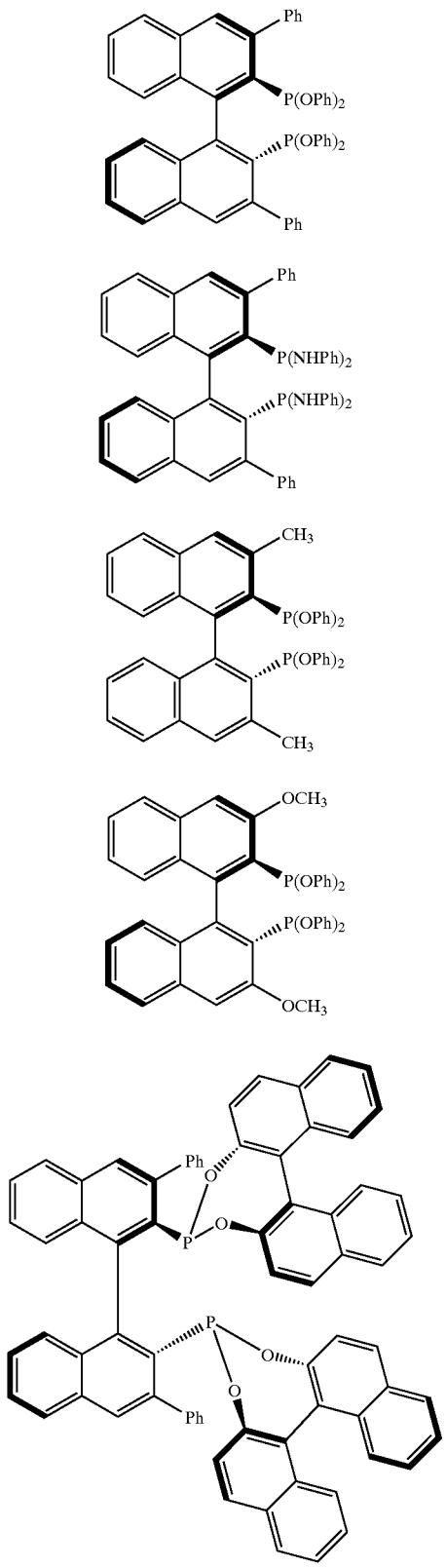
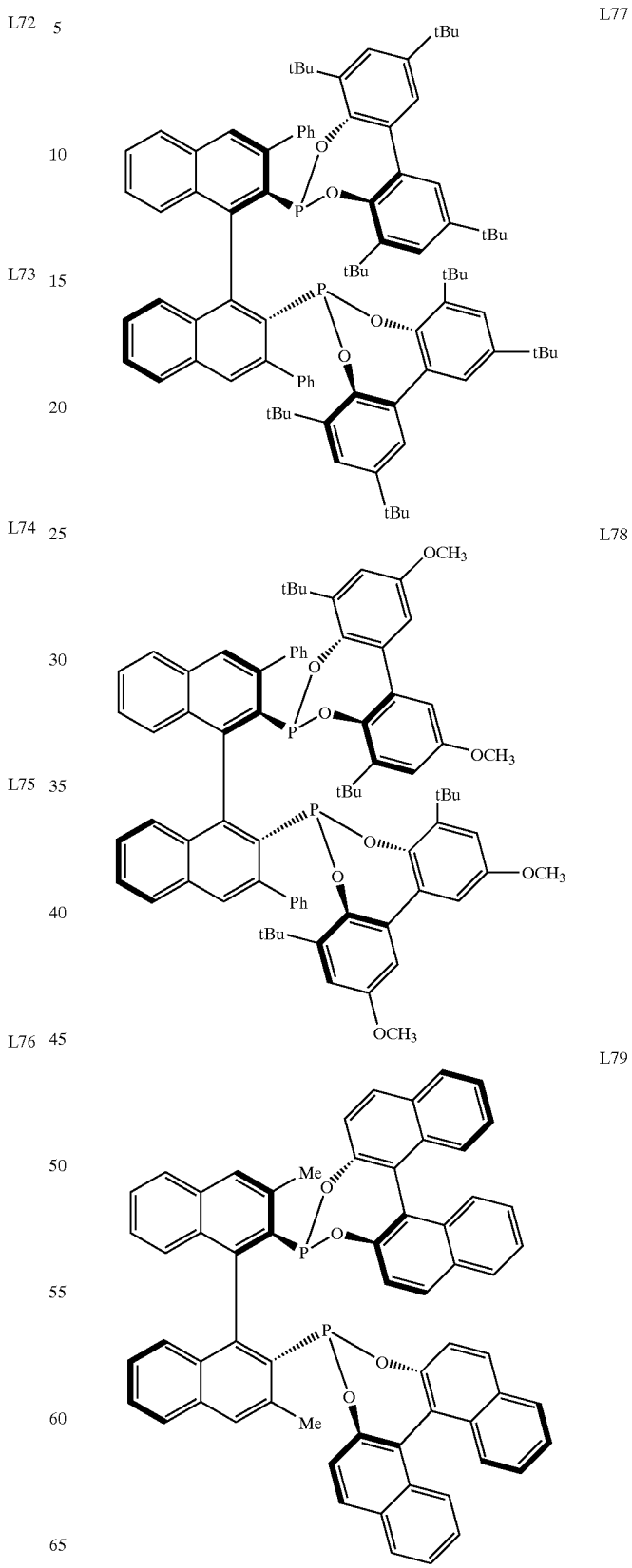

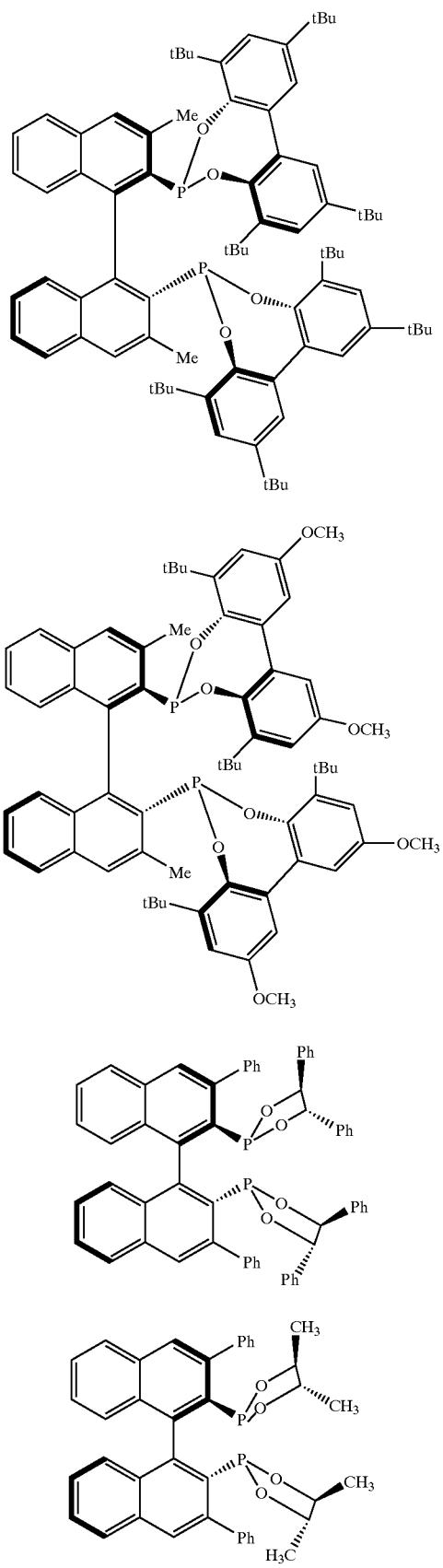
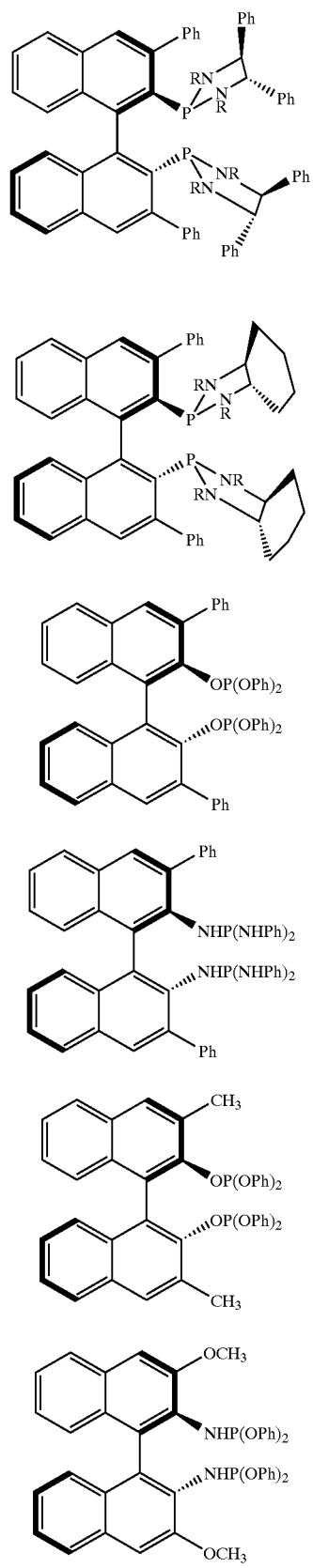

-continued
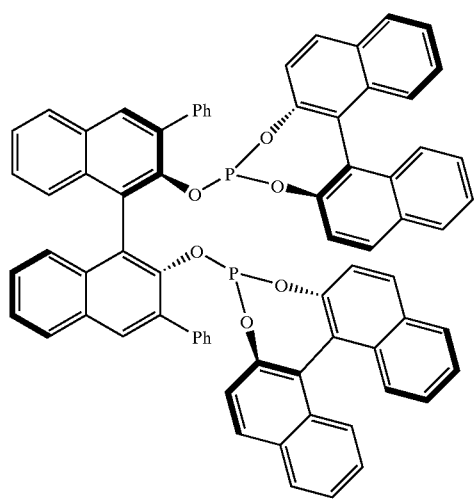
L90
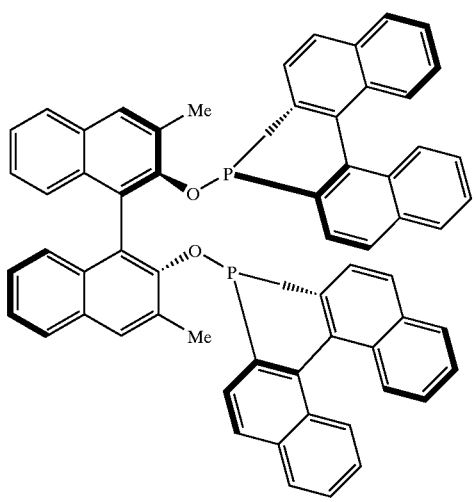
L93
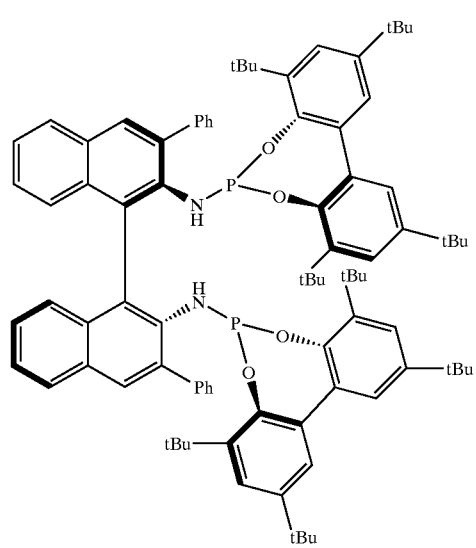
L91
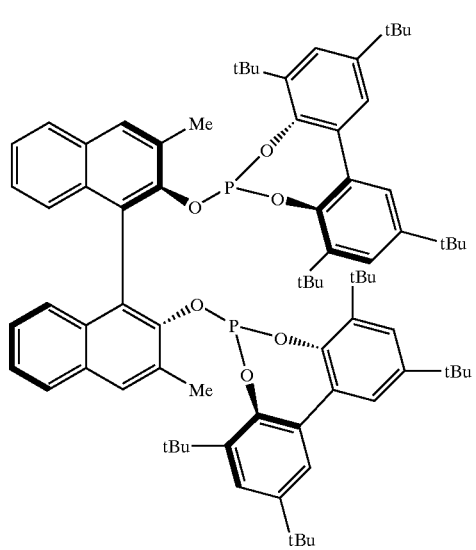
L94
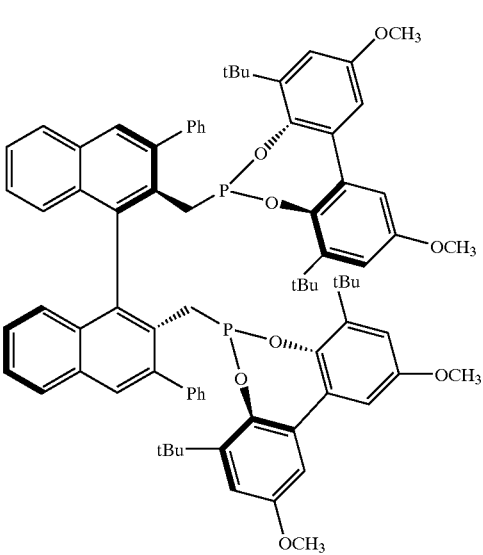
L92
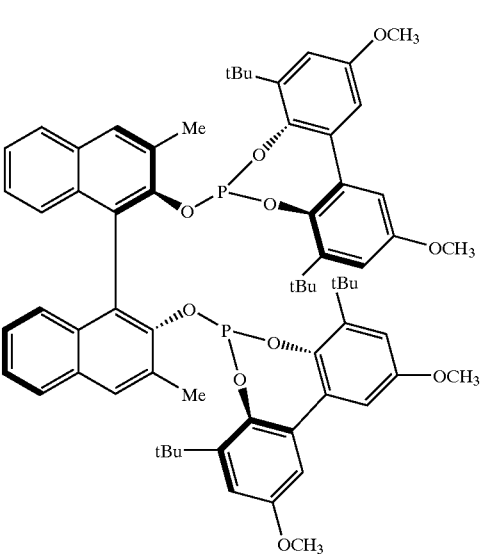
L95

L96
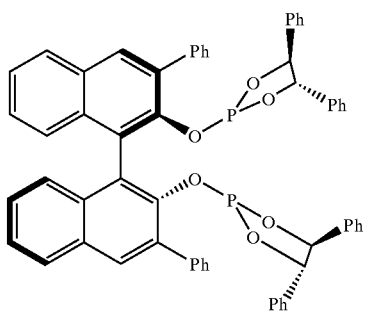
L97
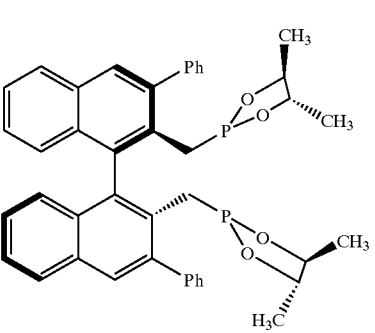
L98
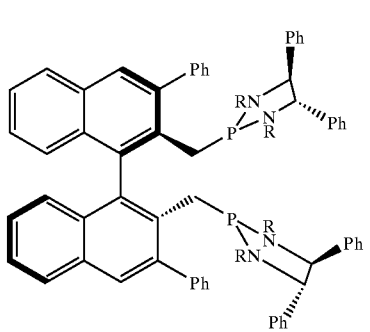
L99
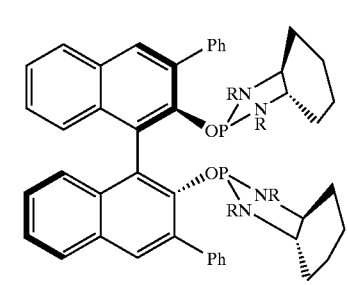
L100
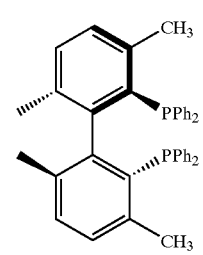
L101
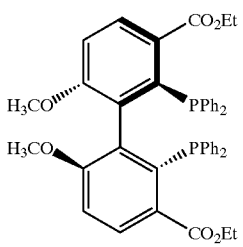
L102
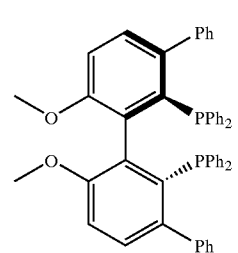
L103
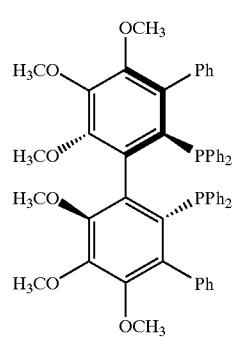
L104
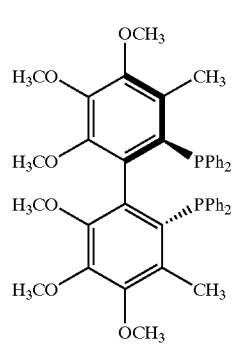
L105
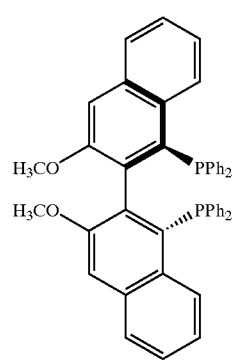

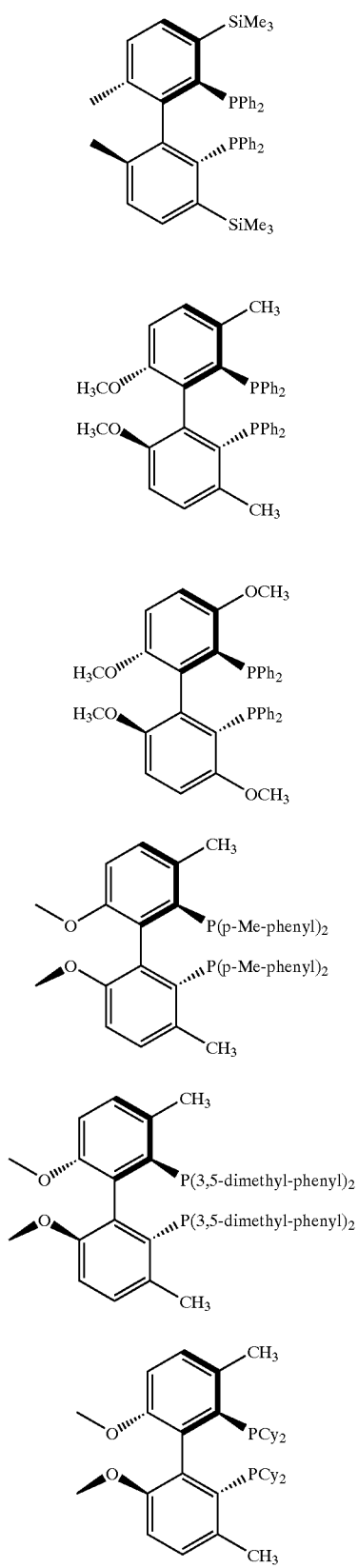

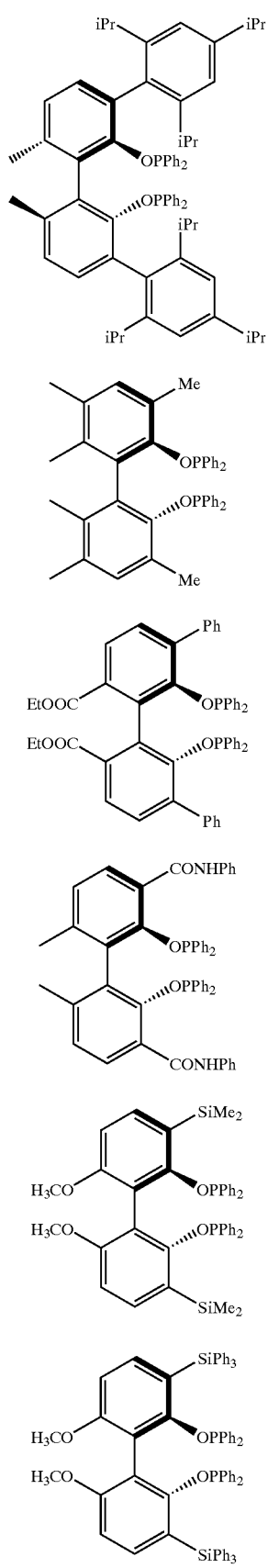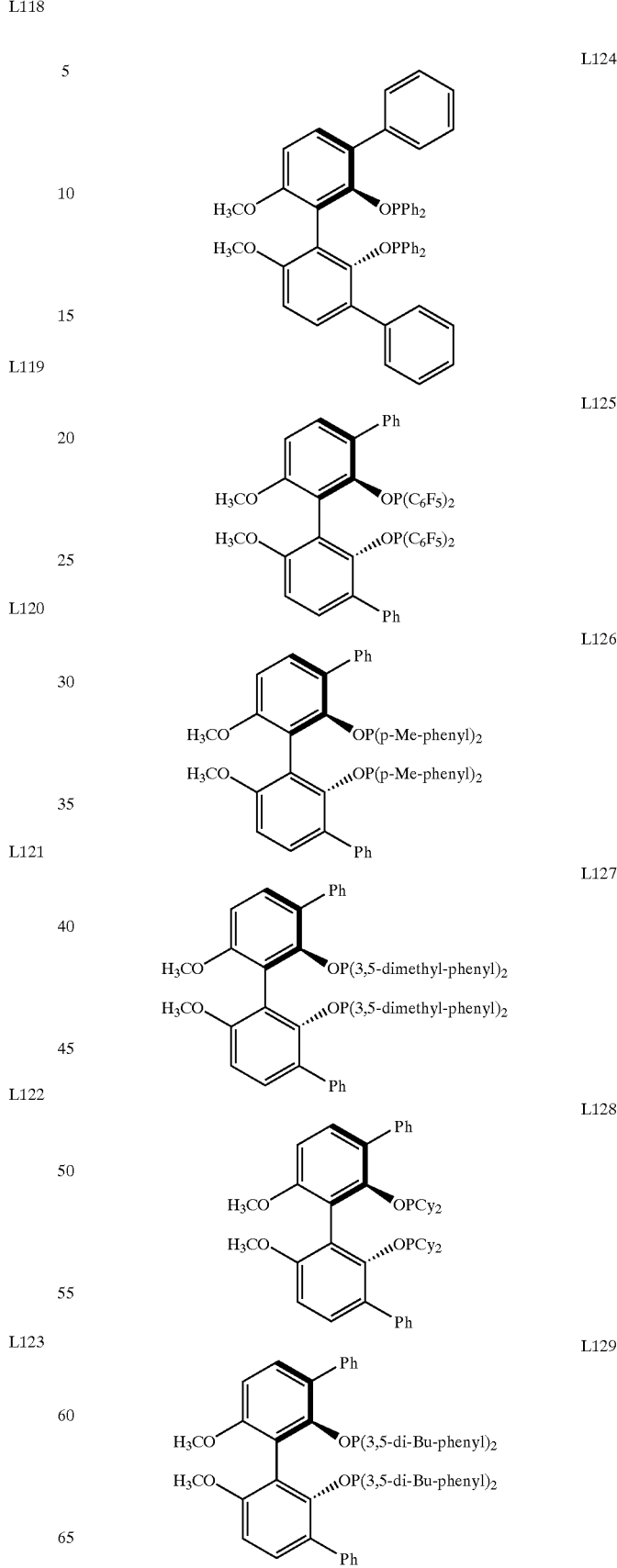

L130
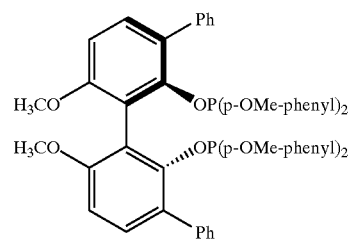
L131
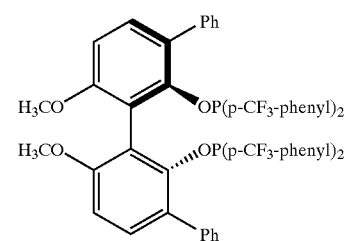
L132
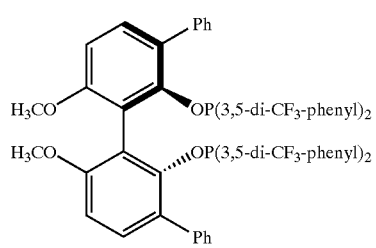
L133
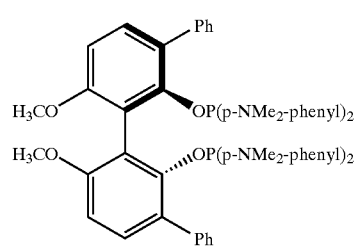
L134
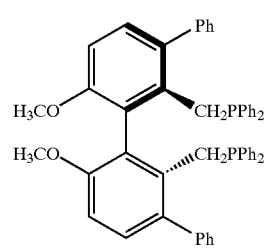
L135
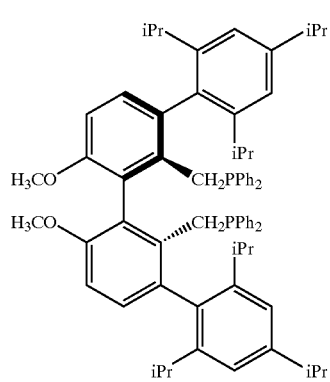
L136
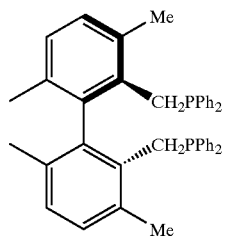
L137
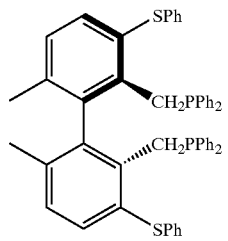
L138
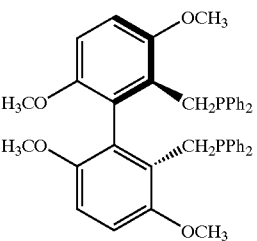
L139
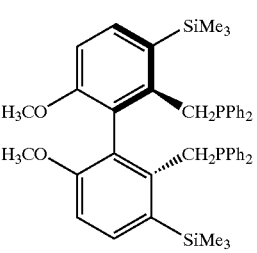
L140
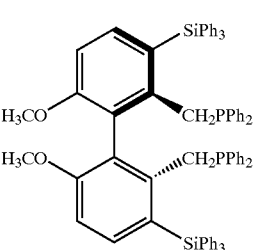
L141
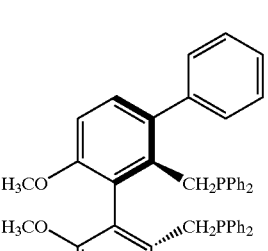

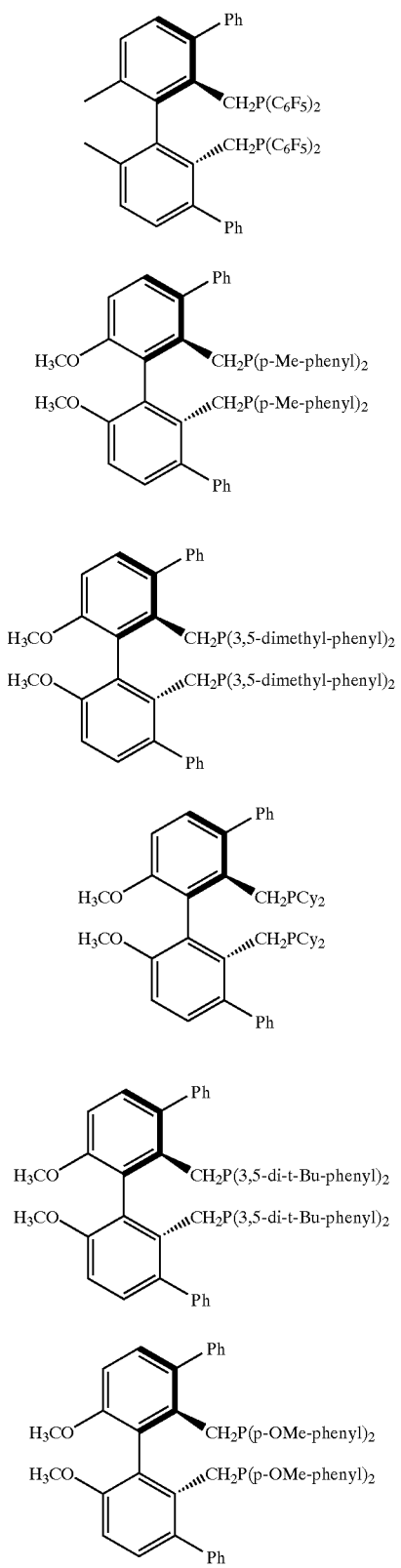
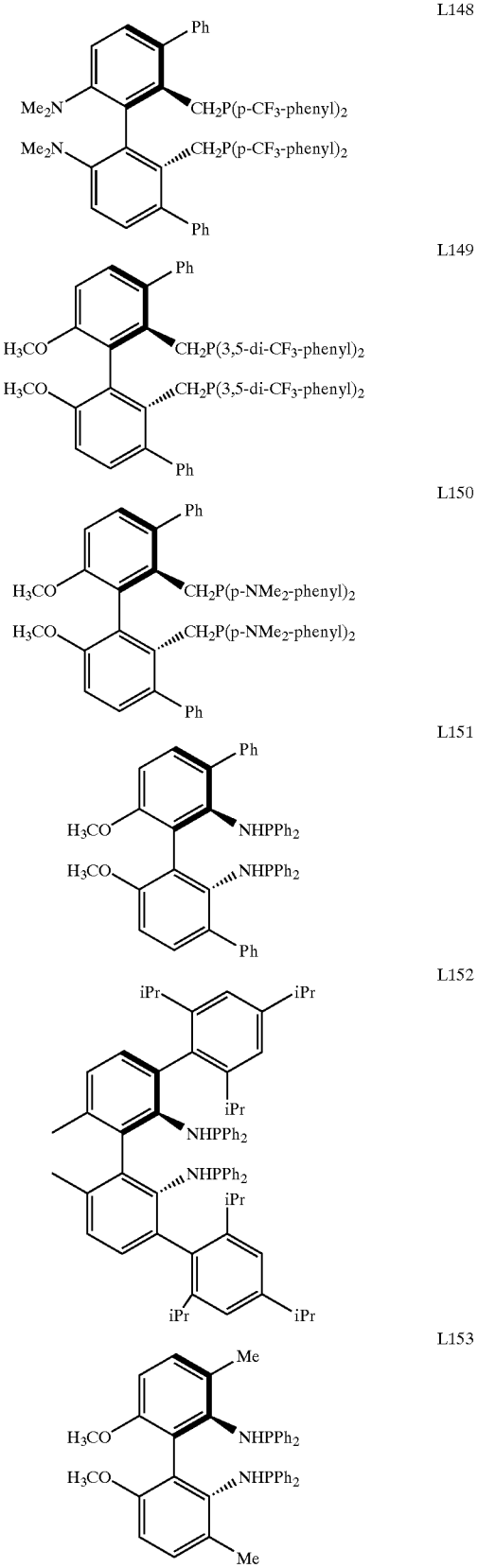

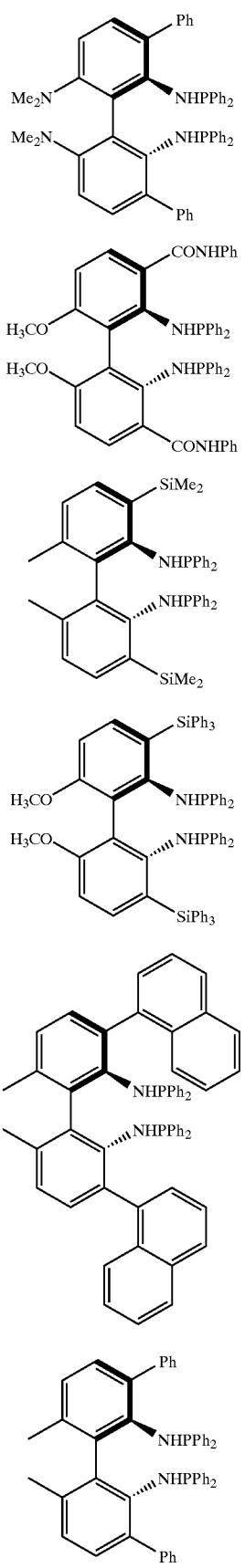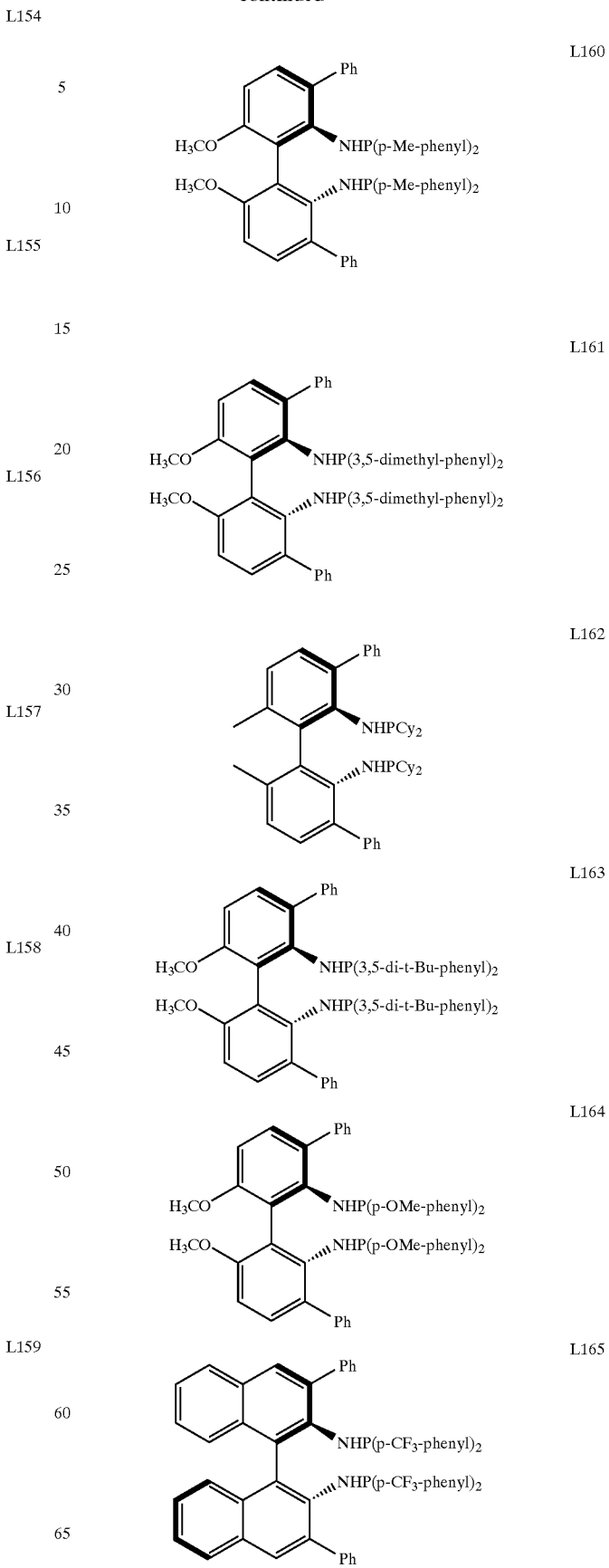

L166 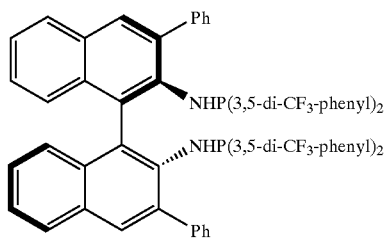
L167 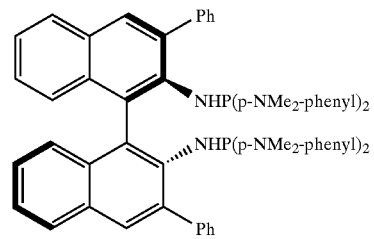
L168 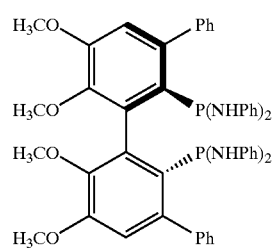
L169 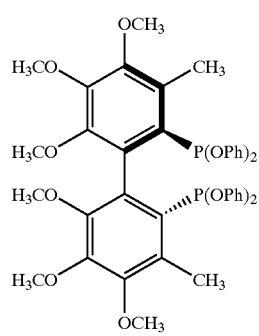
L170 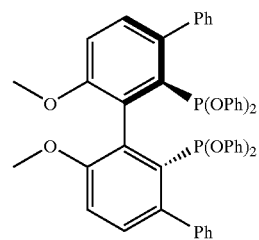
L171 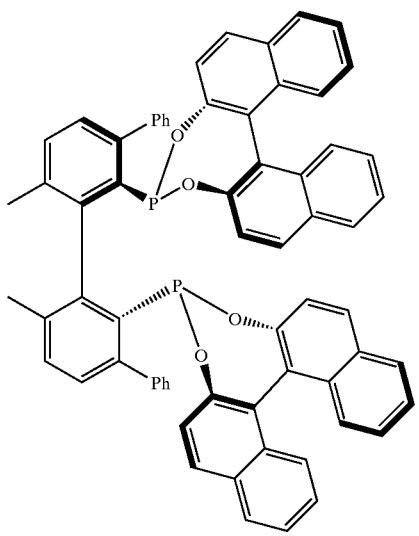
L172 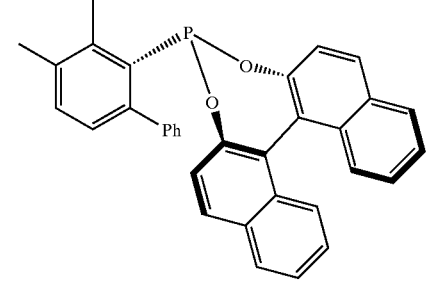
L173 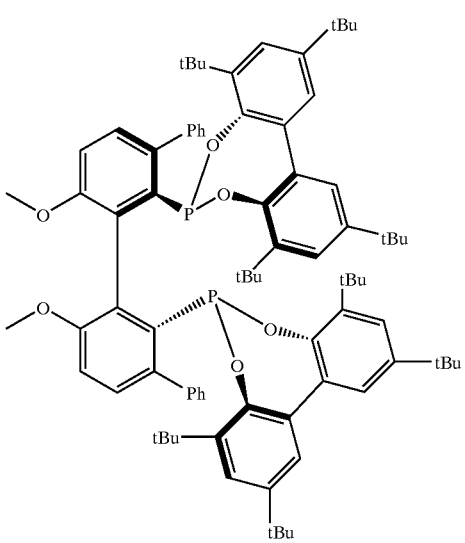
L174 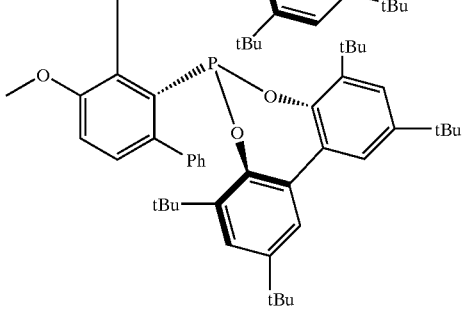

-continued
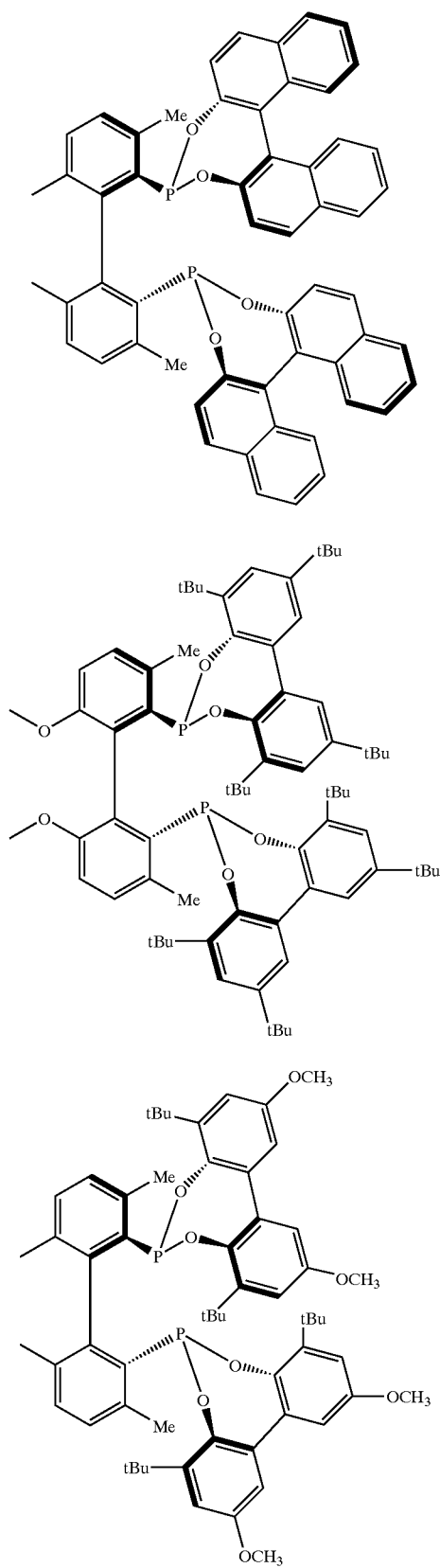
L175
L176
L177
-continued
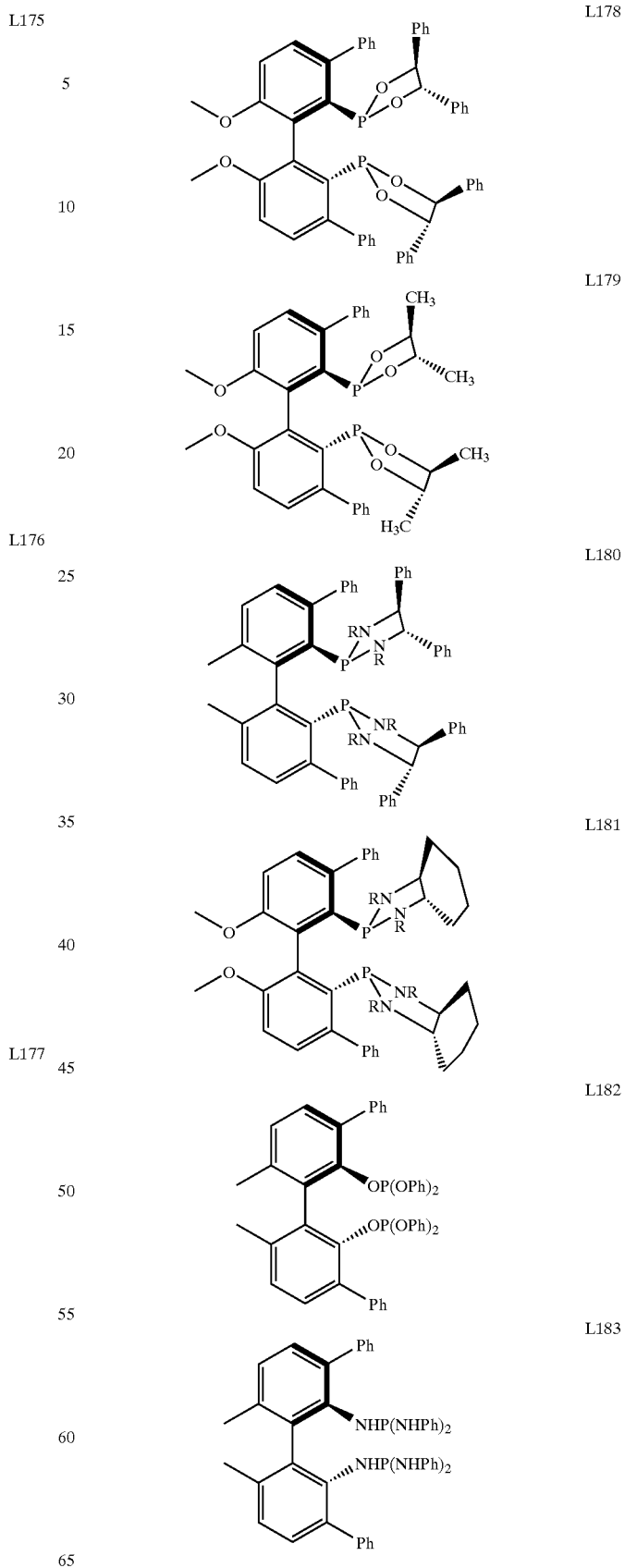
L178
L179
L180
L181
L182
L183

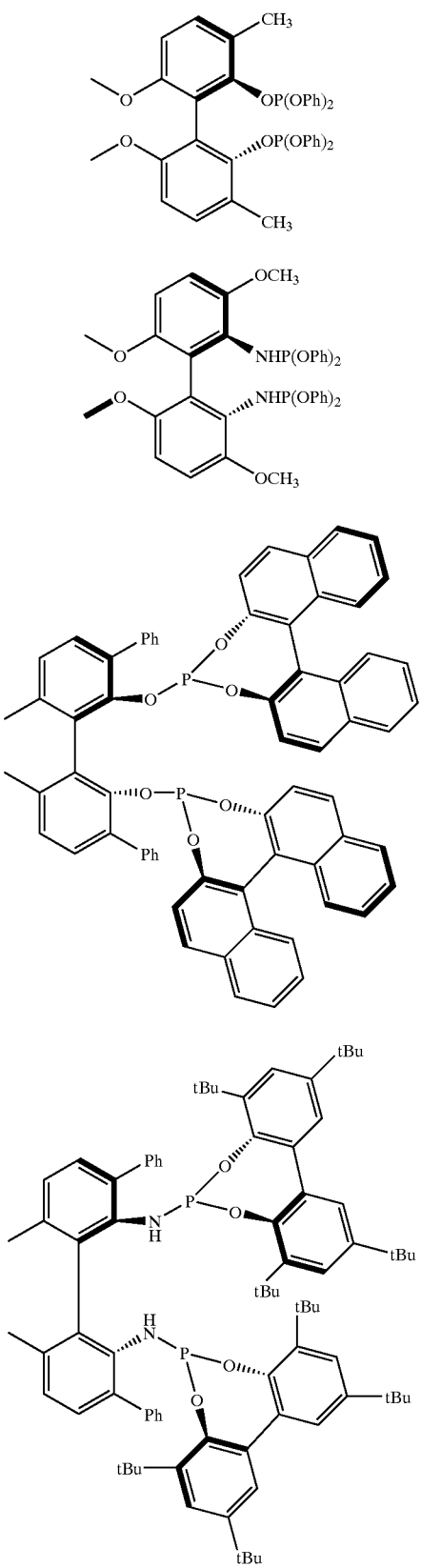
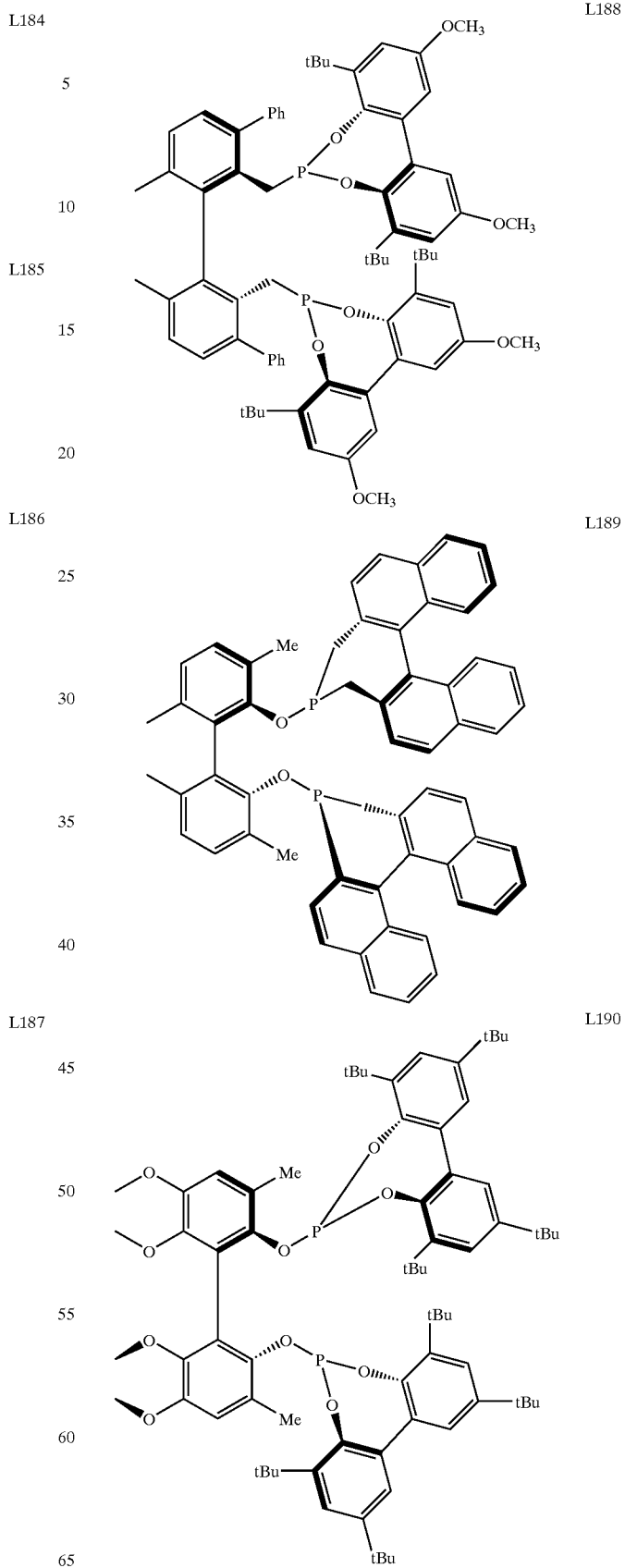

-continued
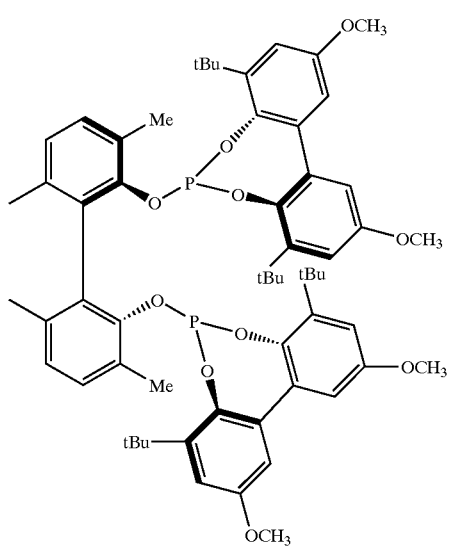
L191
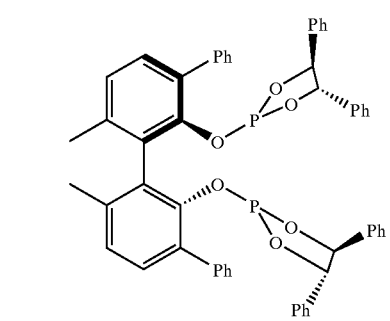
L192
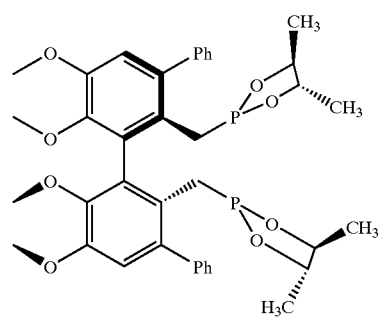
L193
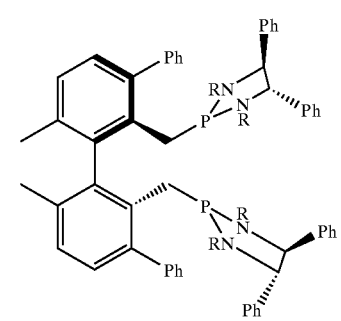
L194
-continued
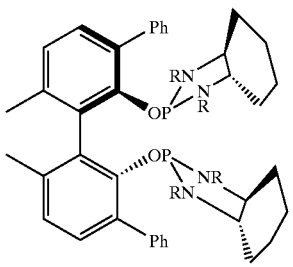
L195
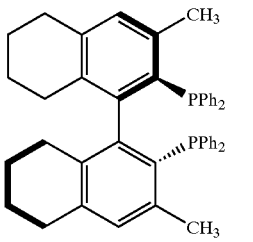
L196
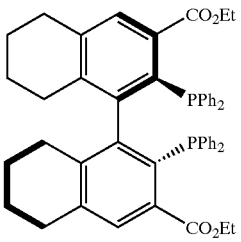
L197
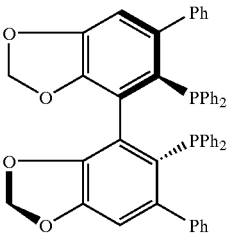
L198
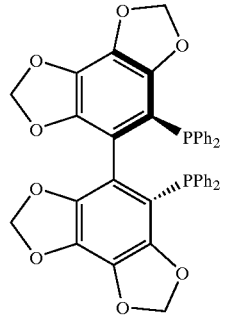
L199
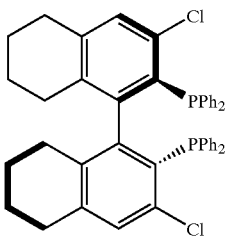
L200

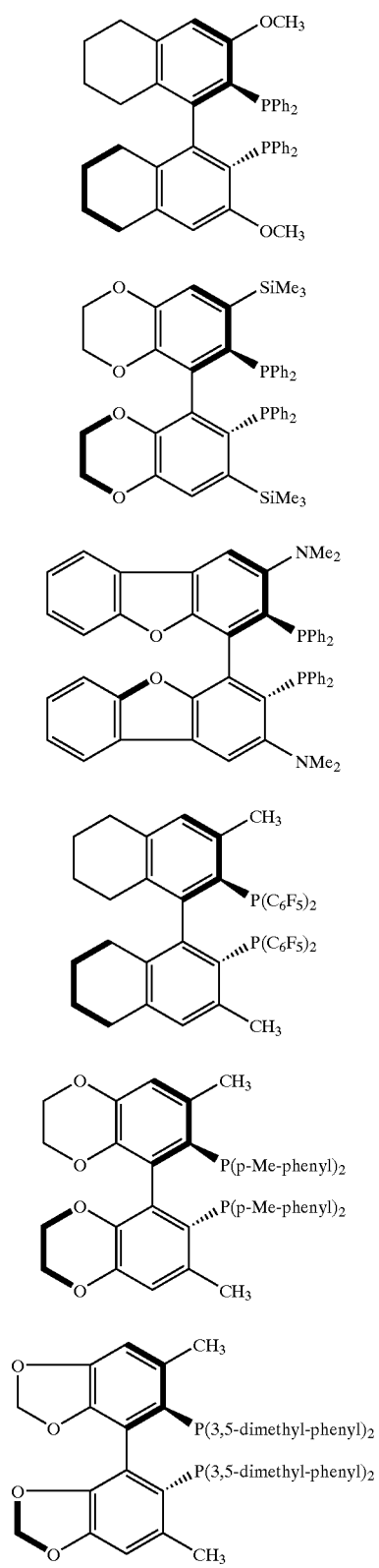
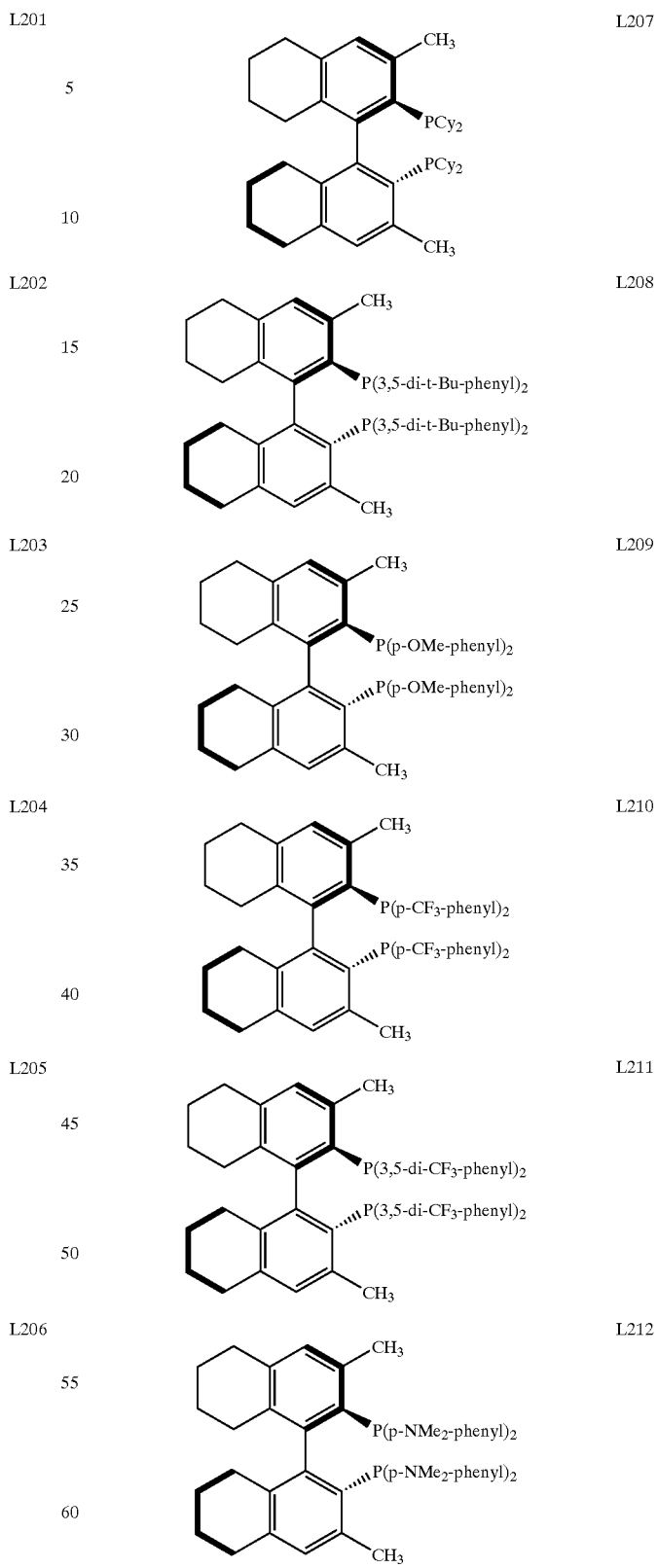

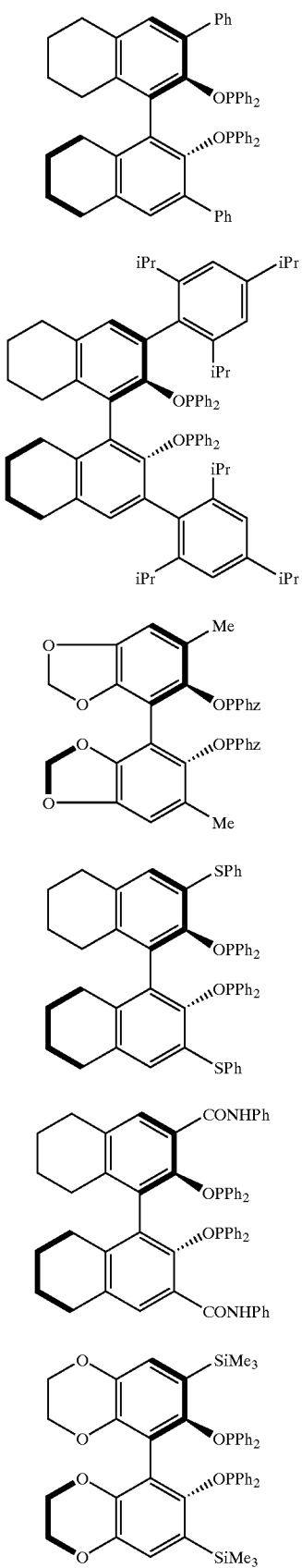
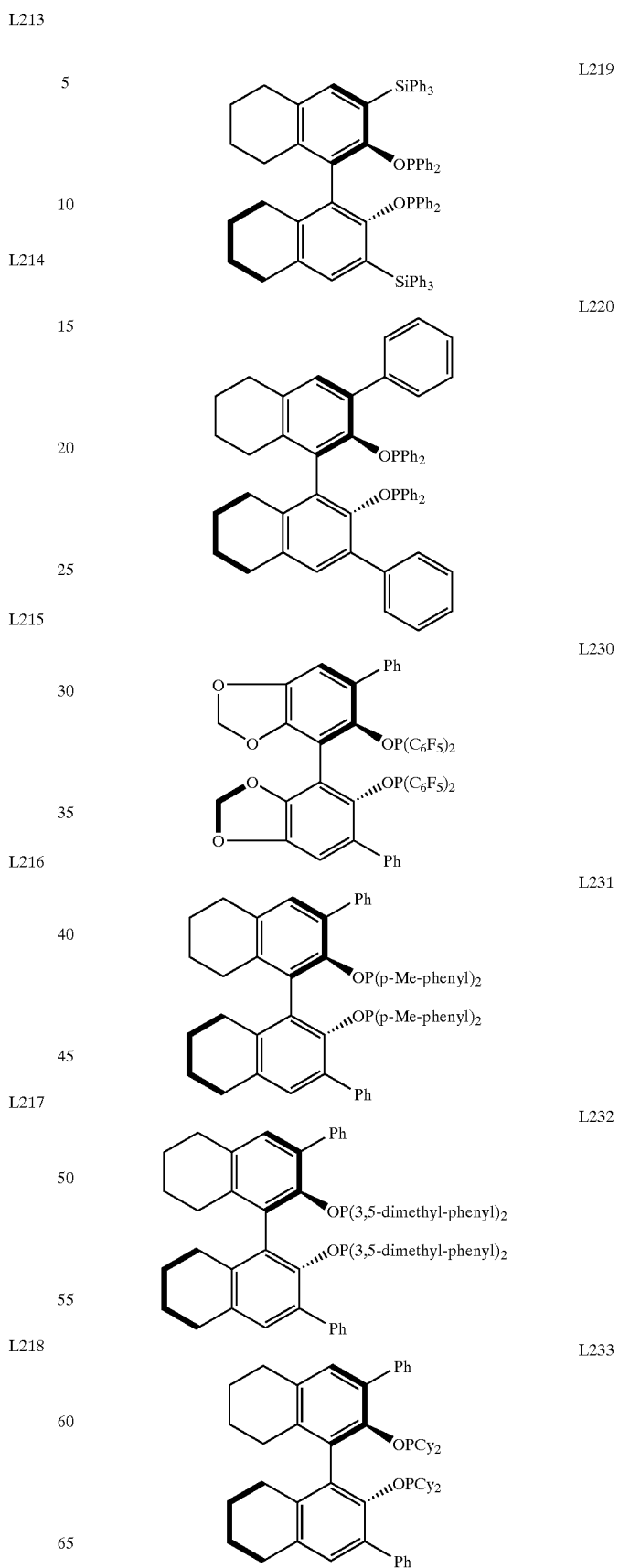

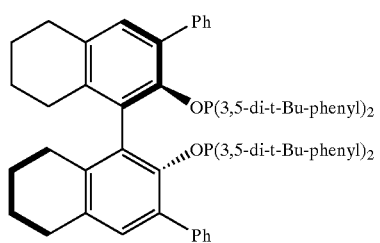 L234
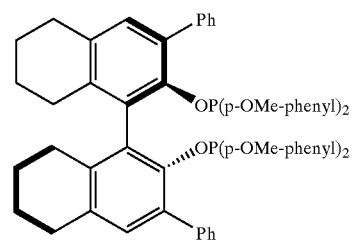 L235
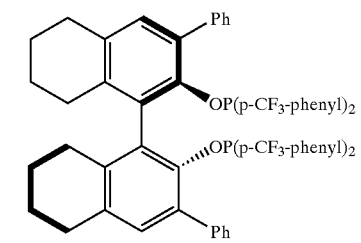 L236
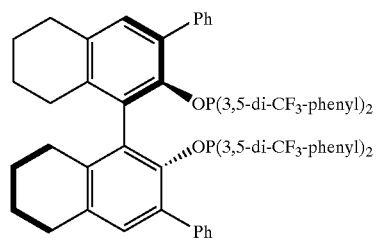 L237
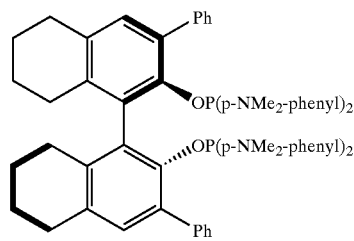 L238
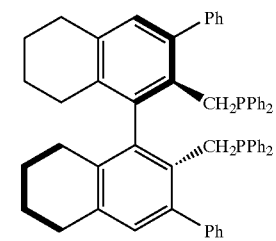 L239
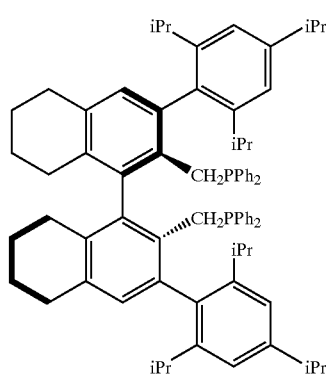 L240
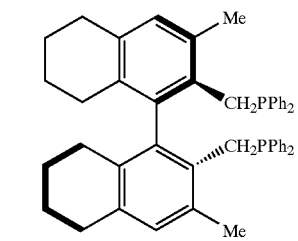 L241
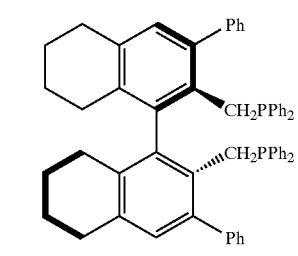 L242
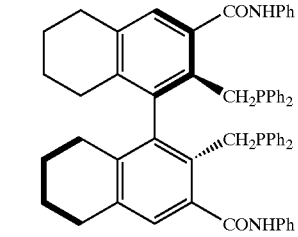 L243
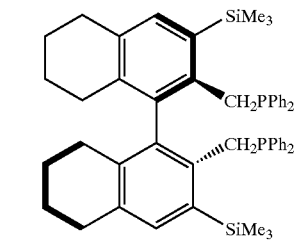 L244
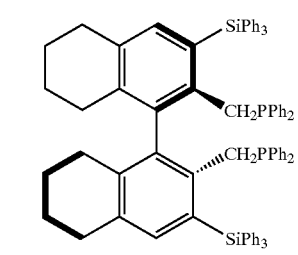 L245

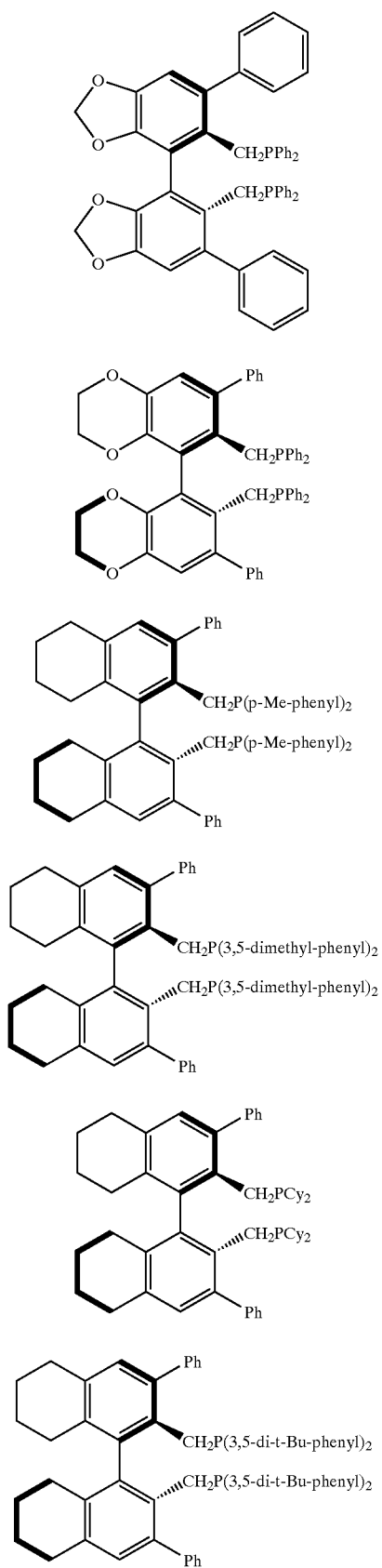
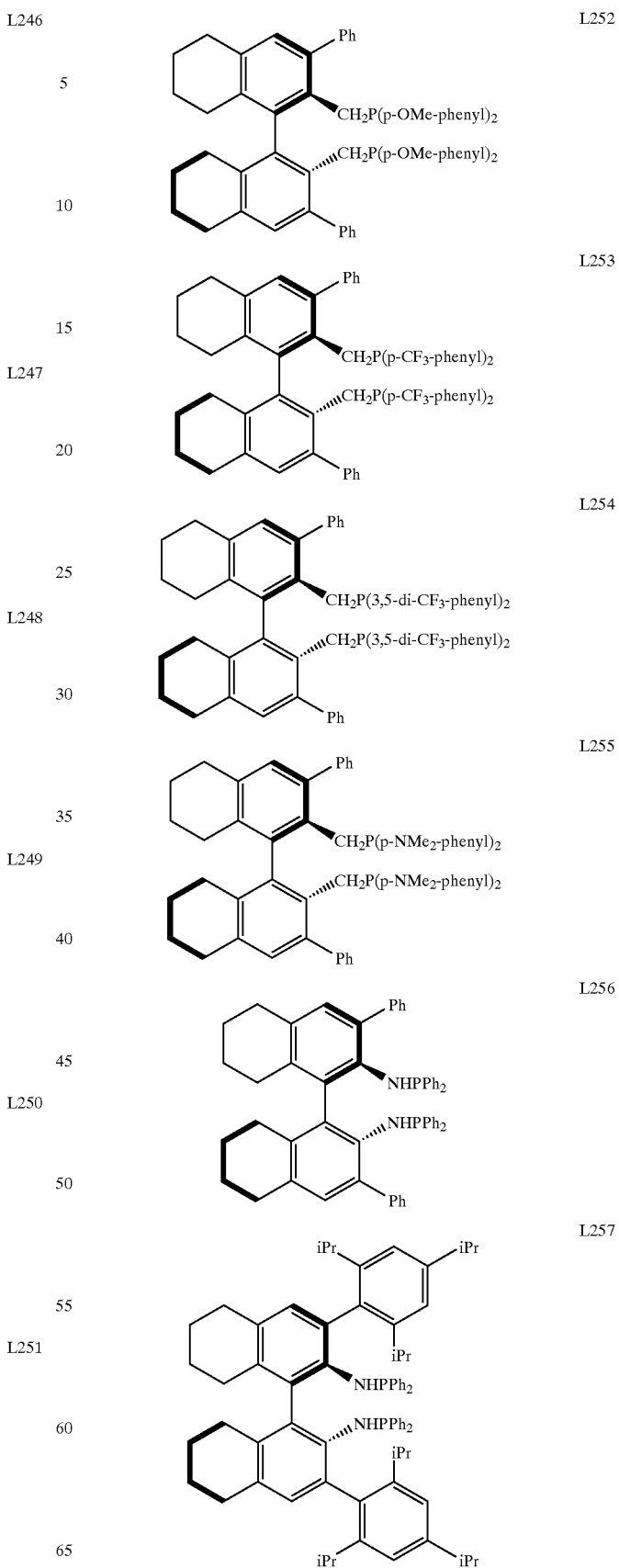

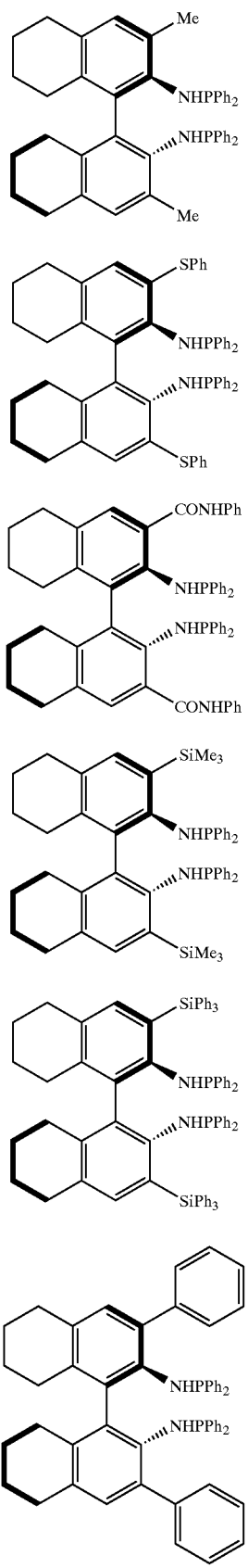
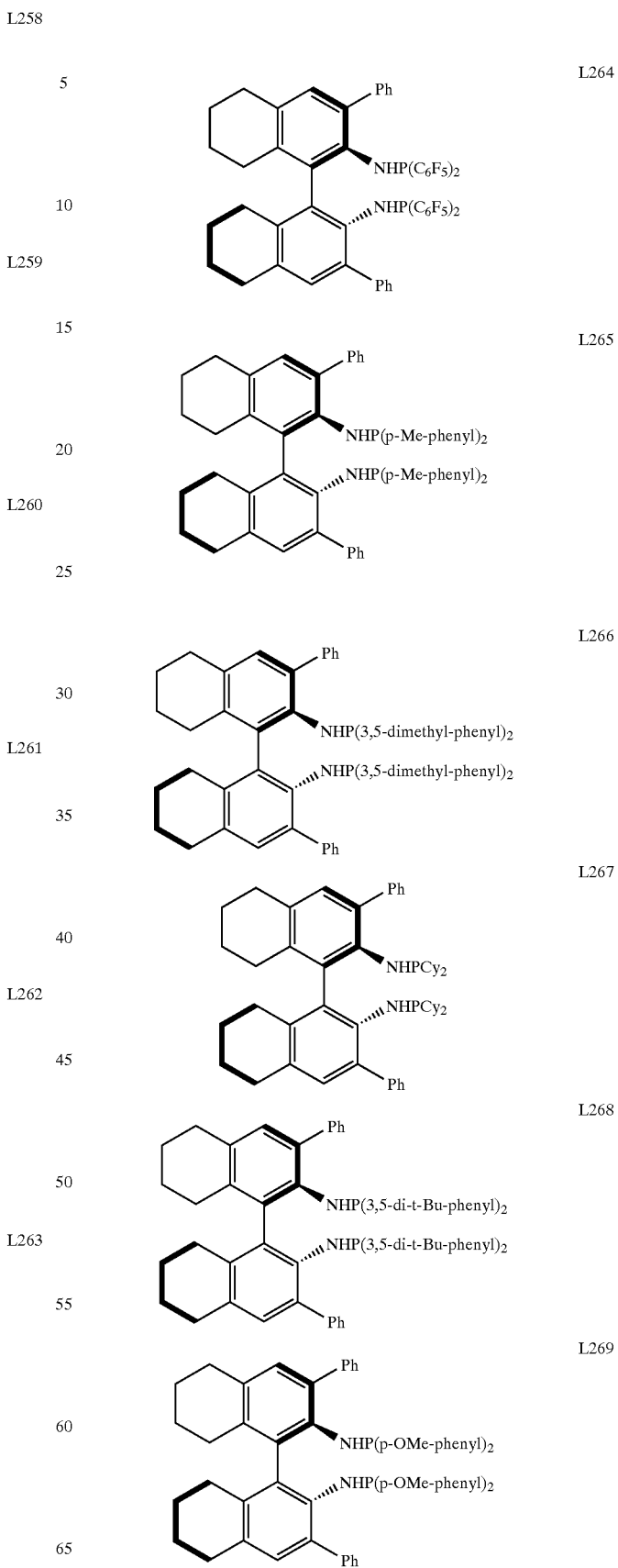

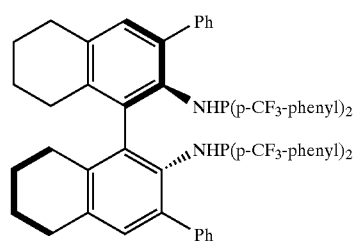
L270
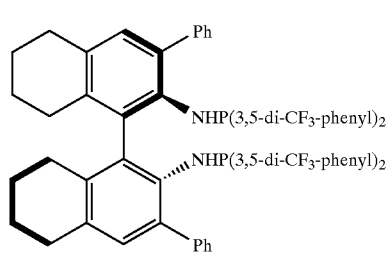
L271
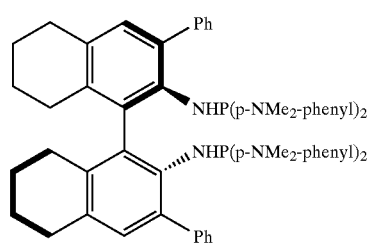
L272
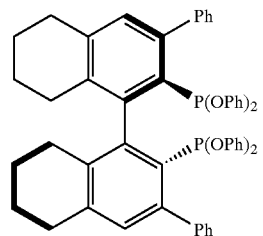
L273
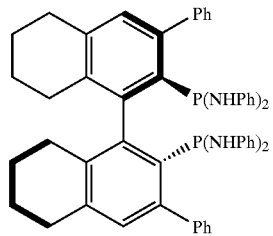
L274
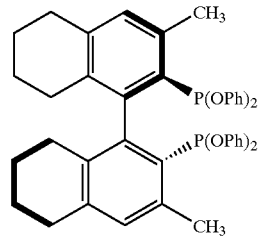
L275
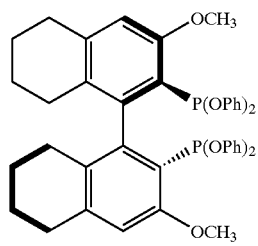
L276
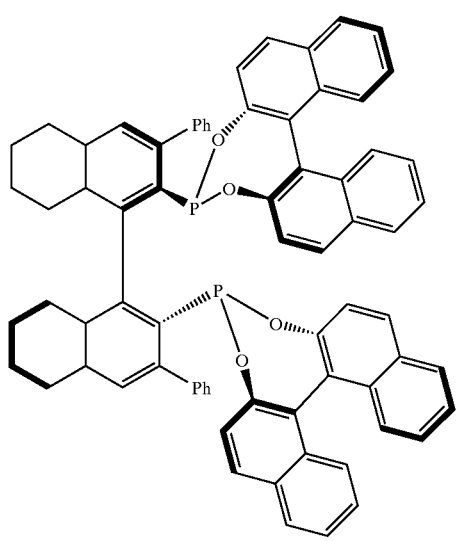
L277
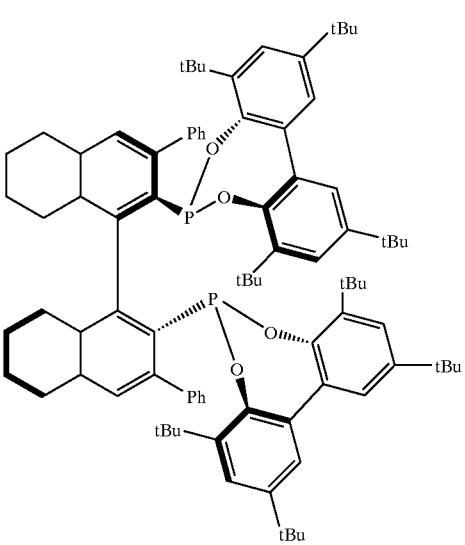
L278

L279
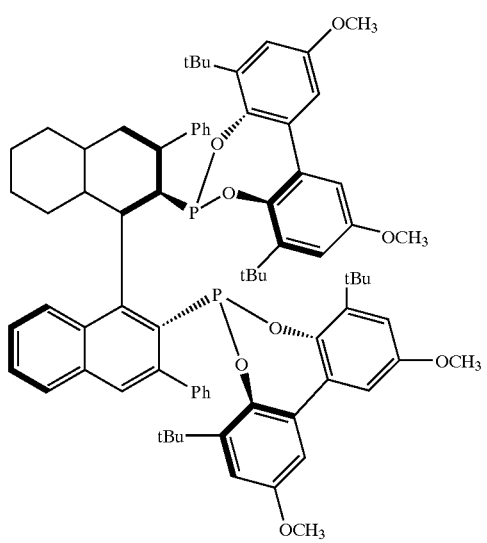
L280
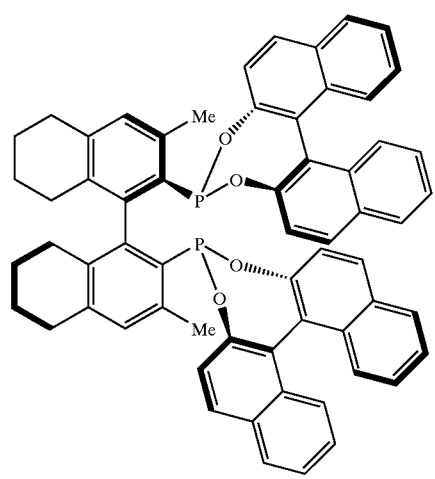
L281
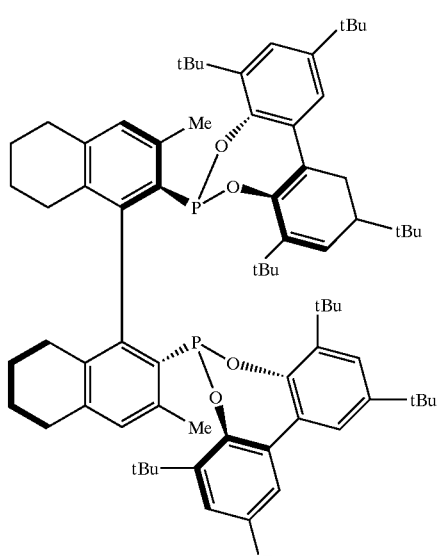
L282
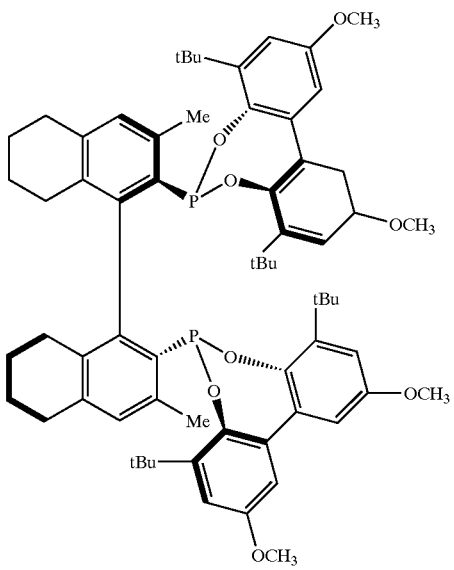
L283
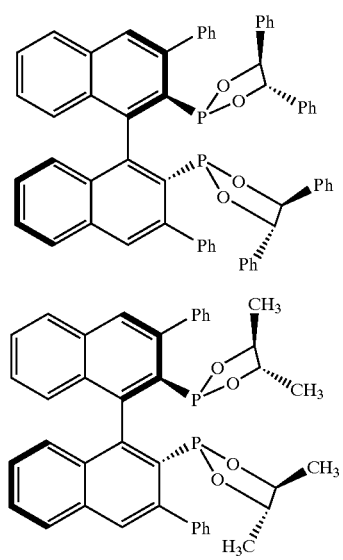
L284
L285
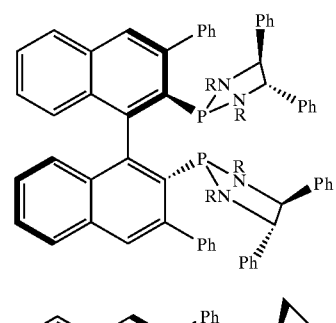
L286
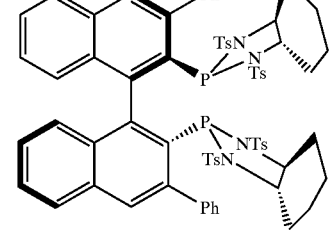

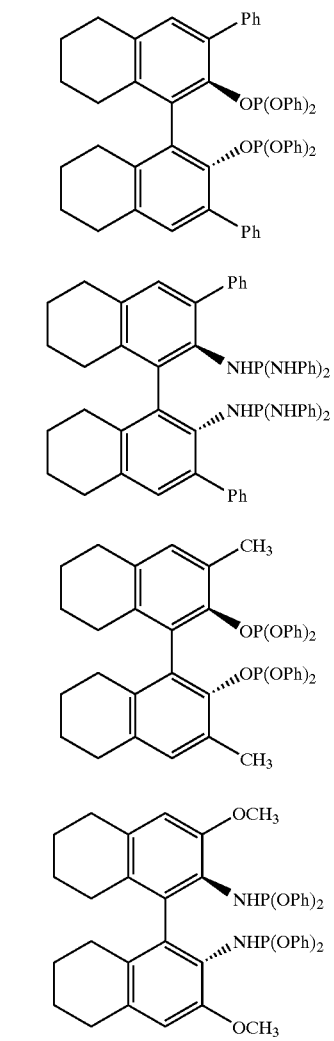
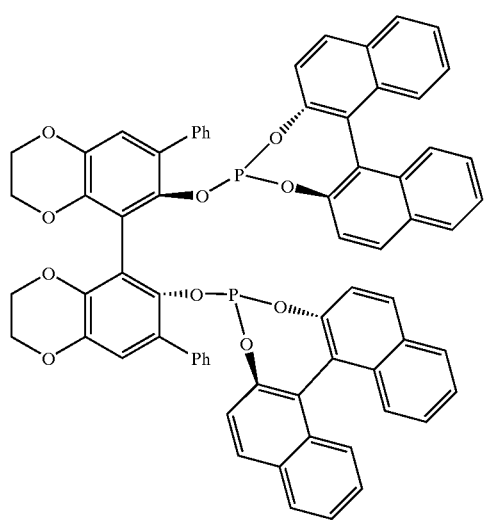

-continued

L304
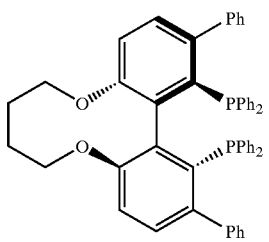
L305
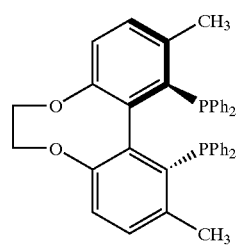
L306
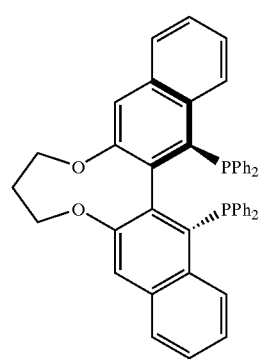
L307
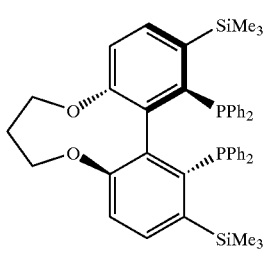
L308
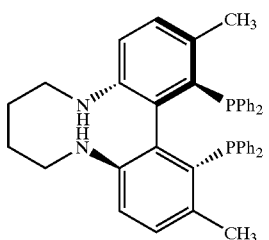
L309
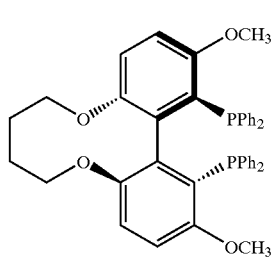
L310
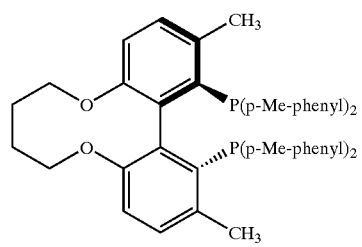
L312
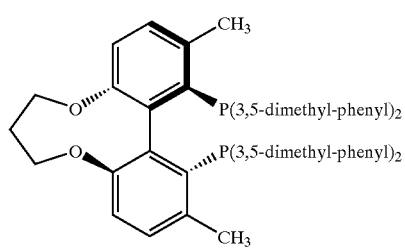
L313
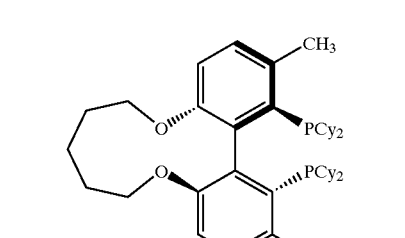
L314
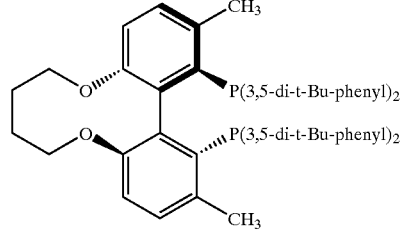
L315
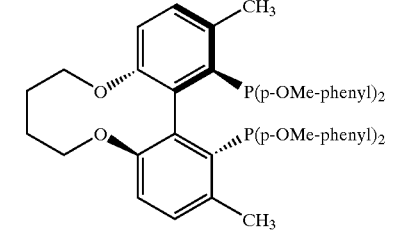
L316
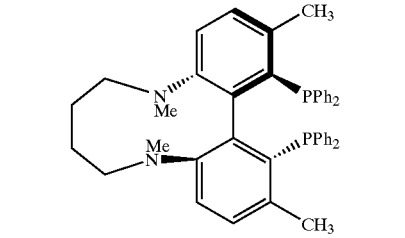

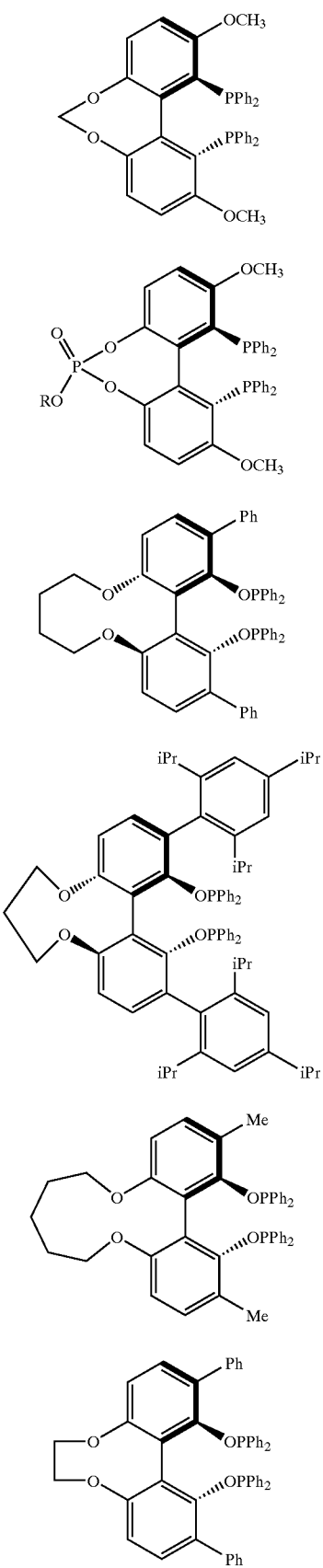
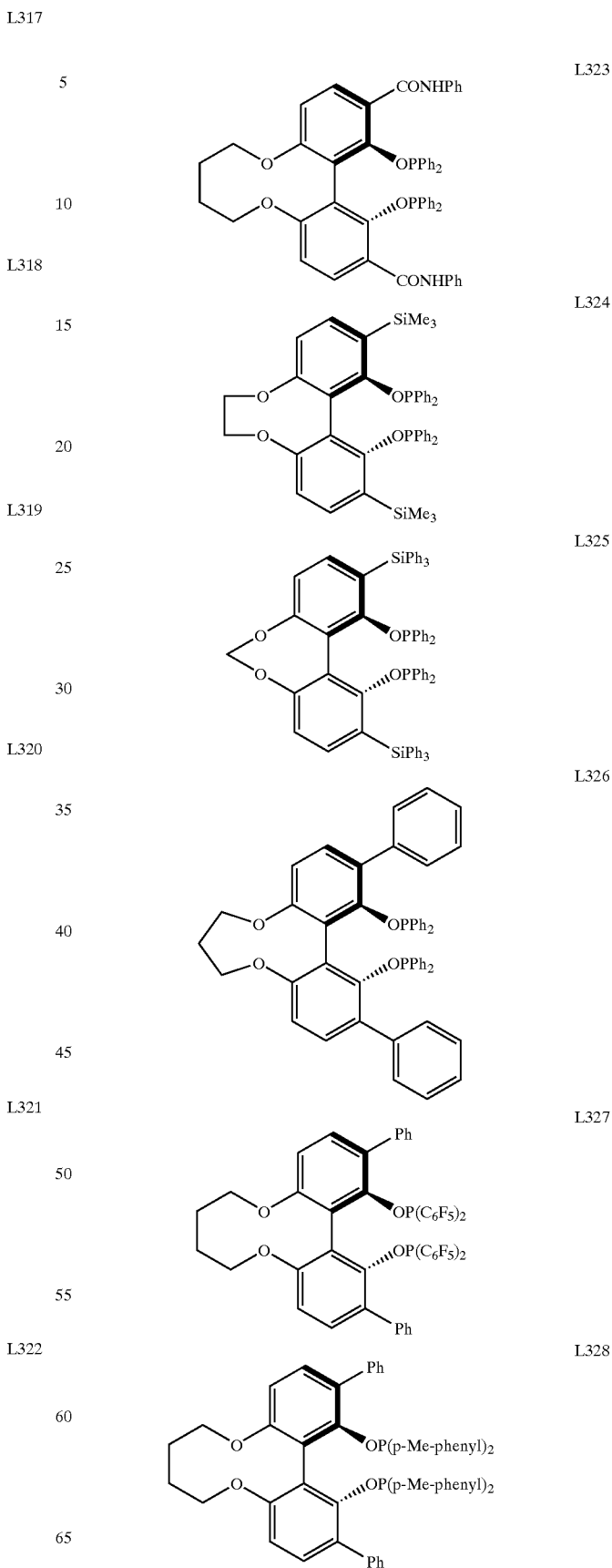

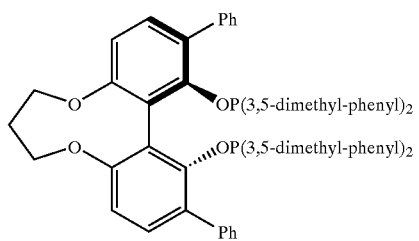
L329
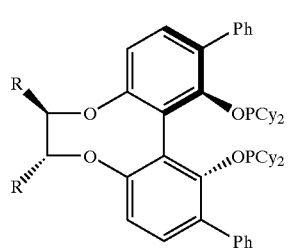
L330
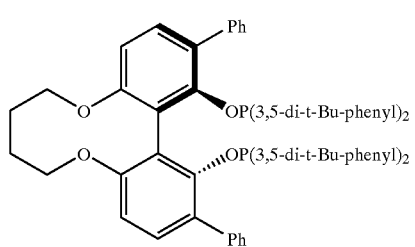
L331
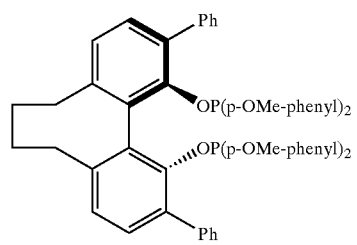
L332
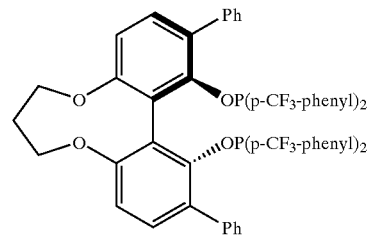
L333
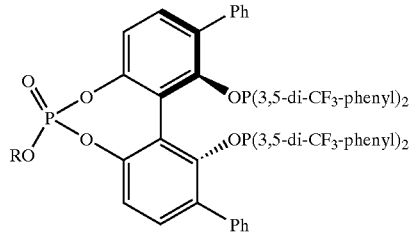
L334
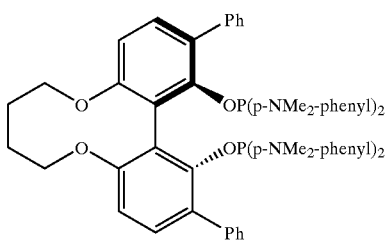
L335
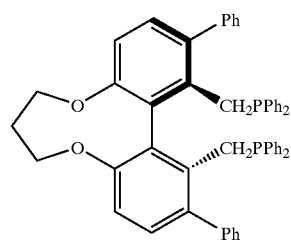
L336
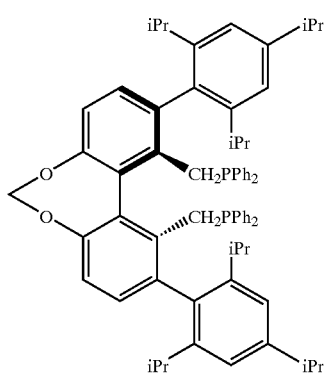
L337
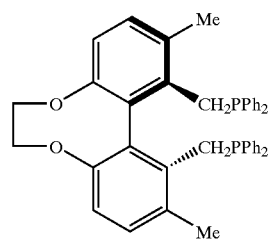
L338
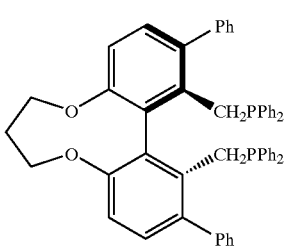
L339
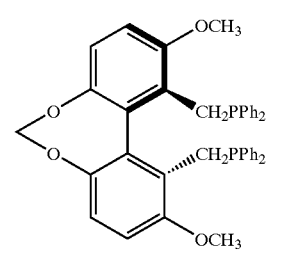
L340

-continued
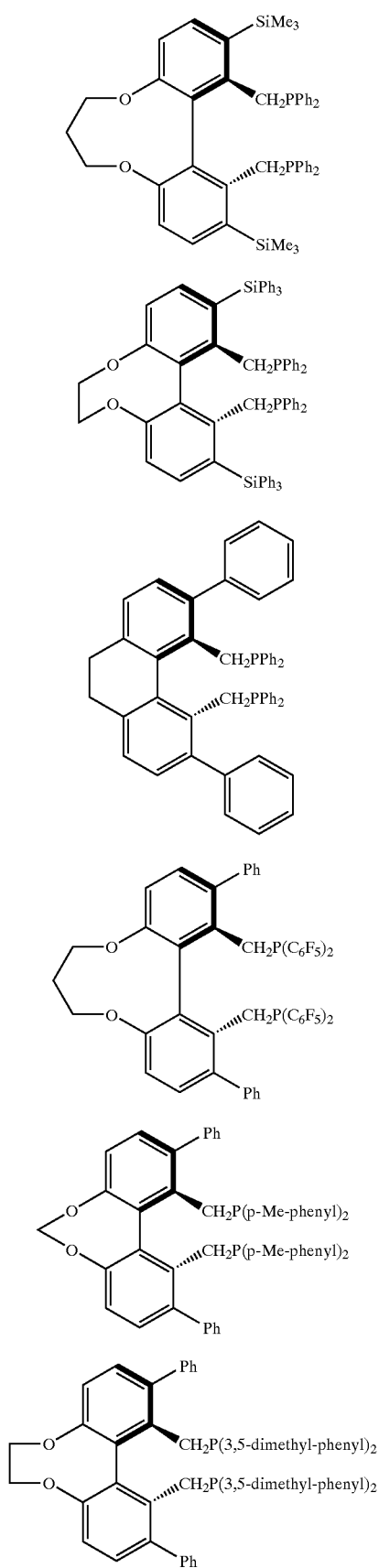
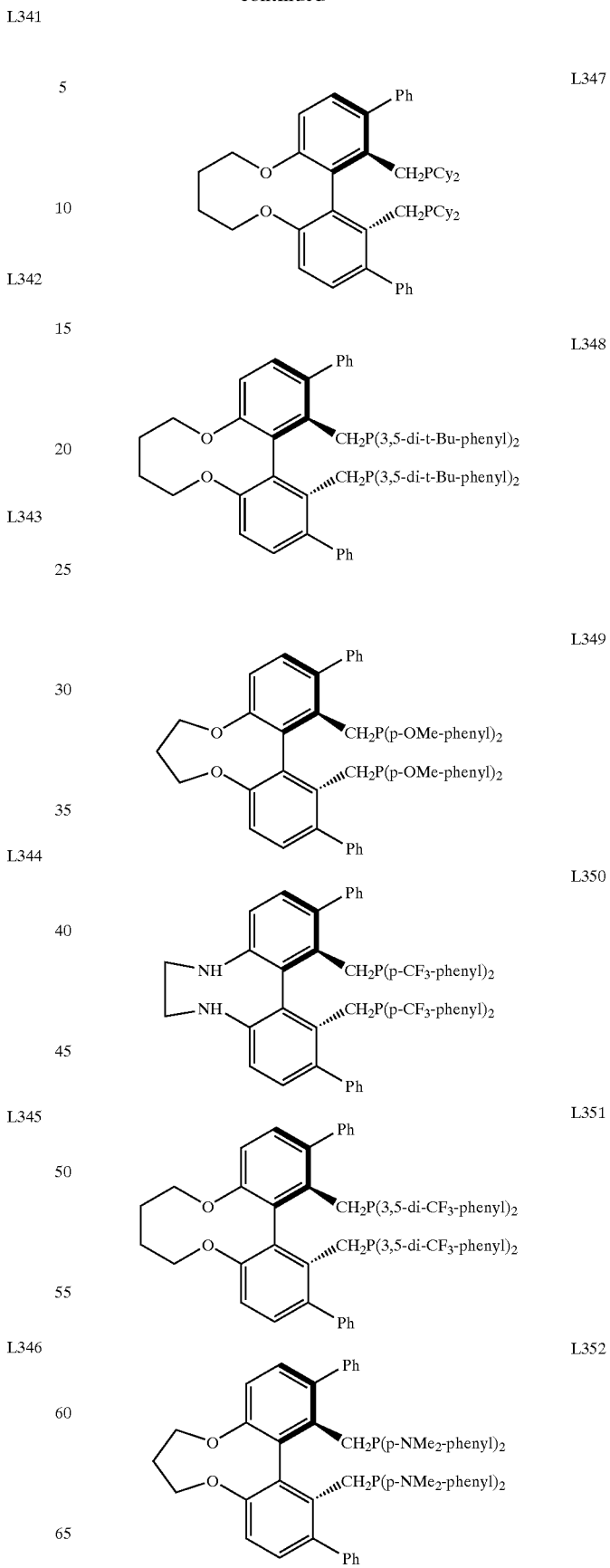

L353 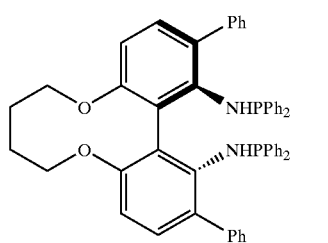
L354 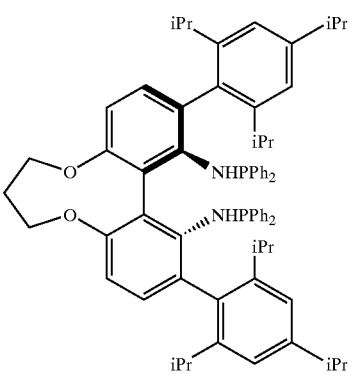
L355 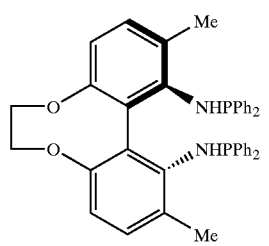
L356 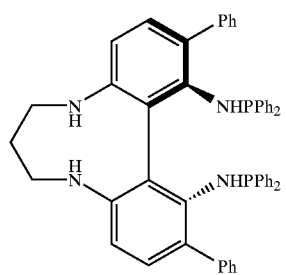
L357 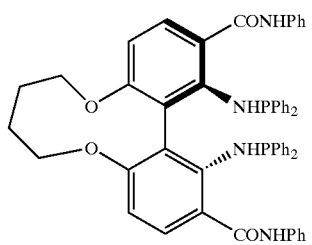
L358 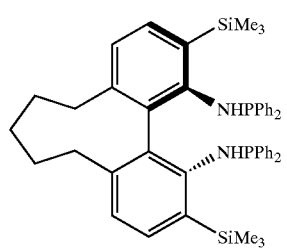
L359 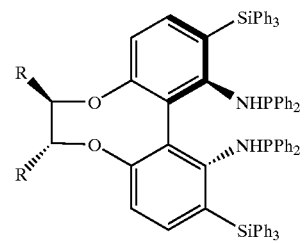
L360 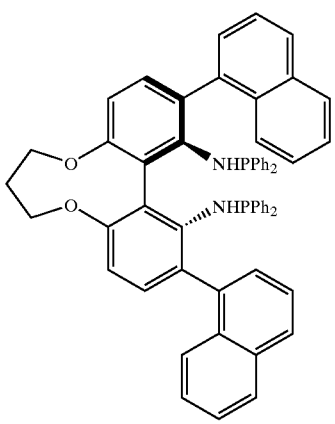
L361 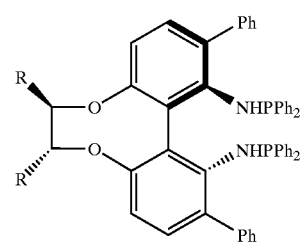
L362 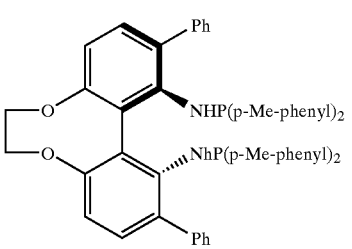
L363 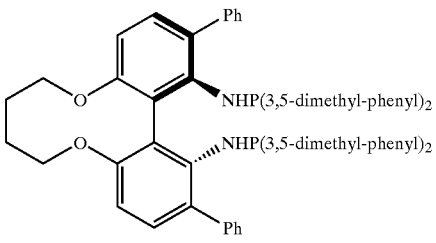
L364 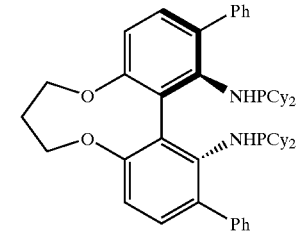

L365
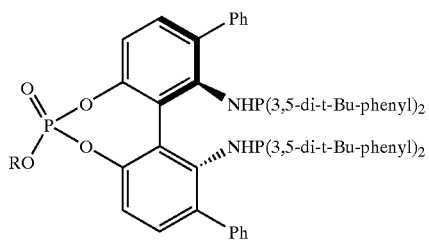
L366
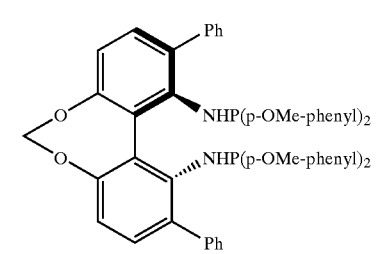
L367
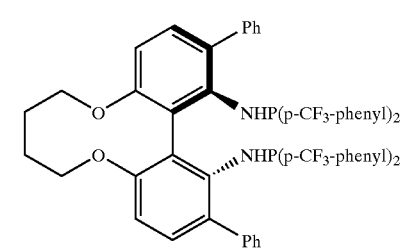
L368
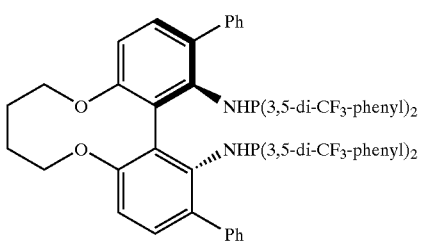
L369
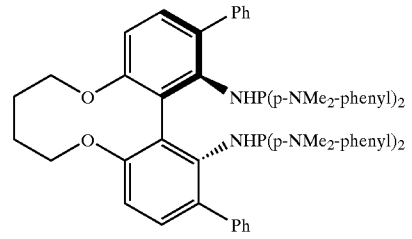
L370
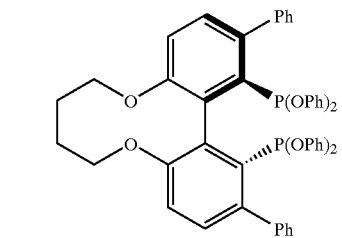
L371
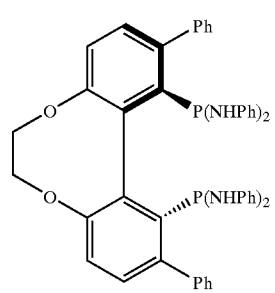
L372
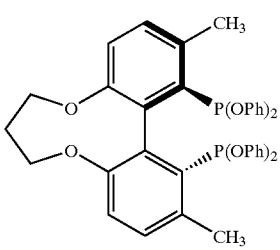
L373
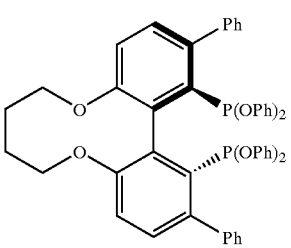
L374
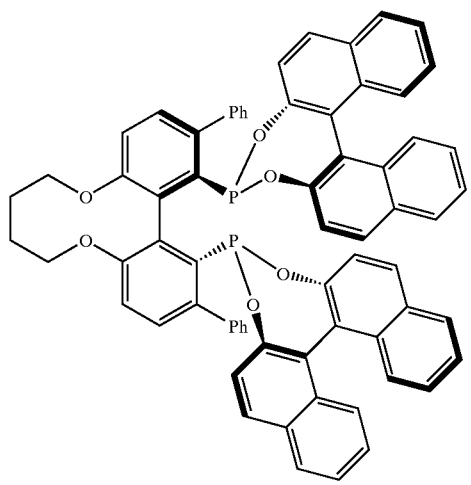

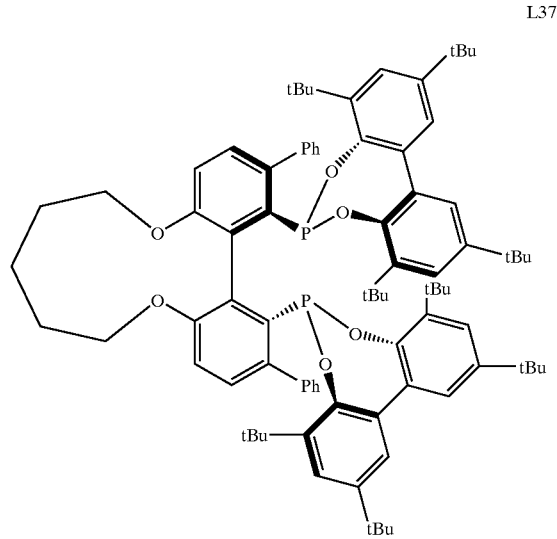
L375
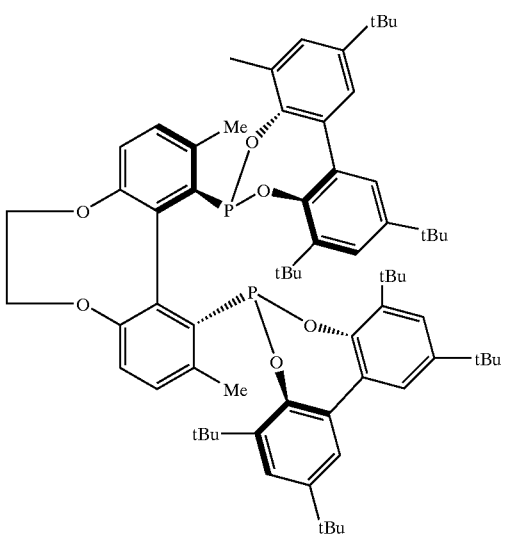
L378
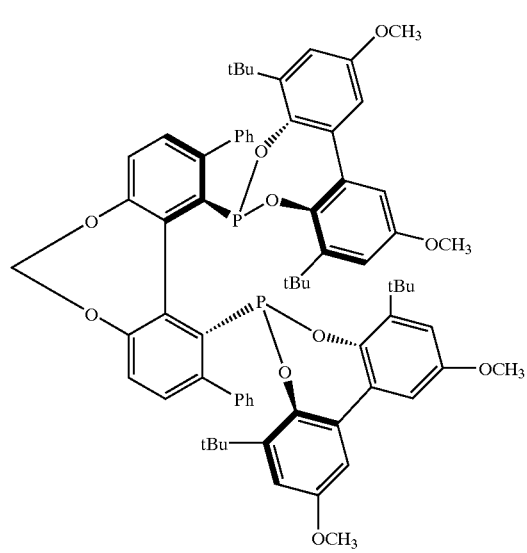
L376
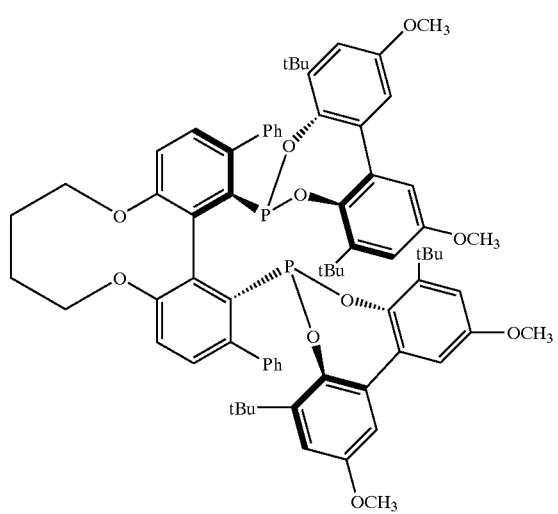
L379
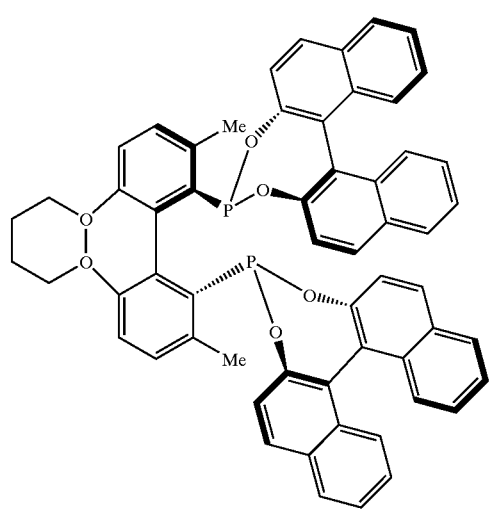
L377
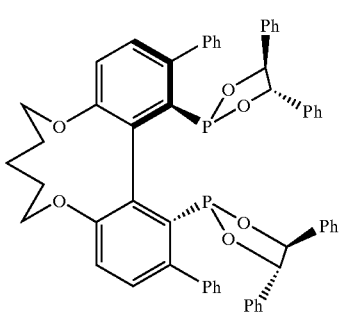
L380

-continued
L381
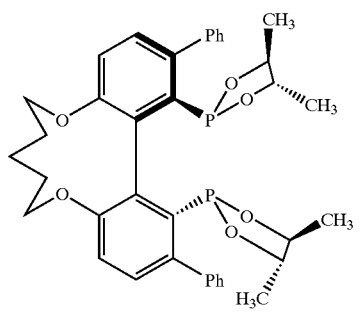
L382
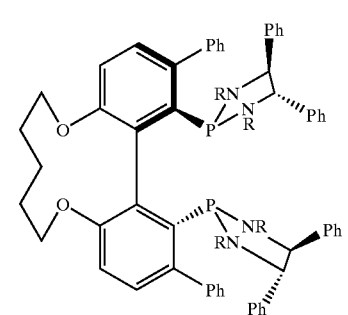
L383
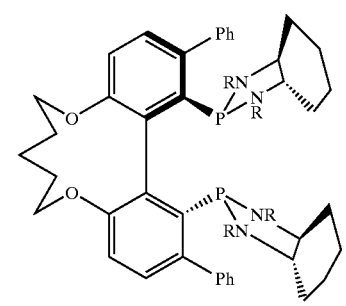
L384
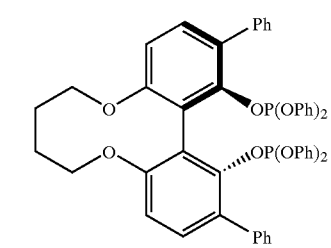
L385
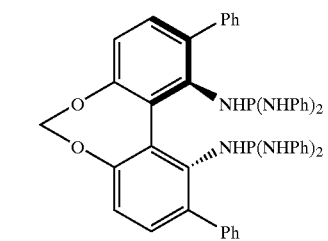
-continued
L386
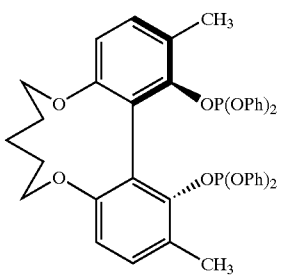
L387
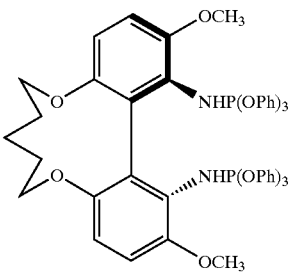
L388
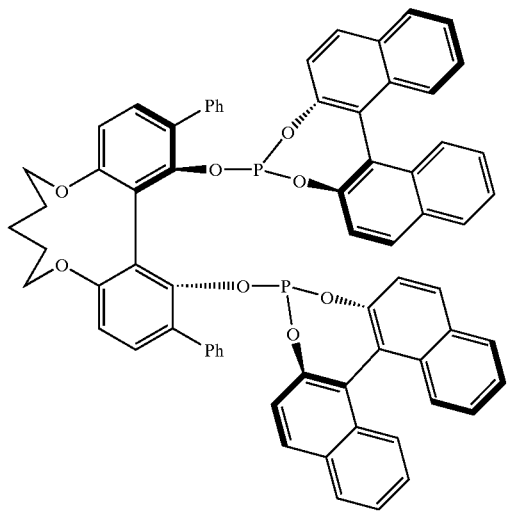
L389
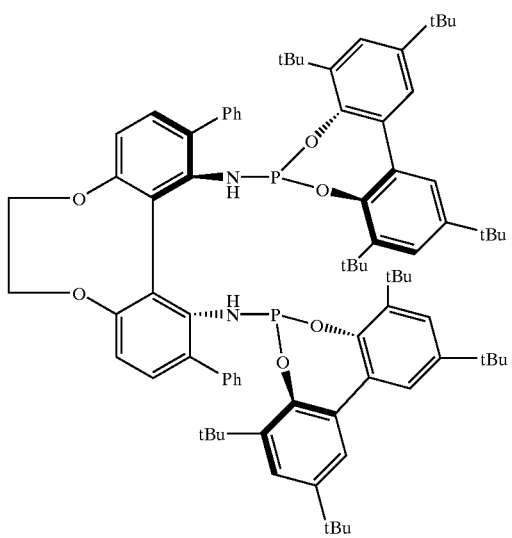

-continued
L390
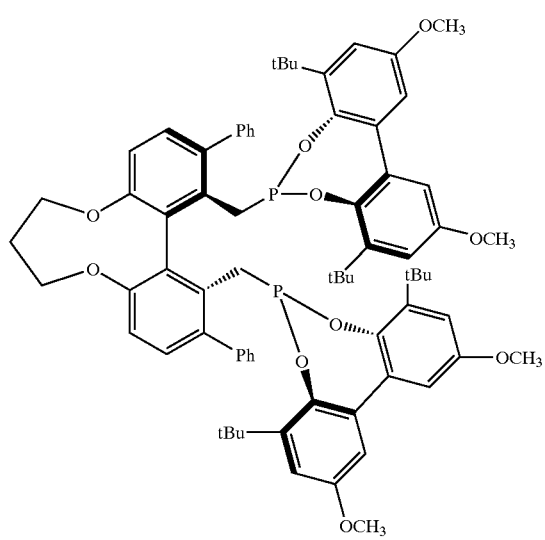
L391
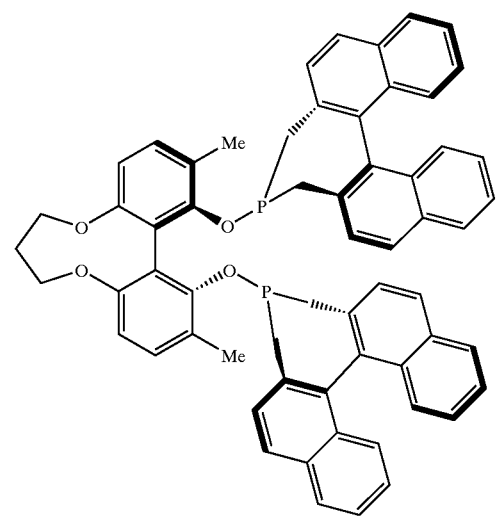
L392
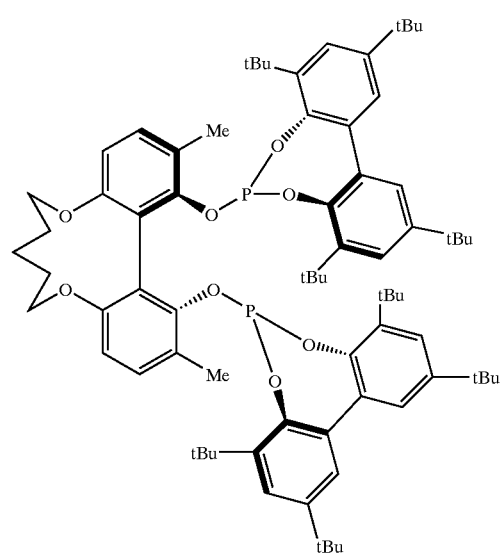
-continued
L393
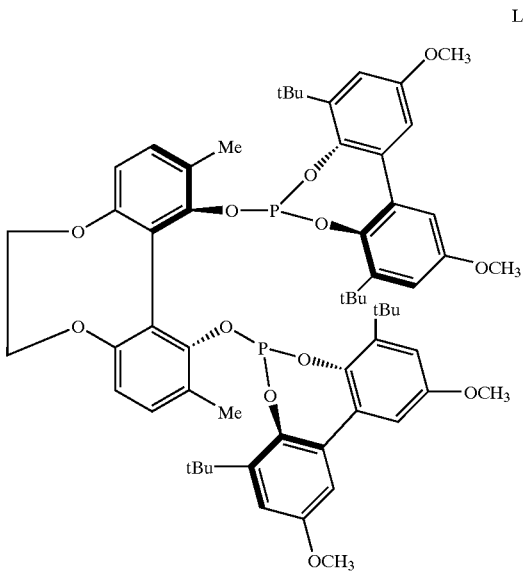
L394
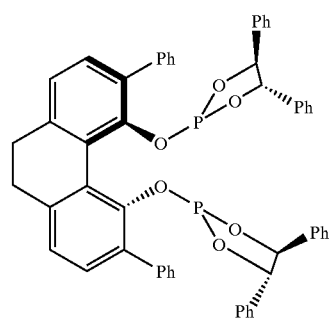
L395
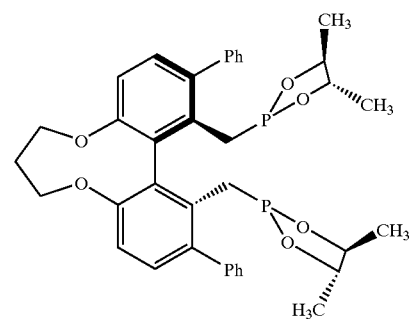
L396
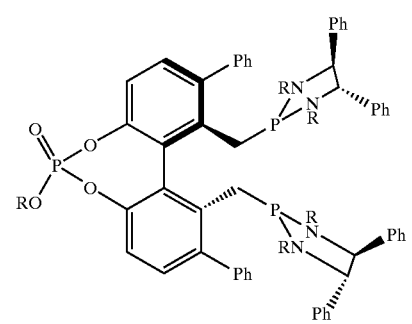

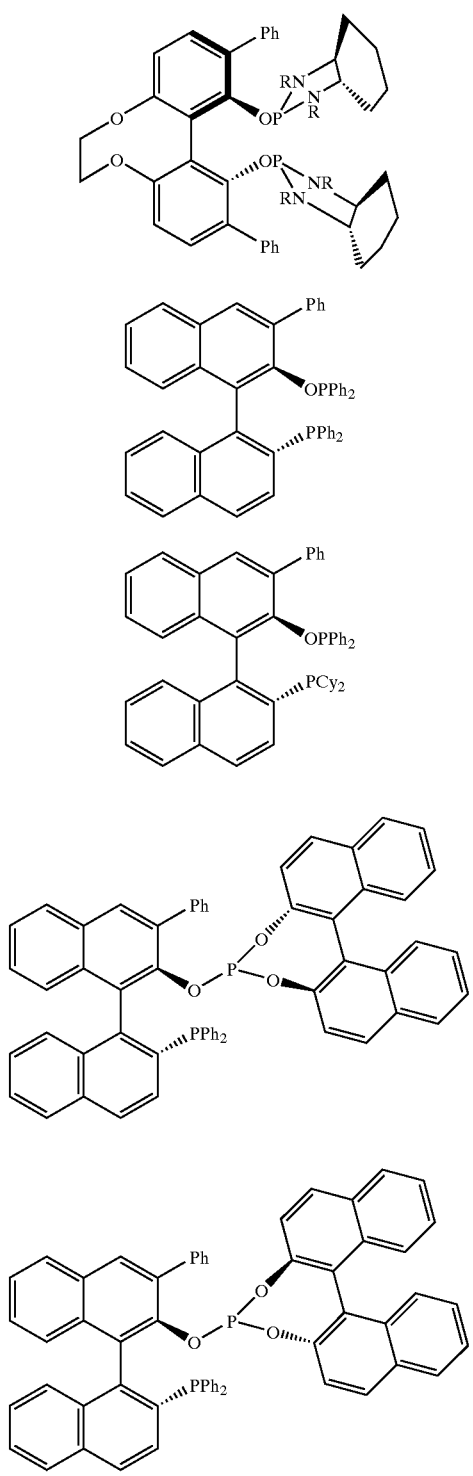

L397

L398

L399

L400

L401

The present invention also includes a catalyst prepared by a process comprising contacting a transition metal salt, or a complex thereof, and a ligand according to the present invention. The catalyst may be prepared in situ or as an isolated compound.

The catalyst of the present invention can be a racemic mixture of enantiomers. Preferably, the catalyst is a non-racemic mixture of enantiomers, and more preferably, the catalyst is one of the enantiomers. Preferably, the catalyst has an optical purity of at least 85% ee, and more preferably, the catalyst has an optical purity of at least 95% ee.

Suitable transition metals for the preparation of the catalyst include Ag, Pt, Pd Rh, Ru, Ir, Cu, Ni, Mo, Ti, V, Re and Mn.

As mentioned above, the catalyst can be prepared by contacting a transition metal salt or its complex and a ligand according to the present invention.

Suitable transition metal salts or complexes include the following:

AgX; Ag(OTf); Ag(OTf)$_2$; AgOAc; PtCl$_2$; H$_2$PtCl$_4$; Pd$_2$(DBA)$_3$; Pd(OAC)$_2$; PdCl$_2$(RCN)$_2$; (Pd(allyl)Cl)$_2$; Pd(PR$_3$)$_4$; (Rh(NBD)$_2$)X; (Rh (NBD)Cl)$_2$; (Rh(COD)Cl)$_2$; (Rh(COD)$_2$)X; Rh(acac)(CO)$_2$; Rh(ethylene)$_2$(acac); (Rh(ethylene)$_2$Cl)$_2$; RhCl(PPh$_3$)$_3$; Rh(CO)$_2$Cl$_2$; RuHX(L)$_2$(diphosphine), RuX$_2$(L)$_2$ (diphosphine), Ru(arene)X$_2$(diphosphine), Ru(aryl group)X$_2$; Ru(RCOO)$_2$(diphosphine); Ru(methallyl)2 (diphosphine); Ru(aryl group)X$_2$(PPh$_3$)$_3$; Ru(COD)(COT); Ru(COD)(COT)X; RuX$_2$(cymen); Ru(COD)$_n$; Ru(aryl group)X$_2$(diphosphine); RuCl$_2$(COD); (Ru(COD)$_2$)X; RuX$_2$(diphosphine); RuCl$_2$(=CHR)(PR'$_3$)$_2$; Ru(ArH)Cl$_2$; Ru(COD)(methallyl)$_2$; (Ir(NBD)$_2$Cl)$_2$; (Ir(NBD)$_2$)X; (Ir(COD)$_2$Cl)$_2$; (Ir(COD)$_2$)X; CuX (NCCH$_3$)$_4$; Cu(OTf); Cu(OTf)$_2$; Cu(Ar)X; CuX; Ni(acac)$_2$; NiX$_2$; (Ni(allyl)X)$_2$; Ni(COD)$_2$; MoO$_2$(acac)$_2$; Ti(OiPr)$_4$; VO(acac)$_2$; MeReO$_3$; MnX$_2$ and Mn(acac)$_2$; wherein each R and R' is independently selected from the group consisting of: alkyl or aryl; Ar is an aryl group; and X is a counter-anion.

In the above transition metal salts and complexes, L is a solvent and the counteranion X can be halogen, BF$_4$, B(Ar)$_4$ wherein Ar is fluorophenyl or 3,5-di-trifluoromethyl-1-phenyl, ClO$_4$, SbF$_6$, PF$_6$, CF$_3$SO$_3$, RCOO or a mixture thereof.

In another aspect, the present invention includes a process for preparation of an asymmetric compound using the catalysts described above. The process includes the step of contacting a substrate capable of forming an asymmetric product by an asymmetric reaction and a catalyst according to the present invention prepared by contacting a transition metal salt, or a complex thereof, and a ligand according to the present invention.

Suitable asymmetric reactions include asymmetric hydrogenation, hydride transfer, allylic alkylation, i.e., palladium-catalyzed allylic alkylation of an allylic ester, hydrosilylation, hydroboration, hydrovinylation, hydroformylation, olefin metathesis, hydrocarboxylation, isomerization, cyclopropanation, Diels-Alder reaction, Heck reaction, isomerization, Aldol reaction, Michael addition; epoxidation, kinetic resolution, i.e., palladium-catalyzed allylic alkylation of a racemic allylic ester, and [m+n] cycloaddition wherein m=3 to 6 and n=2, i.e., silver-catalyzed asymmetric [3+2] cycloaddition of an azomethine ylide with a dipolarophile.

Preferably, the asymmetric reaction is hydrogenation and the substrate to be hydrogenated is an ethylenically unsaturated compound, imine, enamine, enamide, vinyl ester or a ketone, including a ketone such as a beta-ketoester.

In the case of beta-ketoesters and enamides, the use of Ru as the transition metal to produce an asymmetric beta-hydroxyester and beta amino acid, respectively, is preferred, particularly when the ligand is a compound represented by one of the following formulas:

(a)

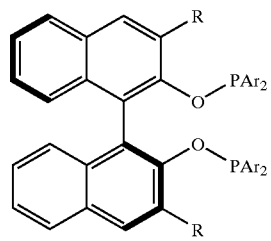

wherein each R is independently selected from the group consisting of: alkyl, aryl, substituted alkyl, substituted aryl and SiR$_3$; and wherein each Ar is independently selected from the group consisting of: phenyl, substituted phenyl, aryl and substituted aryl;

(b)

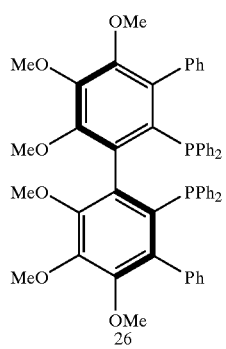

26

(c)

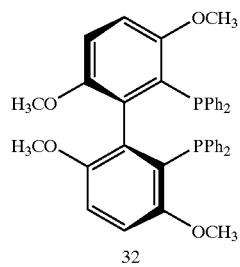

32

(d)

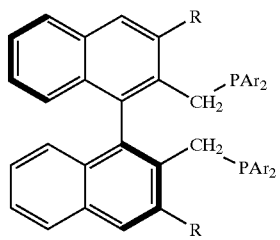

or a combination thereof.

The detailed description of ligand synthesis and asymmetric reactions thereof is provided below.

General Procedures

All reactions and manipulations were performed in a nitrogen-filled glove box or using standard Schlenk techniques. THF and toluene were dried and distilled from sodium-benzophenone ketyl under nitrogen. Methylene chloride was distilled from CaH$_2$. Methanol was distilled from Mg under nitrogen. (R, R)-BDNPB was made a solution of 10 mg/ml in toluene before use. Column chromatography was performed using EM silica gel 60 (230–400 mesh). $^1$H, $^{13}$C and $^{31}$P NMR were recorded on Bruker WP-200, AM-300, and AMX-360 spectrometers. Chemical shifts were reported in ppm down field from tetramethylsilane with the solvent resonance as the internal standard. Optical rotation was obtained on a Perkin-Elmer 241 polarimeter. MS spectra were recorded on a KRATOS mass spectrometer MS 9/50 for LR-EI and HR-EI. GC analysis was carried on Helwett-Packard 6890 gas chromatography using chiral capillary columns. HPLC analysis was carried on Waters™ 600 chromatography.

Ligand Synthesis

Ligand Synthesis

Several chiral ligands have been prepared and used for asymmetric hydrogenation reactions. Scheme 1 shows the synthesis of these ligands. The starting material, enantiomerically pure BINOL can be converted to many chiral phosphines and phosphinites (11a-L20, 11b-L18, 11c-L31, 11d and 15-L38). 3,3'-disubstituted BINOL was prepared from (S)-BINOL according to known literature methods (Cox, P. J. et al. *Tetrahedron Lett.* 1992, 33, 2253; Simonsen, K. B. et al. *J. Org. Chem.* 1998, 63, 7536).

Scheme 1
Ligand Synthesis

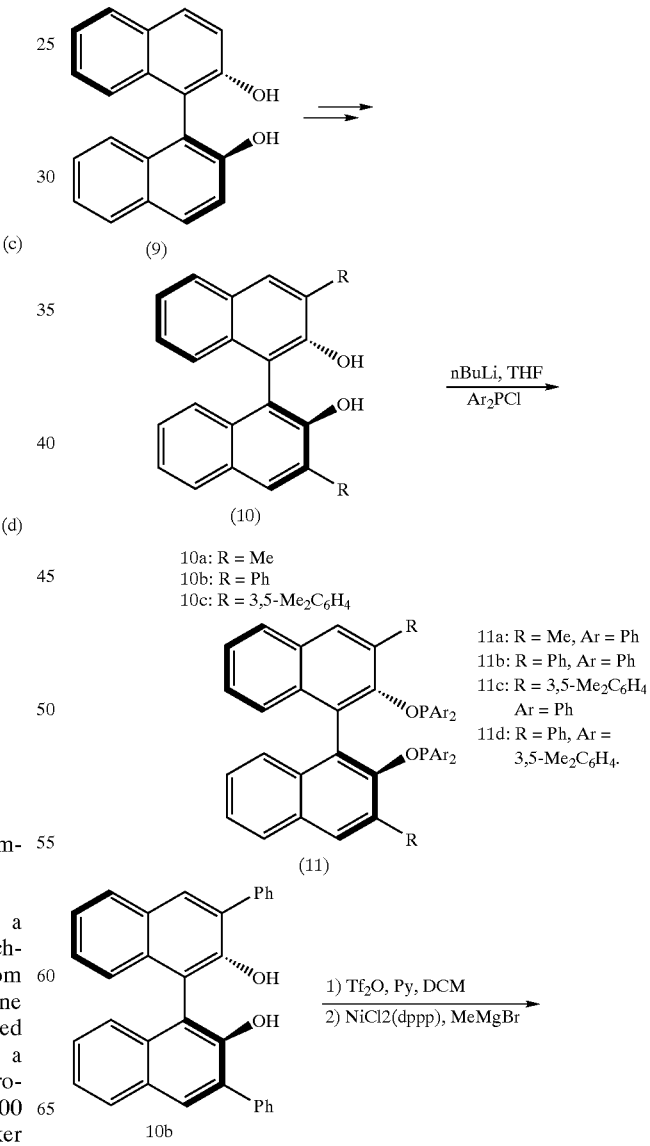

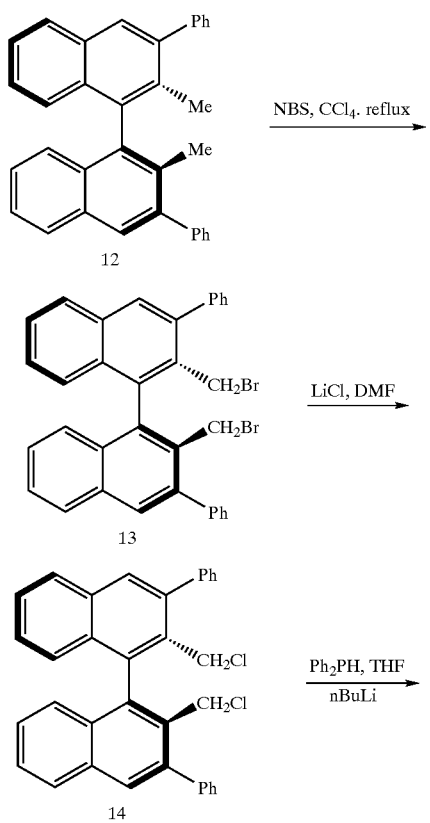

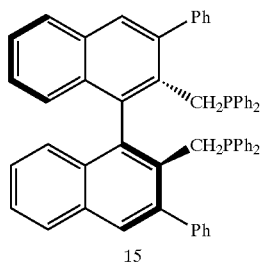

Chiral bisphosphinite ligands (11a-L20, 11b-L18, 11c-L31, 11d) were made through reaction of chlorodiaryl phosphine with the corresponding chiral diols (10a–10c) in high yields. Chiral bisphosphine 15 was made from 3,3'-diphenyl-2,3'dihydroxyl-1,1'-binaphthyl (10b) in a few steps. Compounds 12–14 were synthesized according to a reported procedure (Xiao, D. et al. *Org. Lett.* 1999, 1, 1679). Representative examples can be synthesized by a variety of methods. Several such methods suitable for use in the synthesis of chiral 3,3'disubstituted bisaryl phosphines, are described below:

Examples of Ligand Synthesis

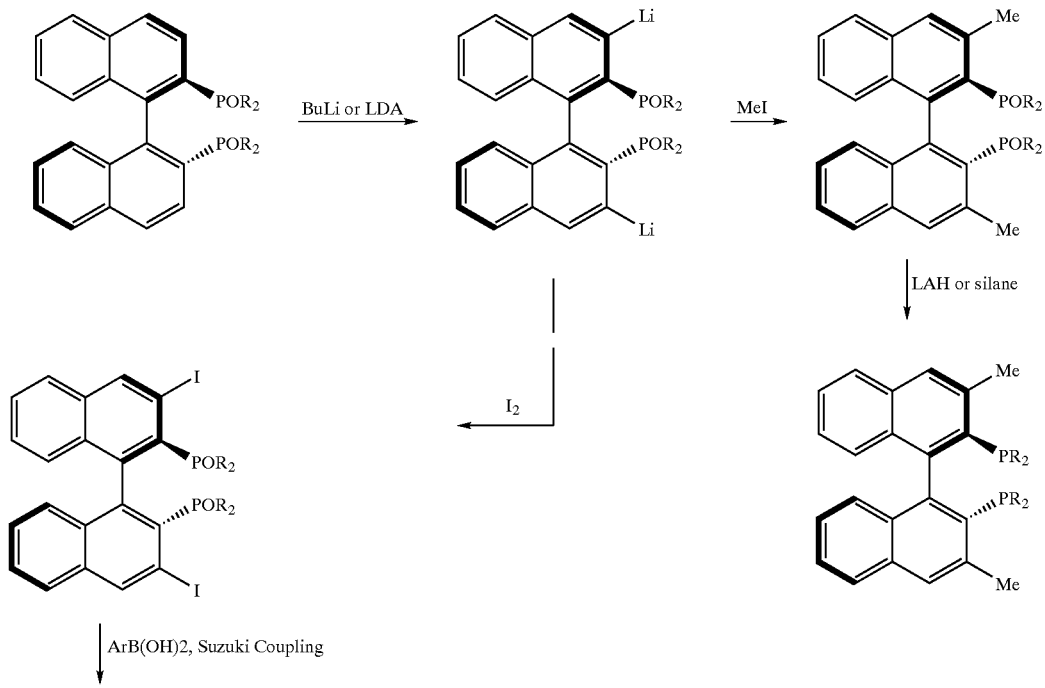

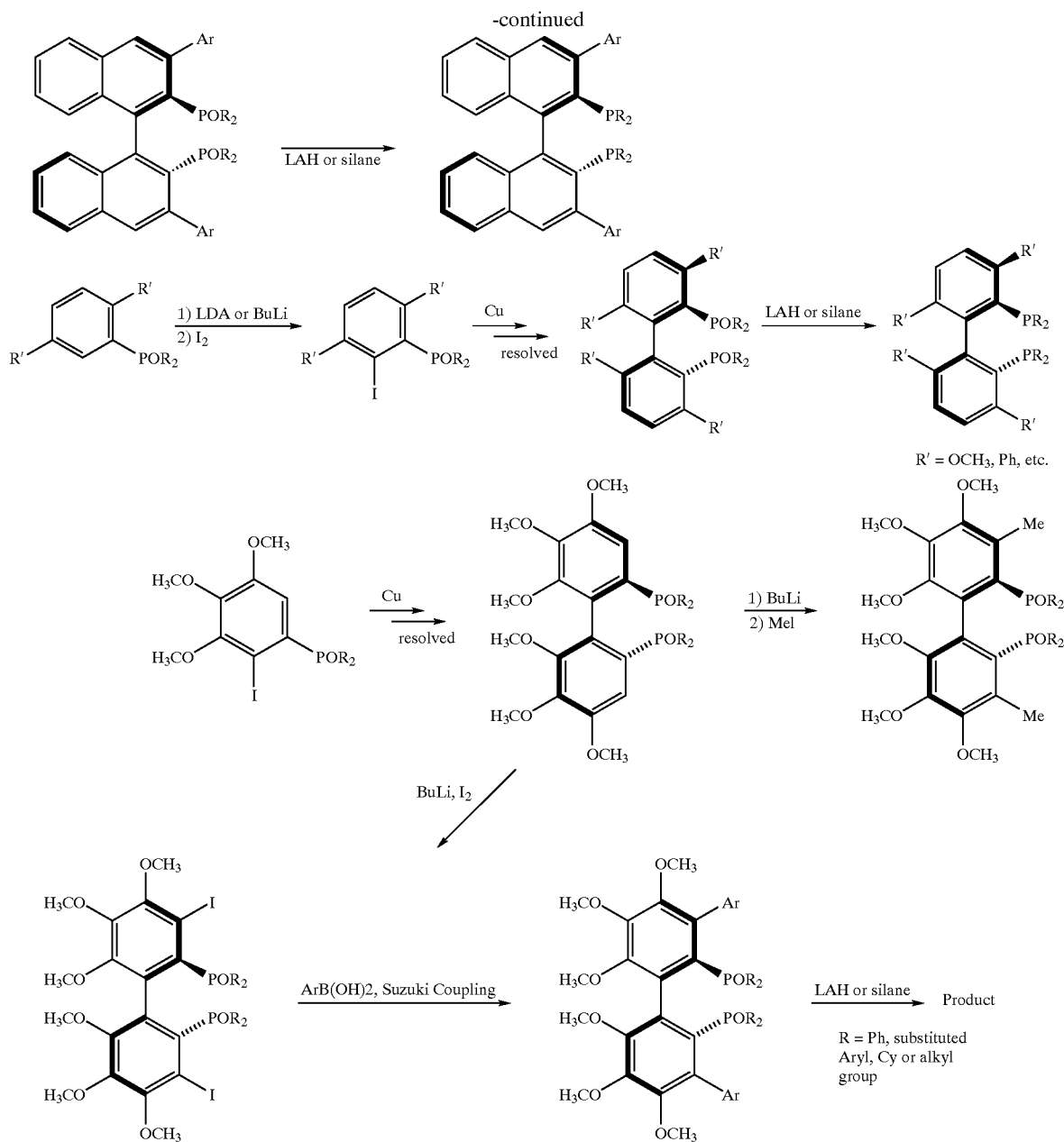

EXAMPLE 1

Synthesis of a 3,3'-Disubstituted Chiral BINOL (10b)

(R)-2,2-'-Bismethoxymethoxy-1,1'-binaphthyl

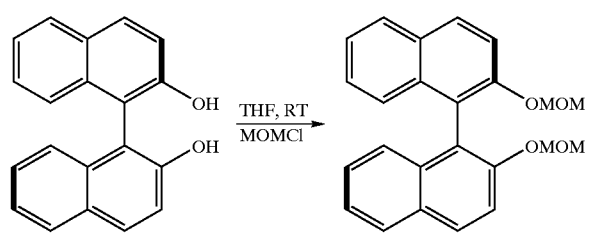

To a THF (200 ml) solution of NaH (5.52 g, 230 mmol) was added (R)-BINOL (28.6 g, 100 mmol) solution in THF (50 ml) under nitrogen at zero temperature, after 30 min, chloromethyl methyl ether (17.09 ml, 225 mmol) in 30 ml THF was added dropwise. The mixture was stirred overnight at room temperature. 3 ml water was added carefully to destroy the excess NaH, and filtered to remove the inorganic salt. The solution was passed a silica gel plug (hexane/ethyl acetate=1/1) to give pure product (97% yield).

(R)-3,3-'-diodo-2,2'-Bismethoxymethoxy-1,1'-binaphthyl

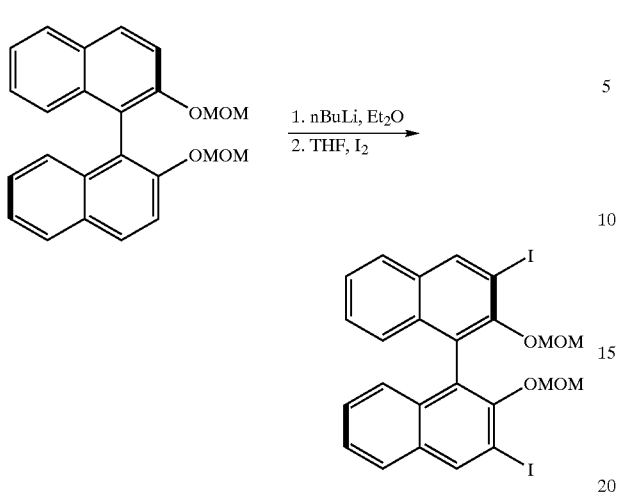

To a solution of (R)-2,2'-Bismethoxymethoxy-1,1'-binaphthyl (37.4 g, 100 mmol) in diethyl ether (400 ml) was added n-BuLi (100 ml, 2.5 M in hexane, 250 mmol) at room temperature under nitrogen, the mixture was stirred for 3 hours, then was cooled to 0° C., 200 ml THF was added, after 10 min, a solution of iodine (300 mol, 76.2 g) in THF (60 ml) was added dropwise. The mixture was allowed to warm to room temperature over 4 hours. 100 ml saturated $Na_2SO_3$ aqueous was added to destroy the excess iodine, then extracted with ethyl acetate, organic phase was washed with 100 ml saturated $Na_2SO_3$, 3×100 ml water, dried over sodium sulfate and evaporated. The residue was purified by a silica gel column eluted with (hexane/ethyl acetate=7/1) to give product as a yellow solid (80% yield, contain 5–7% monoiodo-substituted product).

(R)-3,3'-diphenyl-2,2-'-Bismethoxymethoxy-1,1'-binaphthyl

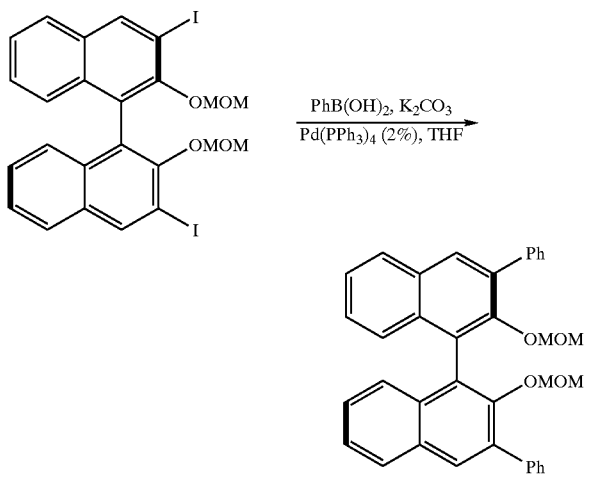

To a solution of (R)-3,3'-diiodo-2,2'-Bismethoxymethoxy-1,1'-binaphthyl (90 mmol, 56.3 g) and phenylboronic acid (25.2 g, 225 mmol) in THF 800 ml, was added Pd(PPh$_3$)$_4$ (2.3 g, 2 mmol) and degassed 1M $K_2CO_3$ aqueous solution (400 ml, 400 mmol). The reaction mixture was heated at reflux for 20 hours. The mixture was extracted with ethyl acetate, and combined organic layer was washed with brine. Evaporation of the solvent gave a yellow solid (47 g). The residue was used to next step without other purification.

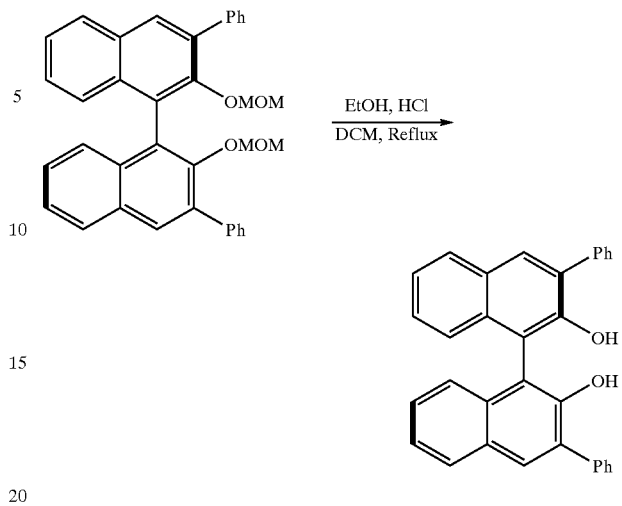

(R)-3,3'-diphenyl-1,1'-binaphthol

To a solution of (R)-3,3'-diphenyl-2,2'-Bismethoxymethoxy-1,1'binaphthyl (47 g) in a mixture solvent of 200 ml DCM and 500 ml EtOH was added concentrated HCl (90 ml). The reaction mixture was heated at reflux under nitrogen for 16 hours. The volatile components were removed under reduced pressure, and the residue was purified by column chromatography on silica gel (DCM/hexanes=4/6) to give the product (25.2 g, 57.6 mmol, 64% yield for two steps)

EXAMPLE 2

Alternative Route for the Synthesis of a 3,3'-Disubstituted Chiral BINOL (10b)

(S)-2,2'-Dimethoxy-1,1'-dinaphthyl

To a solution of (S)-2,2'-dihydroxy-1,1'-dinaphthyl (100 g, 349.7 mmol) in 1000 ml 95% EtOH was added dimethyl sulfate (93.1 ml, 981.7 mmol, 2.8 eq.) and followed by dropwise addition of a solution of NaOH (175 g) in 300 ml $H_2O$. After the addition, the resulting system was heated to reflux for 3 h, and then cooled. The reaction mixture was filtered, the precipitate was collected and washed with 10% aqueous NaOH (3×150 ml), and recrystallized from toluene (reflux to dissolve into 700 ml toluene, then let it stay at 0° C. overnight) to yield 84.1 g white crystal product (S)-2,2'-dimethoxy-1,1'-dinaphthyl (yield=76.6%). $^1$H-NMR (CDCl$_3$):δ7.985(d, J=9.0 Hz, 2H, Ar-H), 7.875(d, J=8.1 Hz, 2H, Ar—H), 7.468(d, J=9.0 Hz, 2H, Ar—H), 7.300~7.326(t, 2H, Ar—H), 7.199~7.218(t, 2H, Ar—H), 7.118(d, J=8.1 Hz, 2H, Ar—H), 3.773(s, 6H, —OCH$_3$).

(S)-3,3'-Bis(dihydroxyborane)-2,2'-Dimethoxy-1,1'-dinaphthyl

Under $N_2$, in a 500 ml Schlenk flask were placed 300 ml of dry t-butyl-methyl ether and TMEDA (14.4 ml, 95.5 mmol, 3 equiv). To this solution was added 2.5M n-BuLi in hexane(39.5 ml, 98.7 mmol, 3.1 equiv), the resulting solution was stirred for 30 min. at room temperature, solid (S)-2,2'-dimethoxy-1,1'-dinaphthyl (100 g, 31.8 mmol) was added in one portion under $N_2$ flow, the reaction system was stirred at room temperature for 3 hrs. The resulting brown slurry was cooled to −78° C., and B(OEt)$_3$ (33.9 ml, 197.5 mmol, 6.2 equiv) was dropwise introduced over a period of 15 min. The reaction system was allowed to warm room temperature and was left stirring overnight. The reaction was quenched with 150 ml aqueous 1M HCl solution, and was stirred for another 2 h. The phase was separated, the organic phase was washed with aqueous 1M HCl solution (3×100 mL) and saturated aqueous NaCl solution (3×100 ml), and dried over Na$_2$SO$_4$. The solvent was removed, and the resulting white solid were recrystallized twice from 70 ml toluene (reflux to dissolve into 700 ml toluene, then let it stay at 0° C. overnight, and recrystallization once can't remove by-product completely) to give the product (S)-3,3'-Bis(dihydroxyborane)-2,2'-Dimethoxy-1,1'-dinaphthyl 9.33 g (Yield =73.3%). $^1$H-NMR(Acetone-d$_6$):δ 8.556(s, 2H, Ar—H), 8.041(d, J=8.1 Hz, 2H, Ar—H), 7.454(t, 2H, Ar—H), 7.335(t, 2H, Ar—H), 7.112(d, J=8.1 Hz, 2H, Ar—H), 3.773(s, 6H, —OCH$_3$). $^1$H-NMR shows that toluene is very difficult to remove completely, but there is no any influence on the secondary reaction.

(S)-3,3'-Diphenyl-2,2'-dimethoxy-1,1'-dinaphthyl

In a 50 ml Schlenk flask were placed (S)-3,3'-bis(dihydroxyborane)-2,2'-dimethoxy-1,1'-dinaphthyl(1.206 g, 3 mmol), Ba(OH)$_2$.8H$_2$O (2.739 g, 8.7 mmol, 2.9 equiv), and Pd(PPh$_3$)$_4$ (183 mg, 0.15 mmol, 5% mol), the reaction system was evacuated and filled with N$_2$ for three times, 1,4-dioxane(18 ml), H$_2$O(8 ml), and bromobenzen(1.89 ml, 18 mmol, 6 eq.) were added. The reaction system was heated under reflux for 24 hrs under N$_2$ and cooled to room temperature. The 1,4-dioxane was removed, and the resulting mixture was redissolved into 100 ml CH$_2$Cl$_2$, and washed with aqueous 1M HCl solution (3×50 ml) and saturated aqueous NaCl solution(2×50 ml), and dried over Na$_2$SO$_4$. The solvent was removed to yield crude product (S)-3,3'-diphenyl-2,2'-dimethoxy-1,1'-dinaphthyl 1.513 g as orange G 5 syrup.

This intermediate was not isolated and was used directly in the final step.

(S)-3,3'-Diphenyl-2,2'-dihydroxy-1,1'-dinaphthyl (10b)

The crude product diphenyl-2,2'-dimethoxy-1,1'-dinaphthyl (1.513 g, approximately 3 mmol) was dissolved into 80 ml dry CH$_2$Cl$_2$, and cooled to −78° C., BBr$_3$(1.5 ml) was added in 10 min., and the reaction system was stirred for 18 h at room temperature. The resulting slight brown solution was cooled to 0° C., and 200 ml H$_2$O was added carefully. The phase was separated, and the organic phase was washed with H$_2$O (5×80 ml) and saturated aqueous NaCl solution (2×50 ml), and dried over Na$_2$SO$_4$. The solvent was removed, and the resulting solid was recrystallized from 10 ml MeOH to yield (S)-10b as white-gray powder (overall yield of coupling and deprotection steps, 61.8%).

$^1$H-NMR(CDCl$_3$):δ8.029(s, 2H, Ar—H), 7.929(d, J=7.9 Hz, 2H, Ar—H), 7.741(dd, 4H, J=7.9 1.4 Hz Ar—H), 7.499(t, 4H, Ar—H), 7.376~7.434 (m, 4H, Ar—H), 7.325 (td, 2H, J=7.9 1.3 Hz Ar—H), 7.250(t, 2H, Ar—H), 5.364 (br, 2H, —OH).

EXAMPLE 3

Synthesis of a 3,3'-Disubstituted Chiral Phosphinite, (R)-3,3'-diphenyl-2,2'-bisdiphenylphosphinooxy-1,1'-binaphthyl (11b)

To a solution of (R)-3,3'-diphenyl-1,1'-binaphthol (876 mg, 2 mmol) in 20 ml THF at −78° C. was added n-BuLi (2.8 ml, 4.5 mmol) dropwise, the mixture was warmed to room temperature and stirred for 30 min, then cooled to −78° C., Ph$_2$PCl (0.9 ml, 5 mmol) was added via syringe, then warmed to room temperature and stirred overnight. The THF was removed under reduced pressure, the residue was purified by basic Al$_2$O$_3$ (EtOAc/Hexane/Et$_3$N=90/8/2) to give pure product (1.41 g, 87% yield).

$^1$H-NMR (CD$_2$Cl$_2$, 360 MHz) 6.80–7.20 (m, 24H), 7.35–7.48 (m, 12H), 7.50–7.65 (m, 4H).). $^{31}$P-NMR (CD$_2$Cl$_2$, 360 MHz) 112.78.). $^{13}$C-NMR (CD$_2$Cl$_2$, 360 MHz) 124–150 (m). [α]$_D^{20}$=114.7 (c, 0.38, CHCl$_3$). MS: 203 (100), 387 (65), 439 (48), 807 (50). HRMS C$_{56}$H$_{41}$O$_2$P$_2$ 807.2566 Cal.: 807.2582.

EXAMPLE 4

General Procedure for Catalytic Asymmetric Hydrogenation of Enamides

In a glove box, the Rh-phosphine complex was made in situ by mixing Rh(COD)$_2$PF$_6$ (3.7 mg, 0.008 mmol) and a chiral phosphine ligand (0.8 ml of 10 mg/mL ligand in toluene, 0.012 mmol) in 19.2 ml of CH$_2$Cl$_2$. The mixture was stirred for 30 min. Then 2.5 ml of this solution was transferred to a 10 ml vial with an enamide substrate (0.1 mmol).

The hydrogenation was performed at room temperature under 20 psi of hydrogen pressure for 24 h. The hydrogen was released carefully and the reaction mixture was passed through a silica gel plug eluted with EtOAc. The enantiomeric excess was measured by GC or HPLC using a chiral GC or HPLC column without further purification. The absolute configuration of products was determined by comparing the sign of optical rotation with the reported data.

EXAMPLE 5

Results of Asymmetric Hydrogenation of Enamides

To examine the effectiveness of new chiral ligands, hydrogenation of a typical dehydroamino acid derivative and an enamide was carried out. The results are summarized in Table 1. The 3,3'disubstituted bisphosphinite ligands (11a–d) are more effective than BINAPO (3) for asymmetric hydrogenation.

In the similar way, the 3,3'-disubstituted bisphosphine 15 is a better ligand for Rh-catalyzed asymmetric hydrogenation than NAPHOS (6).

We conclude that introduction of 3,3' substituted groups can restrict the rotation of phenyl groups adjacent to phosphines and therefore a well-defined chiral pocket around the transition metal is formed. The conformational rigidity is crucial for achieving high enantioselectivity for a number of asymmetric reactions.

TABLE 1

Rh(I)-catalyzed asymmetric hydrogenation

| Ligand | Substrate CH2=C(NHAc)COOMe | Substrate CH2=C(NHAc)Ph |
|---|---|---|
| entry 1: BINAPO 3 | 73% ee | 28% ee |
| entry 2: 11a | 95% ee | 67% ee |
| entry 3: 11b | >99% ee | 94% ee |
| entry 4: 11C | 95% ee | 89% ee |
| entry 5: 11d | 93% ee | 90% ee |

TABLE 1-continued

Rh(I)-catalyzed asymmetric hydrogenation

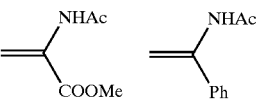

| Ligand | Substrate (NHAc, COOMe) | Substrate (NHAc, Ph) |
|---|---|---|
| entry 6 — NAPHOS 6 | 54% ee | — |
| entry 7 — 15 | 99% ee | 82% ee |

The reaction was carried out at rt under 3 atm of H2 for 12 h in 3 ml of THF with complete conversion (S/C = 100). Ar = 3,5-Me$_2$C$_6$H$_4$

EXAMPLE 6
Asymmetric Hydrogenation of Beta-Keto Esters

A number of beta-ketoesters can be reduced in high ee's using a Ru-3,3'substituted BINAPO (11d) compound as the catalysts. Particularly, the R group is aryl, hetereoaryl, substituted aryl, alkyl and substituted alkyl species. These reactions can be carried out at low pressure and low temperature, which shows advantages over the reaction carried out with Ru-BINAP complex (90 atm, 90° C.).

synthesized from cheap acetophenone in three steps according to known literature procedure in good yields. The literatures are Zhu, G.; Zhen, Z.; Zhang, X. *J. Org. Chem.* 1999, 64, 6907–6910; Krapcho, A. P.; Diamanti, J. *Org. Synth.* 1973,5, 198–201. $^1$H-NMR (CDCl$_3$, 360 MHz) δ (Z isomer) 2.17 (s, 3H), 3.77 (s, 3H), 5.29 (s, 1H), 7.37–7.45 (m, 5H); (E isomer) 2.38 (s, 3H), 3.77 (s, 3H), 6.65 (s, 1H), 7.37–7.45 (m, 5H).

Asymmetric Hydrogenation

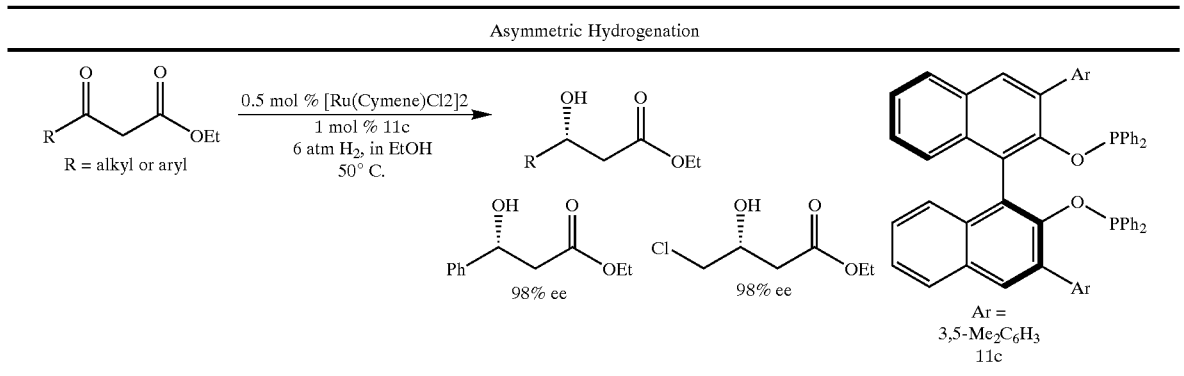

EXAMPLE 7
Asymmetric Synthesis of Beta-Amino Acids

Synthesis of Starting Material 3-Acetamido-3-Aryl-2-Propenoates and 3-Acetamido-3-hetero-Aryl-2-Propenoates Typical procedure: The starting material methyl 3-acetamido-3-phenyl-2-propenoate can be conveniently An Effective New Way to Make Enamides

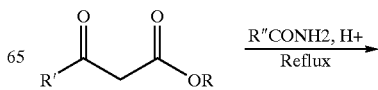

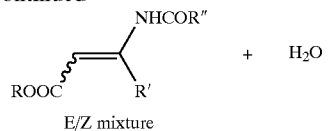

E/Z mixture

Alternatively, 3-acetamido-3-aryl-2-propenoates and 3-Acetamido-3-hetero-aryl-2-propenoates can be prepared through a new route by reacting acetamide with the corresponding beta-keto esters. A related example is demonstrated by Tschaen et al. *J. Org. Chem* 1995, 60, 4324. The typical procedure involves addition of the corresponding beta keto-ester, an acetamide or other amide such as enamide, Amberlyst 15 or other acid catalysts in toluene. The mixture was heated at reflux for some hours with removal of water using a Dean-Stark trap. The end product was obtained after evaporating the solvent.

Asymmetric Hydrogenation of methyl 3-acetamido-3-phenyl-2-propenoate

A dry Schlenk tube is charged with [Ru(cymene)Cl$_2$]$_2$ (1.53 mg, FW=612, 0.0025 mmol), chiral ligand 3,3'-diphenyl-xylyl BINAPO (11d, 4.82 mg, FW=918, 0.0053 mmol), and then is evacuated and filled with argon. DMF (must be degassed by freeze-thaw cycles) (1 ml) is introduced under stream of argon. The solution is stirred at 100° C. for 10 min under argon, giving a clear reddish brown solution. The reaction mixture is cooled and concentrated at 1 mmHg at 50° C. with vigorous stirring and then at 0.1 mmHg for 1 h to give a reddish brown solid, which is used as hydrogenation catalyst.

To a solution of above catalyst in EtOH/DCM (4 ml, 3/1) in a glove box was added substrate methyl 3-acetamido-3-phenyl-2-propenoate (109 mg, 0.5 mmol). The hydrogenation was performed at 50° C. under 78 psi of hydrogen for 15 hours (not be optimized). The bomb was then cooled to room temperature and hydrogen carefully released. The solvent was removed and the residue dissolved in ether. The ether solution was washed with water and brine and dried over sodium sulfate. The ether solution was passed through a short silica gel column and concentrated to dryness to give pure products methyl 3-acetamido-3-phenyl-2-propanoate (known compound, see: Zhu, G.; Zhen, Z.; Zhang, X. *J. Org. Chem.* 1999, 64, 6907–6910 (Rh/Duphos and BICP, 65% ee); Lubell, W. D.; Kitamura, M.; Noyori, R. *Tetrahedron: Asymmetry* 1991, 2, 543 (Ru/BINAP, poor ee)). $^1$H-NMR (CDCl$_3$, 360 MHz) δ 1.92 (s, 3H), 2.76–2.83 (m, 2H), 3.53 (s, 3H), 5.34 (m, 1H), 6.65 (br, 1H), 7.18–7.27 (m, 5H). Chiral GC Condition: Chiral Select-1000 column (dimensions 15 m×0.25 mm (i.d.)). Carrier gas: He (1 ml/min), 180° C., isothermal; (S) t$_1$=11.68 min; (R) t$_2$=12.04 min.

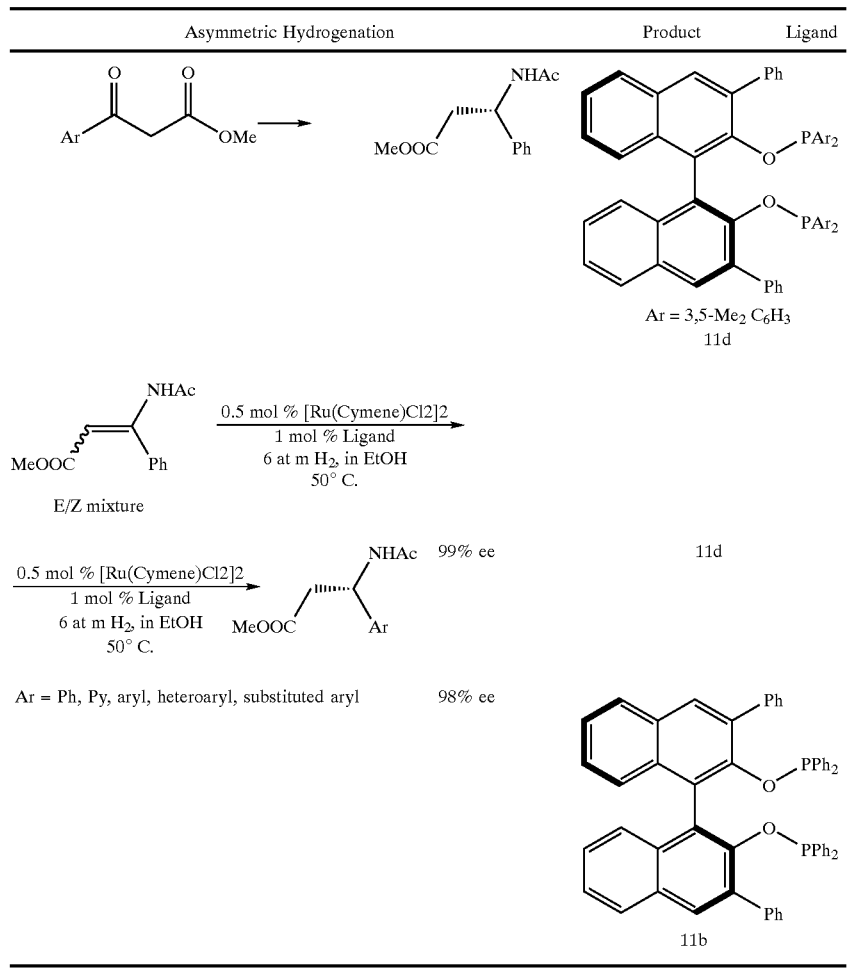

EXAMPLE 8

Asymmetric Allylic Alkylation

Using 3,3'disubstituted BINAPO as ligands, the Pd-catalyzed asymmetric allylic alkylation can be carried out and some results are listed below:

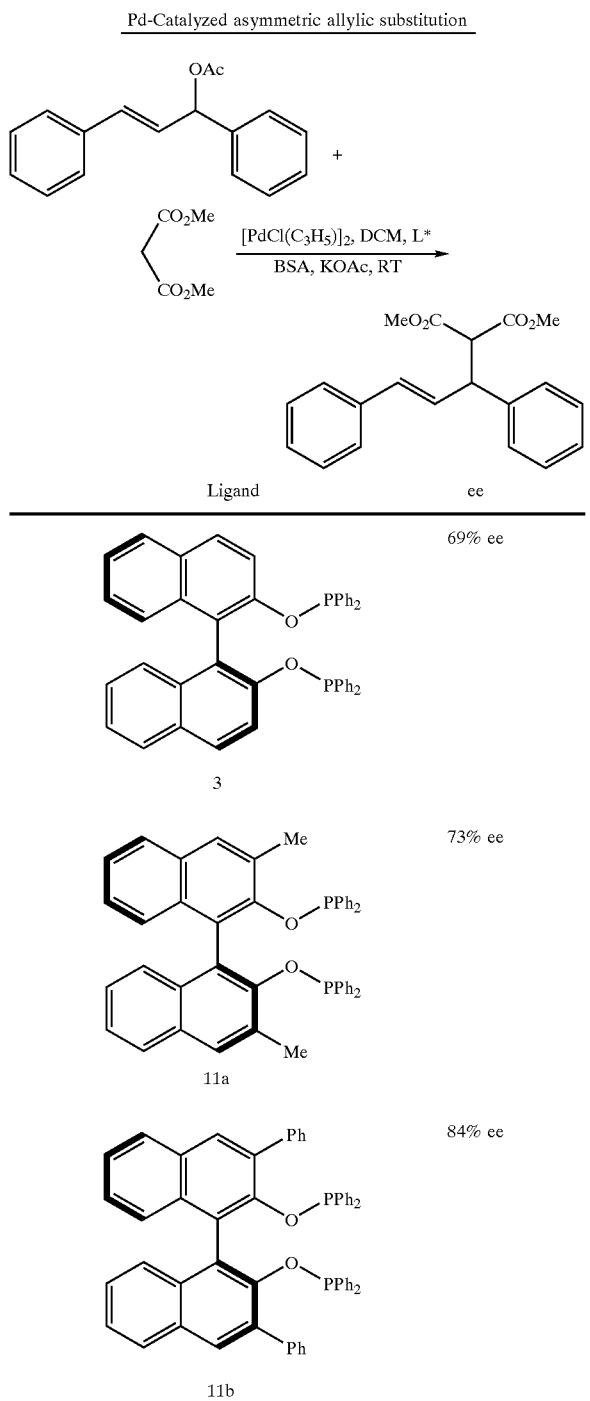

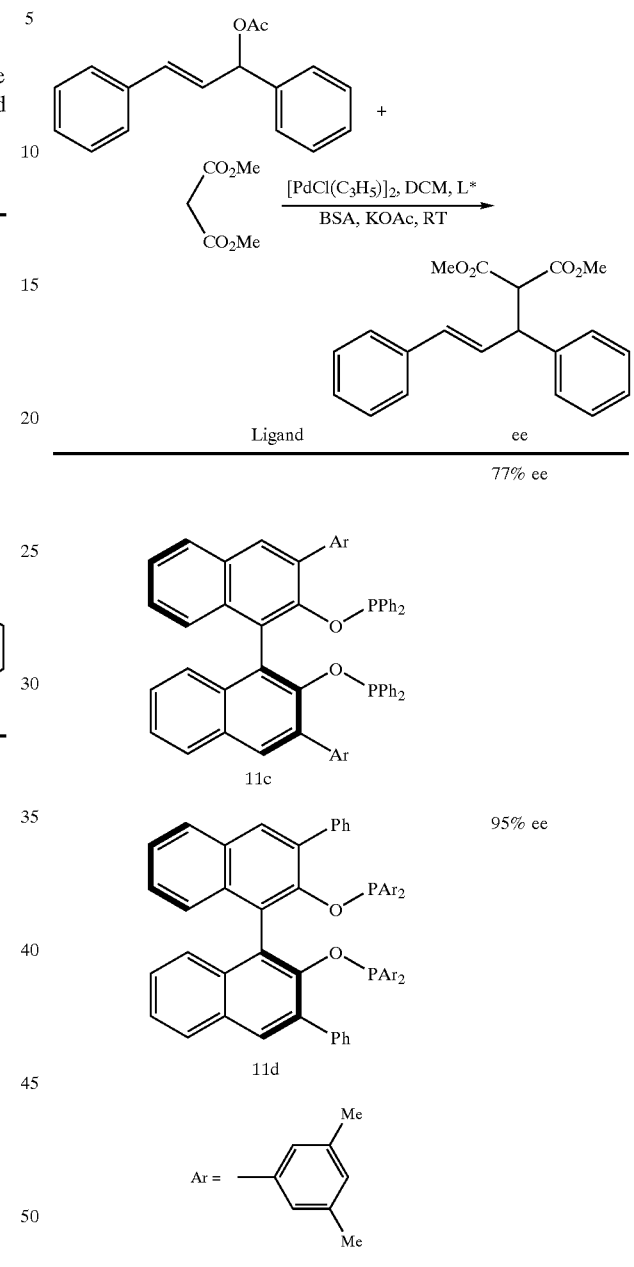

Ee values are determined by chiral HPLC (OJ Column H/IPA=95/5)

EXAMPLE 9

Asymmetric Allylic Alkylation with Nitrogen Nucleophile

Using 3,3'disubstituted BINAPO as ligands, Pd-catalyzed asymmetric allylic alkylation with nitrogen nucleophiles can be carried out and some results are listed below:

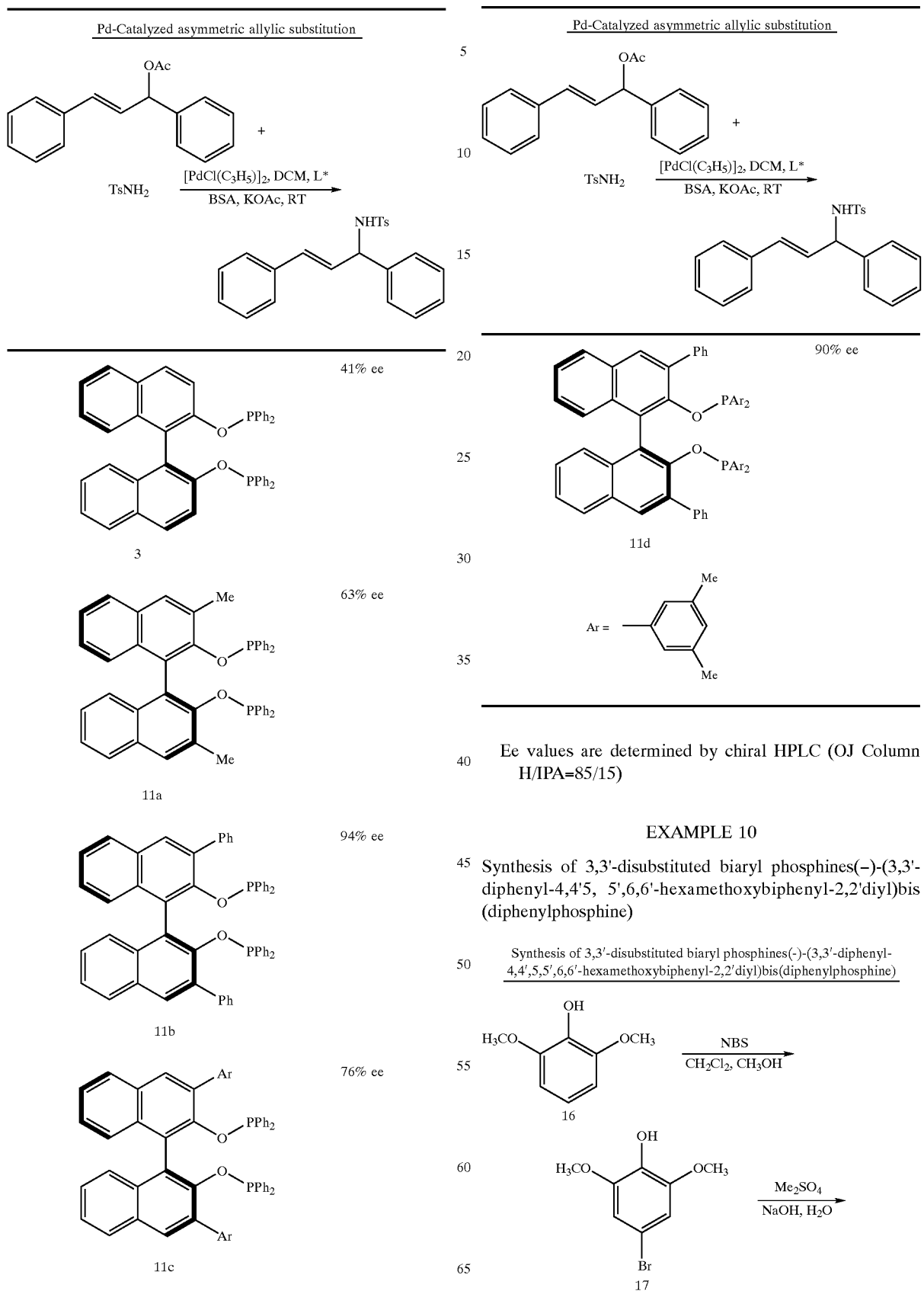
Ee values are determined by chiral HPLC (OJ Column H/IPA=85/15)
EXAMPLE 10
Synthesis of 3,3'-disubstituted biaryl phosphines(−)-(3,3'-diphenyl-4,4'5, 5',6,6'-hexamethoxybiphenyl-2,2'diyl)bis(diphenylphosphine)

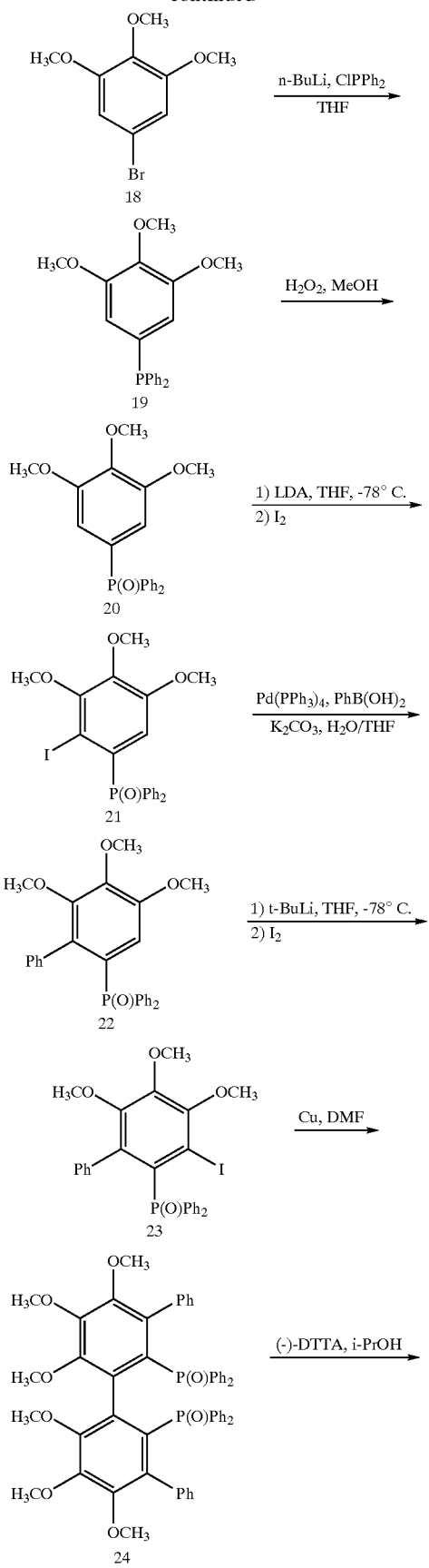

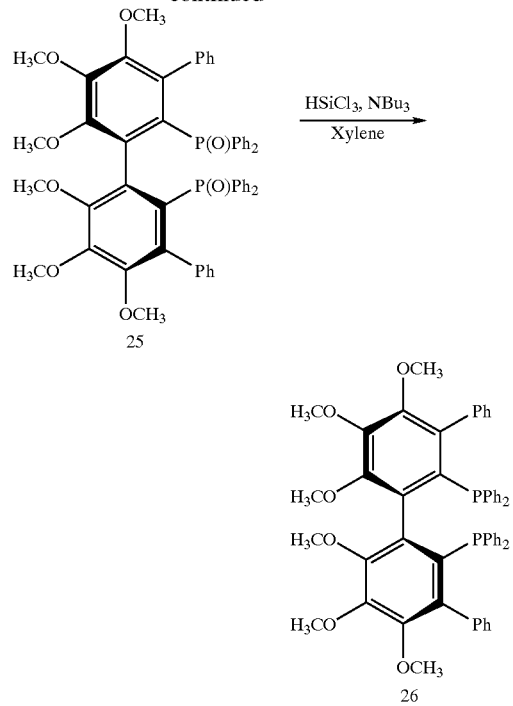

Synthesis of 4-bromo-2,6-dimethoxy-phenol 17

To a 2 liter flask equipped with a magnetic stirrer, thermometer, and nitrogen inlet, was added 77 g (0.5 mol) of pyrogallol 1,3-dimethyl ether, 5.8 ml of MeOH, and 750 ml of $CH_2Cl_2$. To this solution was added 126 mg (5 mmol) of NaH (95%). The solution was stirred while cooling to −45° C. with a dry-ice acetone bath. 94 g (0.53 mol) of powdered N-bromosuccinimide was added rapidly. The reaction mixture was then stirred for 1 hour at −35° C., heated to room temperature over next 30 min, and finally refluxed for 30 min. The $CH_2Cl_2$ was removed under reduced pressure and the residue solidified. The tan solid was broken up and stirred well with 1 liter of ether. This was filtered and the residue was washed well with ether. The ether was evaporated under reduced pressure to yield a tan solid. The solid was placed in a 5 liter flask with 3 liters of ligroin (bp: 90–110° C.) and heated with stirring to 80° C. The hot solution was decanted from the brown oil and the hot yellow solution was allowed to cool at room temperature for 3 hr. The white needles was filtered off and dried to yield 74 g (63%) of 17.

Ref. *J. Org. Chem. Vol.* 50, 1985, 1099.

Synthesis of 3,4,5-trimethoxybromobenzene 18

A mixture of 74 g (0.32 mol) of 4-bromo-2,6-dimethoxy-phenol 17 and 32 g (0.8 mol) of NaOH in 850 ml of $H_2O$ was cooled to 10° C. and 45 ml (0.48 mmol) of dimethyl sulfate was added. The mixture was refluxed for 3 h and an equal amount of dimethyl sulfate (total 0.96 mol) was then added. The mixture was refluxed for another 3 h. Upon cooling overnight, the gray product solidified and was filtered off and dissolved in 1.2 l of ether. The ether solution was filtered to remove insoluble impurity and washed sequentially with 5% NaOH solution (200 ml), water (2×200 mL), and brine (200 mL). The ether phase was dried over $Na_2SO_4$ to give a off-white solid, which was recrystallized in hexane (300 ml) to give 62.3 g (79%) of 18.

Synthesis of (3,4,5-trimethoxyphenyl)diphenylphosphine 19

To a solution of 3,4,5-trimethoxybromobenzene 18 (62.3 g, 0.25 mol) in dry THF (200 ml) was added BuLi solution (169 ml, 1.6M in hexane, 0.27 mol) dropwise at −78° C. within 45 min. The resulting beige-colored suspension was stirred for an additional 1 h at −78° C. Then PPh$_2$Cl (61 g, 0.277 mol, 49.7 ml) was added dropwise. The addition was complete within 2 h. The resulting yellow solution was allowed to warm to 0° C. within 2 h and quenched by addition of NH$_4$Cl solution (200 ml). The organic layer was separated, washed with brine (250 ml), dried (Na$_2$SO$_4$), filtered, and evaporated. The solid was recrystallized from methanol to give 69.5 g(80%) of 19.

Ref.: *Helvetica ChimicaActa* Vol. 74, 1991, 370–389

Synthesis of 3,4,5-trimethoxyphenyl)diphenylphosphine oxide 20

To a suspension of 19 (69.5 g, 0.2 mmol) in MeOH (500 ml) was added dropwise 30% H$_2$O$_2$ (24.5 g, 0.215 mol) at 0° C. The resulting clear solution was stirred at ambient temperature for 1 h. Then it was treated with sat. Na$_2$SO$_3$ solution (75 ml) and IN HCl solution (50 ml). The mixture was concentrated under reduced pressure to remove the MeOH. The solid residue was dissolved in CH$_2$Cl$_2$ (300 ml), washed with water (2×200 ml) and brine (200 ml), dried over Na$_2$SO$_4$, and evaporated. To the resulting white solid was added 300 ml hexane and the resulting suspension was stirred vigorously at room temperature. Filtration of the white solid powder gave 67.2 g (0.182 mol, 91%) of pure 20.

Ref: *Helvetica Chimica Acta* Vol. 74, 1991, 370–389

Synthesis of (2-iodo-3,4,5-trimethoxyphenyl) diphenylphosphine oxide 21

To a solution of (i-Pr)$_2$NH (31.88 ml, 23.02 g, 0.227 mol) in dry THF (200 ml)was added n-BuLi solution (125 ml, 1.6M in hexane, 0.2 mol) dropwise at −78° C. The addition was complete within 15 min. After stirred at 0° C. for 10 min, the LDA solution was re-cooled to −78° C. It was then added via cannula to a flask containing a solution of 20 (67.2 g, 0.182 mol) in dry THF (200 ml) over 20 min. During the addition, the mixture was turned reddish-brown, and eventually a beige suspension was formed. After the reaction mixture was stirred for an additional 15 min at −78° C., a solution of 12 (50.6 g, 0.2 mol) in THF (200 ml) was added dropwise. The addition was complete in 3 h. A reddish-brown viscous paste was formed at the end of the addition. Then, the cooling bath was removed, and the mixture was allowed to warm to 0° C. to form a clear red solution. The mixture was quenched by the addition of a Na$_2$S$_2$O$_3$ solution (12 g in 100 ml H$_2$O). The solution was concentrated to remove THF. The residue was dissolved in 300 ml of CH$_2$Cl$_2$, washed with water (2×200 ml) and brine (200 ml), dried over Na$_2$SO$_4$, and evaporated. The brown paste was recrystallized in EtOAc (100 ml) to give 55 g (62%) of 21.

Ref: *Helvetica Chimica Acta* Vol. 74, 1991, 370–389

Synthesis of (2-phenyl-3,4,5-trimethoxyphenyl) diphenylphosphine oxide 22

To a 2 liter Schlenk flask was added (2-iodo-3,4,5-trimethoxyphenyl) diphenylphosphine oxide 21 (30 g, 61 mmol), phenylboronic acid (11.1 g, 91 mmol), and degassed THF (800 ml). A solution of degassed saturated K$_2$CO$_3$ (400 ml) was added afterwards. The whole mixture was degassed with nitrogen for an additional 10 min. Then, Pd(PPh$_3$)$_4$ (1.22 mmol, 1.4 g) was added in the solution through one portion. The mixture was stirred at reflux under nitrogen for 24 hrs. In situ $^{31}$PNMR showed that the reaction was complete. The reaction mixture was concentrated under reduced pressure to remove THF and 400 ml of CH$_2$Cl$_2$ was then added. The CH$_2$Cl$_2$ layer was washed with water (200 ml) and brine (200 ml), dried over Na$_2$SO$_4$, and evaporated. The solid residue was recrystallized from EtOAc (100 ml) to give off-white product 22 (23 g). The mother liquid was passed through a silica gel column to give another 4 g of product 22. The total yield was 98%.

Synthesis of (2-iodo-6-phenyl-3,4,5-trimethoxyphenyl) diphenylphosphine oxide 23

To a solution of (2-phenyl-3,4,5-trimethoxyphenyl) diphenylphosphine oxide 22 (26.5 g, 59.7 mmol) in dry THF (500 ml) was added t-BuLi (47.7 ml, 1.5M in pentane, 71.6 mmol) dropwise at −90° C. The addition was complete within 2 hrs. The solution was allowed to warm to −78° C. and stirred for an additional 3 h. Then a solution of 12 in THF (100 ml) was added dropwise at this temperature. The addition was complete in 2 h. The resulting dark solution was allowed to warm to room temperature and stirred overnight. A solution of Na$_2$S$_2$O$_3$ (12 g in 100 ml H$_2$O) was added. The resulting yellow solution was concentrated under reduced pressure. To the residue was added 500 ml of CH$_2$Cl$_2$. The CH$_2$Cl$_2$ layer was washed with water (100 ml) and brine (100 ml), dried over Na$_2$SO$_4$, and evaporated. The residue was recrystallized from EtOAc (100 ml) to give a pure brown solid 23 (24 g). The mother liquid was passed through a silica gel column to give another 5 g of product. The total yield is 85%.

Synthesis of (RS)-(3,3'-diphenyl-4,4',5,5',6,6'-hexamethoxybiphenyl-2,2'-diyl)bis(diphenylphosphine oxide) 24

A mixture of (2-iodo-6-phenyl-3,4,5-trimethoxyphenyl) diphenylphosphine oxide 23 (7.4 g, 12.6 mmol), Cu powder (252 mmol, 16 g, activated by I$_2$ treatment), and DMF (200 ml) was stirred at 155° C. for 1 hr. The cold mixture was evaporated to dryness at the rotor evaporator at 70° C. The residue was treated for a few min with CH$_2$Cl$_2$ (200 ml). The solid was removed by filtration and washed with CH$_2$Cl$_2$ (200 ml). The combined filtrate was washed with sat. NH$_4$Cl solution (2×100 mL), dried over Na$_2$SO$_4$, and evaporated. The residue was crystallized from EtOAc (100 ml) to give 5 g (90%) of white product 24.

Resolution of (3,3'-diphenyl-4,4',5,5',6,6'-hexamethoxybiphenyl-2,2'-diyl)bis(diphenylphosphine oxide) 25

To a mixture of (RS)-(3,3'-diphenyl-4,4',5,5',6,6'-hexamethoxybiphenyl-2,2'-diyl)bis(diphenylphosphine oxide) 24 (2.3 g, 2.5 mmol) and (−)-DTTA (−0.966 g, 2.5 mmol) was added 40 ml of i-PrOH. The resulting slurry was heated to reflux to get a clear solution. Then it was cooled slowly to room temperature and stirred overnight. The salt of (−)-25 and (−)-DTTA was obtained as white powder through filtration(ee: 95%). The salt was recrystallized one more time from 25 ml i-PrOH and 1.1 g of solid was obtained. The solid was dissolved in 50 ml of CH$_2$Cl$_2$, washed with 3N NaOH (2×50 ml) and water (3×50 mL), dried over Na$_2$SO$_4$, and evaporated. The solid (97.7%, 0.86 g) was recrystallized from acetone to give enantiomerically pure product 25 (0.69 g, 60%, ee>99.5%). Synthesis of (−)-(3,3'-diphenyl-4,4',5, 5',6,6'-hexamethoxybiphenyl-2,2'-diyl)bis (diphenylphosphine) 26.

To a solution of (−)-(3,3'-diphenyl-4,4',5,5',6,6'-hexamethoxybiphenyl-2,2'-diyl)bis(diphenylphosphine oxide) 25 (700 mg, 0.79 mmol, resolved from (−)-DTTA), tributylamine (6.5 ml, 27.3 mmol), and xylene (100 ml) was added HSiCl$_3$ (1.72 ml, 17 mmol) dropwise at 0° C. The reaction was stirred at reflux for 2 days. Some precipitates came out during the course. After cooled down, the reaction mixture was quenched with 30% degassed NaOH solution (20 ml) in an ice-water bath. The resulting solution was kept at 60° C. for 1 h. The organic phase was transferred into another Schlenk flask through cannula. The water phase was re-washed with CH$_2$Cl$_2$ (30 ml*2). The combined organic phase was washed with water (50 ml), dried over Na$_2$SO$_4$, and evaporated under reduced pressure. The resulting yellow residue was dissolved in CH$_2$Cl$_2$ (10 ml) and passed through a basic Al$_2$O$_3$ column to give a pure white solid 26 (400 mg, 59%).

EXAMPLE 11

Synthesis of 2,2'-(diphenylphosphanyl)-3,6,3',6'-tetramethoxybiphenyl

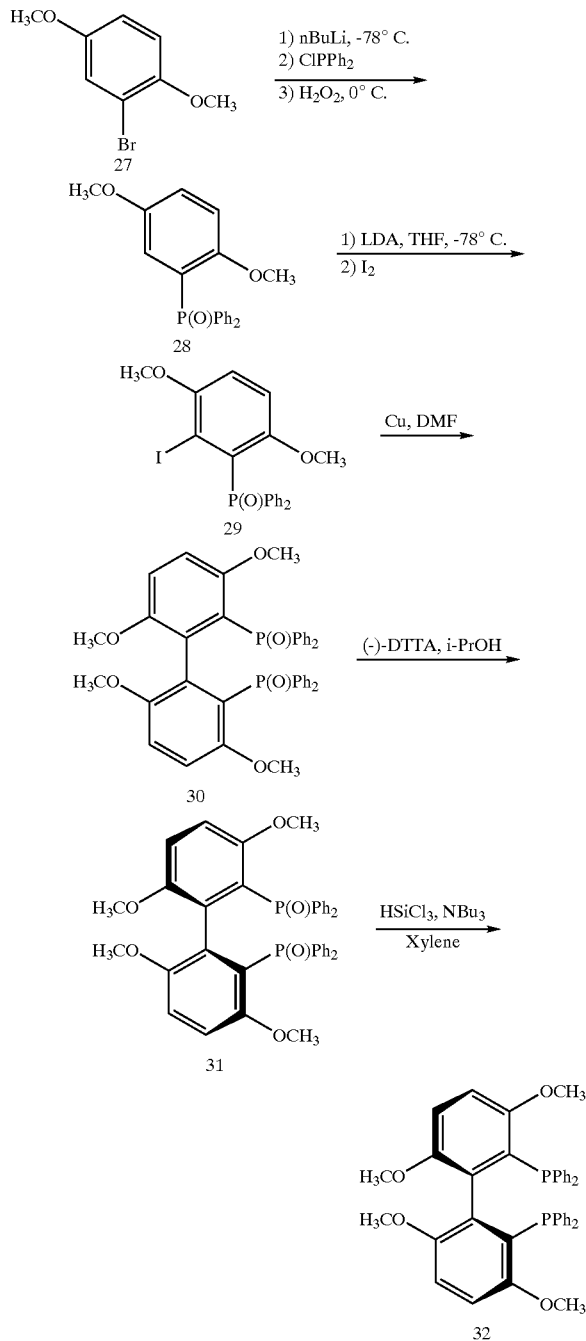

(2,5-Dimethoxyphenyl)diphenylphosphine Oxide

At −78° C., 2.5M n-BuLi in hexane (48 mL, 0.12 mol) was slowly added to a solution of 1-Bromo-2,5-dimethoxybenzene (27, 25 g, 0.115 mol) in THF (250 mL) causing the solution to become dark yellow (solid suspension). The reaction mixture was stir at this temp for about 30 minutes, following by addition of diphenylchlorophosphine (21.5 ml, 0.12 mol). During the addition, control the temp below −50° C. (add slowly). The resulting yellow solution was allowed to warm up to room temp (take about two hours). The saturated NH$_4$Cl solution (200 ml) was added and reaction mixture form two layers. The organic layer was washed with brine (2×100 mL) and dried (Na$_2$SO$_4$). The solvent was removed under vacuum to give a white solid.

Add MeOH (200 mL) to the resulting white solid to form suspension. At 0° C., 33% H$_2$O$_2$ (14 ml, 0.13 mol) was slowly added to above MeOH suspension. The addition process takes about 20 minutes and the solid vanished promptly after all H$_2$O$_2$ was added. The mixture was allowed to stir for one hour at 0° C., follow by adding saturated NaHSO$_3$ solution (15 ml) and stir for 30 minutes (the KI-Starch paper was applied here to make sure all peroxide was reduced). The solvent was removed under vacuum to give a white solid. The resulting solid was dissolved in CH$_2$Cl$_2$ (200 mL) and was washed with water (150 mL) and brine (150 mL), dried (Na$_2$SO$_4$). The solvent was also removed under vacuum to give a white solid. The crude product was treated with hot hexane (2×100 mL) (to remove trace amount of impurity) to give pure product (28, 37.3 g, 95.8%).

(3,6-Dimethoxy-2-iodophenyl)diphenylphosphine Oxide

A solution of LDA (6 mmol) 1.5M in pentane was slowly added to the phosphine oxide (28, 1.69 g, 5 mmol) in THF (60 mL) at 100° C. The resulting dark yellow solution (solid suspension) was allowed to warm up to −78° C. (take 30 minutes) and then stirred 3.5 hours at this temp. during which time the white solid precipitated. Solid I$_2$ (1.78 g, 7 mmol) was added against a counter flow of N$_2$ to the anion in THF at −78° C. The reaction was allowed to come to 0° C. and quenched with Na$_2$S$_2$O$_3$ aq. solution (10 mL). The solvent was removed under vacuum and the residue was extracted with CH$_2$Cl$_2$ (50 mL), washed with water (50 mL), brine (50 ml) and dried (Na$_2$SO$_4$). The solvent was removed and the brown oil residue was treated with EtOAc (10 mL) (to wash out most of the color impurities, the product form white solid in EtOAc). Then the vacuum filtration gives the white solid (29, 1.0 g, 43%)

2,2'-(Diphenylphosphinoyl)3,3',6,6'-tetramethoxybiphenyl

Copper powder (320 mg, 5 mmol) was added to a solution of the iodide (29, 116 mg, 0.25 mmol) in DMF (10 mL) and the reaction mixture heated to reflux for 8 hours. During the reflux, white solid formed along the wall of flask. The mixture was treated under vacuum to remove most of the solvent (before it cooled). The residue was extracted with CH$_2$Cl$_2$ (20 mL) and washed with water (2×10 mL), brine (10 mL) and dried (Na$_2$SO$_4$). The solvent was removed under vacuum and the resulting solid was washed with EtOAc (2 mL) to give a white solid (30, 70 mg, 83%).

Resolution of 2,2'-(diphenylphosphinoyl)3,3',6,6'-tetramethoxybiphenyl (−) DTTA (0.579 g, 1.5 mmol) was added to diphosphine oxide (30, 0.674 g, 1 mmol) in EtOH (29 mL) solution(at this time, DTTA can not dissolve in EtOH solution). The reaction mixture was heated up to reflux until all solid suspension was completely dissolved (take about 20 minutes). The resulting solution was allowed to stir overnight until crystal formed. The mixture was filtrated under vacuum and washed with cold EtOH (5 mL). The resulting solid (0.405 g, 75.1%) was added to $CH_2Cl_2$ (20 mL) and NaOH (20 mL, 10% aq.) solution for about 5 minutes, and the entire insoluble solid disappeared. The organic layer was washed with water (2×10 mL), brine (10 mL) and dried ($Na_2SO_4$). The solvent was removed under vacuum to give a white solid (31, 99.3% ee).

2,2'-Diphenylphosphanyl-3,6,3',6'-tetramethoxybiphenyl $HSiCl_3$ (542 mg, 0.4 mL) and $NBu_3$ (1.48 g, 1.9 mL) were added to diphosphine oxide (31, 70 mg, 0.1 mmol) in xylene (5 mL) solution under $N_2$ atmosphere. The reaction mixture was heated to reflux for 3 hours. The mixture was allowed to cool down to room temp. Then the degassed NaOH aq. solution (10%, 5 mL) was added to reaction mixture at 0° C. and stir for one hour. The organic layer was washed with degassed water (2×10 mL), $NH_4Cl$ aq. solution (10 mL), brine (10 mL) and dried ($Na_2SO_4$). The solvent was removed under vacuum to give a pale yellow solid. After a short plug (silica gel, elute with $CH_2Cl_2$:Hexane=1:1), the solvent was evaporated under vacuum to give a white solid (still not pure white, a little bit pale yellow color) (32, 50 mg, 75%).

EXAMPLE 12

Asymmetric Hydrogenation of Enamides Facilitated by Rh-Complexes with (−) (3,3'-diphenyl-4,4',5,5', 6,6'-hexamethoxybiphenyl-2,2'-diyl)bis-(diphenylphosphine) (26)

Rh-complexes with (−) (3,3'-diphenyl-4,4',5,5', 6,6'-hexamethoxybiphenyl-2,2'-diyl)bis(diphenylphosphine) (26) are good catalysts for hydrogenation of enamides. Introduction of 3,3' substituted groups have some effects on enantioselectivity of asymmetric hydrogenation of enamides. Cyclic enamides can be hydrogenated with good enantioselectivity.

Rh-Catalyzed Asymmetric Hydrogenation

The present invention has been described with particular reference to the preferred embodiments. It should be understood that the foregoing descriptions and examples are only illustrative of the invention. Various alternatives and modifications thereof can be devised by those skilled in the art without departing from the spirit and scope of the present invention. Accordingly, the present invention is intended to embrace all such alternatives, modifications, and variations that fall within the scope of the appended claims.

What is claimed is:

1. A ligand represented by the formula or its enantiomer:

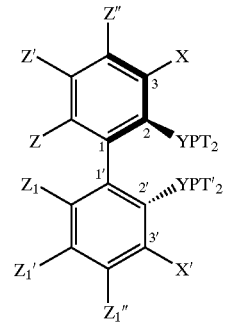

wherein each X and X' is independently selected from the group consisting of: alkyl, aryl, substituted alkyl, substituted aryl, OR, SR, $NR_2$, COOR, and halide;

wherein each Z and $Z_1$ is independently selected from the group consisting of: alkyl, aryl, substituted alkyl, substituted aryl, OR, SR, $NR_2$, COOR a d halide; or wherein Z and $Z_1$ together form the bridging group A-B-$A_1$;

wherein each Z', Z", $Z_1$' and $Z_1$" is independently selected from the group consisting of: H, alkyl, aryl, substituted alkyl, substituted aryl, OR, S, $NR_2$, COOR, and halide; or wherein Z' and Z together form the bridging group A'-B-A; Z' and Z together form a fused cycloaliphatic or aromatic group; $Z_1$ and $Z_1$' together form the bridging group $A_1$-$B_1$-$A_1$'; and/or $Z_1$ and $Z_1$' together form a fused cycloaliphatic or aromatic group;

wherein each A, A', $A_1$ and $A_1$' is independently selected from the group consisting of: O, $CH_2$, NH, NR, S, CO and a bond;

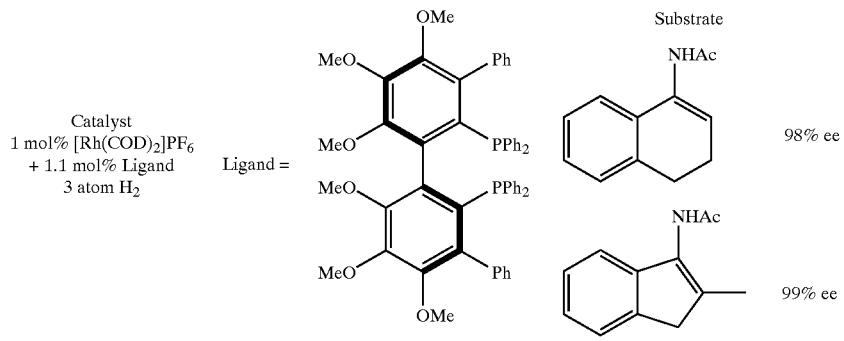

wherein each B and $B_1$ is independently selected from the group consisting of: O, $CH_2$, NH, NR, S, CO, $SO_2$, and a bond;

wherein each T is independently selected from the group consisting of: alkyl, substituted alkyl, aryl, substituted aryl, alkoxide, aryloxide, R, R', and R"; or wherein two T groups together form an alkylene or arylene;

wherein each T' is independently selected from the group consisting of: alkyl, substituted alkyl, aryl, substituted aryl, alkoxide, aryloxide, R, R', and R"; or wherein two T' groups together form an alkylene or arylene;

wherein each R, R'and R" is independently selected from th group consisting of: alkyl, substituted alkyl, aryl, aralkyl and alkaryl of 1 to 22 carbon toms; or wherein two R groups, two R' groups or two R" group together form an alkylene, arelene or substituted arylene group; and wherein each Y, Y' and Y" is independently selected from the group consisting of: $CH_2$ and a bond between carbon and phosphorus; with the proviso that when the Y group at the 2' position is a bond between carbon and phosphorus, X' is hydrogen.

2. The ligand of claim 1, wherein said substituted alkyl has one or more substituents, each independently selected from the group consisting of: halogen, ester, ketone, carboxylic acid, hydroxy, alkoxy, aryloxy, thiol, alkylthio and dialkylamino.

3. The ligand of claim 1, wherein said alkylene is selected from the group consisting of compounds represented by the formula: —$(CH_2)_n$—, wherein n is an integer in the range of from 1 to 8.

4. The ligand of claim 1, wherein each of said aryl groups optionally has one or more substituents, each independently selected from the group consisting of: halogen, ester, ketone, sulfonate, phosphonate, hydroxy, alkoxy, aryloxy, thiol, alkylthiol, nitro, amino, vinyl, substituted vinyl, carboxylic acid, sulfonic acid and phosphine.

5. The ligand of claim 1, wherein each of said arylene groups optionally has one or more substituents, each independently selected from the group consisting of: halogen, ester, ketone, sulfonate, phosphonate, hydroxy, alkoxy, aryloxy, thiol, alkylthiol, nitro, amino, vinyl, substituted vinyl, carboxylic acid, sulfonic acid and phosphine.

6. The ligand of claim 1, wherein each of said arylene groups is independently selected from the group consisting of: 1,2-divalent phenyl, 2,2'-divalent-1,1'-biphenyl, 2,2'-divalent-1,1'-binaphthyl and ferrocene.

7. The ligand of claim 1, wherein said ligand is a racemic mixture of enantiomers.

8. The ligand of claim 1, wherein said ligand is a non-racemic mixture of enantiomers.

9. The ligand of claim 1, wherein said ligand is one of the enantiomers.

10. The ligand of claim 1, having an optical purity of at least 85% ee.

11. The ligand of claim 1, having an optical purity of at least 95% ee.

12. The ligand of claim 1, wherein said ligand is selected from the group consisting of compounds represented by the following formulas:

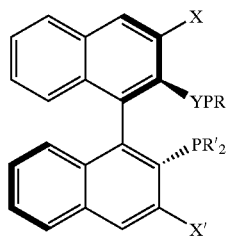
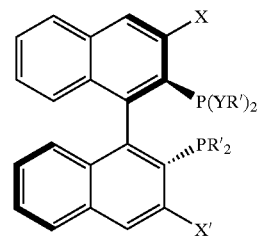
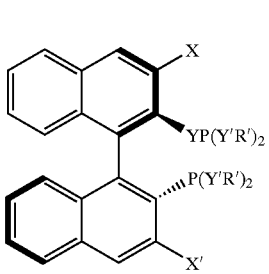
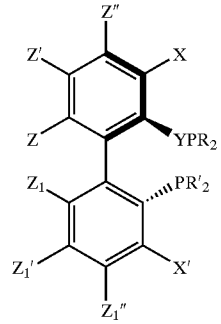
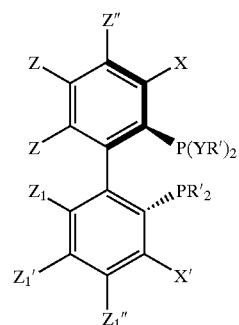
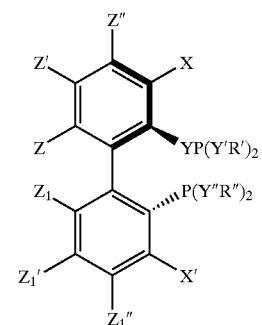
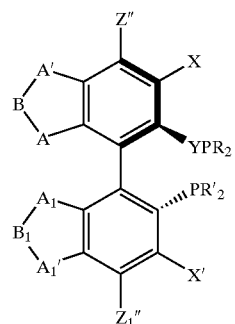
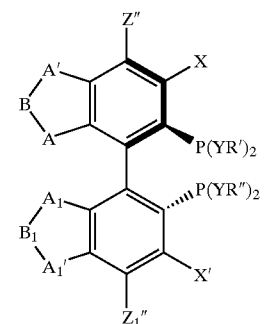
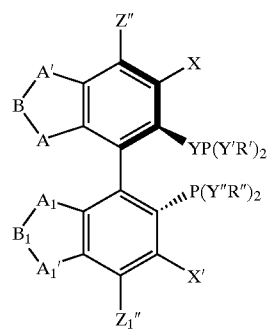
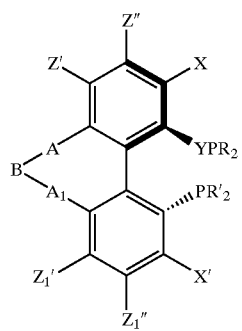

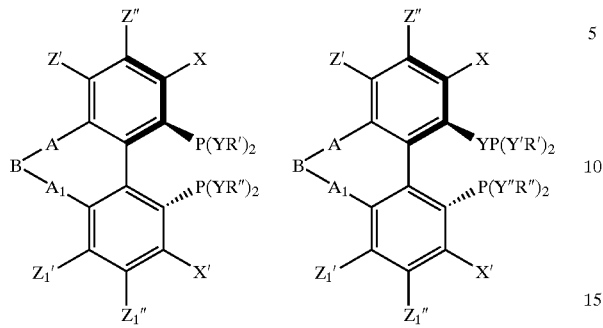

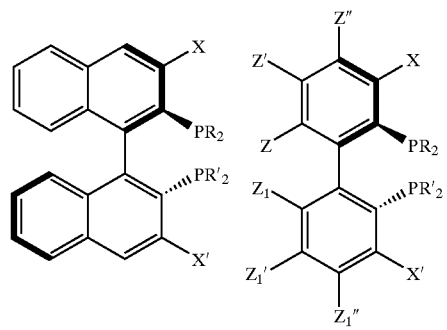

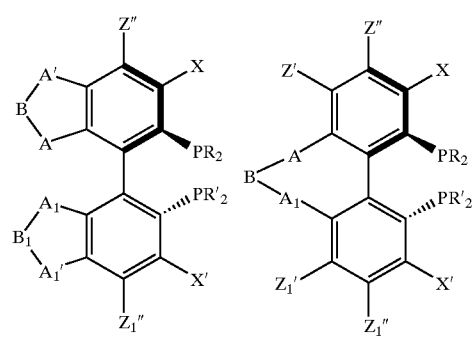

wherein each X and X' is independently selected from the group consisting of: alkyl, aryl, substituted alkyl, substituted aryl, OR, SR, $NR_2$, COOR, and halide;

wherein each Z and $Z_1$ is independently selected from the group consisting of: alkyl, aryl, substituted alkyl, substituted aryl, OR, SR, $NR_2$, COOR, and halide; or wherein Z and $Z_1$ together form the bridging group A-B-$A_1$;

wherein each Z', Z", $Z_1$' and $Z_1$" is independently selected from the group consisting of: H, alkyl, aryl, substituted alkyl, substituted aryl, OR, S, $NR_2$, COOR, and halide; or wherein Z' and Z together form the bridging group A'-B-A; Z' and Z together form a fused cycloaliphatic or aromatic group; $Z_1$ and $Z_1$' together form the bridging group $A_1$-$B_1$-$A_1$'; and/or $Z_1$ and $Z_1$' together form a fused cycloaliphatic or aromatic group;

wherein each A, A', $A_1$ and $A_1$' is independently selected from the group consisting of: O, $OH_2$, NH, NR, S, CO and a bond;

wherein each B and $B_1$ is independently selected from the group consisting of: O, $CH_2$, NH, NR, S, C0, $SO_2$, and a bond;

wherein each YR', YR", Y'R' and Y"R" is independently selected from the group consisting of: alkyl, substituted alkyl, aryl, substituted aryl, alkoxide and aryloxide; or wherein two YR', YR", Y'R' or Y"R" groups together form an alkylen, arylene, alkylenediamino, arylenediamino, alkelenedioxyl or arylenedioxyl;

wherein each R, R' and R" is independently selected from the group consisting of: alkyl, substituted alkyl, aryl, aralkyl and alkaryl of 1 to 22 carbon toms; or wherein two R groups, two R' groups or two R" group together form an alkylene or arelene group; and wherein each Y, Y' and Y" is independently selected from the group consisting of: $CH_2$, and a bond between carbon and phosphorus; with the proviso that when the Y group at the 2' position is a bond between carbon and phosphorus, X' is hydrogen.

13. The ligand of claim 1, wherein said ligand is selected from the group consisting of compounds represented by the following formulas:

wherein each X is independently selected from the group consisting of: alkyl, aryl, substituted alkyl, substituted aryl, OR, SR, $NR_2$, COOR, and halide;

wherein each X' is independently selected from the group consisting of: hydrogen, alkyl, aryl, substituted alkyl, substituted aryl, OR, SR, $NR_2$, COOR, and halide;

wherein each Z and $Z_1$ is independently selected from the group consisting of: alkyl, aryl, substituted alkyl, substituted aryl, OR, SR, $NR_2$, COOR, and halide;

wherein each Z', Z", $Z_1$' and $Z_1$" is independently selected from the group consisting of: H, alkyl, aryl, substituted alkyl, substituted aryl, OR, S, $NR_2$, COOR, and halide;

wherein each A, A', $A_1$ and $A_1$' is independently selected from the group consisting of: O, $CH_2$, NH, NR, S, CO and a bond;

wherein each B and $B_1$ is independently selected from the group consisting of: O, $CH_2$, NH, NR, S, C0, $SO_2$, and a bond;

wherein each R and R' is independently selected from the group consisting of: alkyl, substituted alkyl, aryl, substituted aryl, aralkyl and alkaryl of 1 to 22 carbon atoms, alkoxide and aryloxide; or wherein two R groups or two R' groups together form an alkylene, or arelene groups.

14. The ligand of claim 1, wherein said ligand is selected from the group consisting of compounds represented by the formulas:

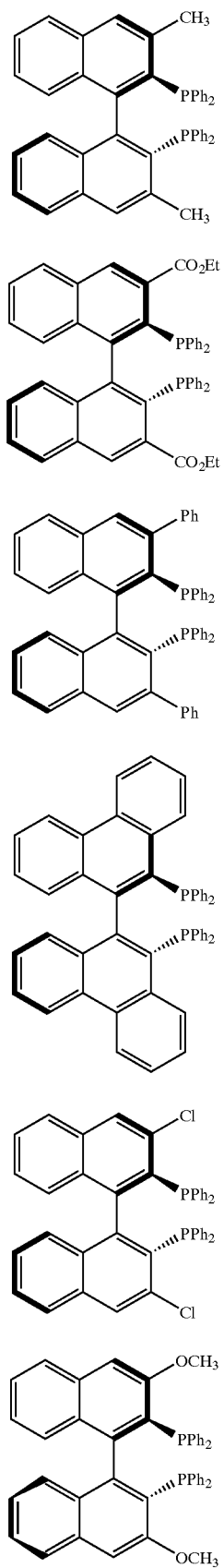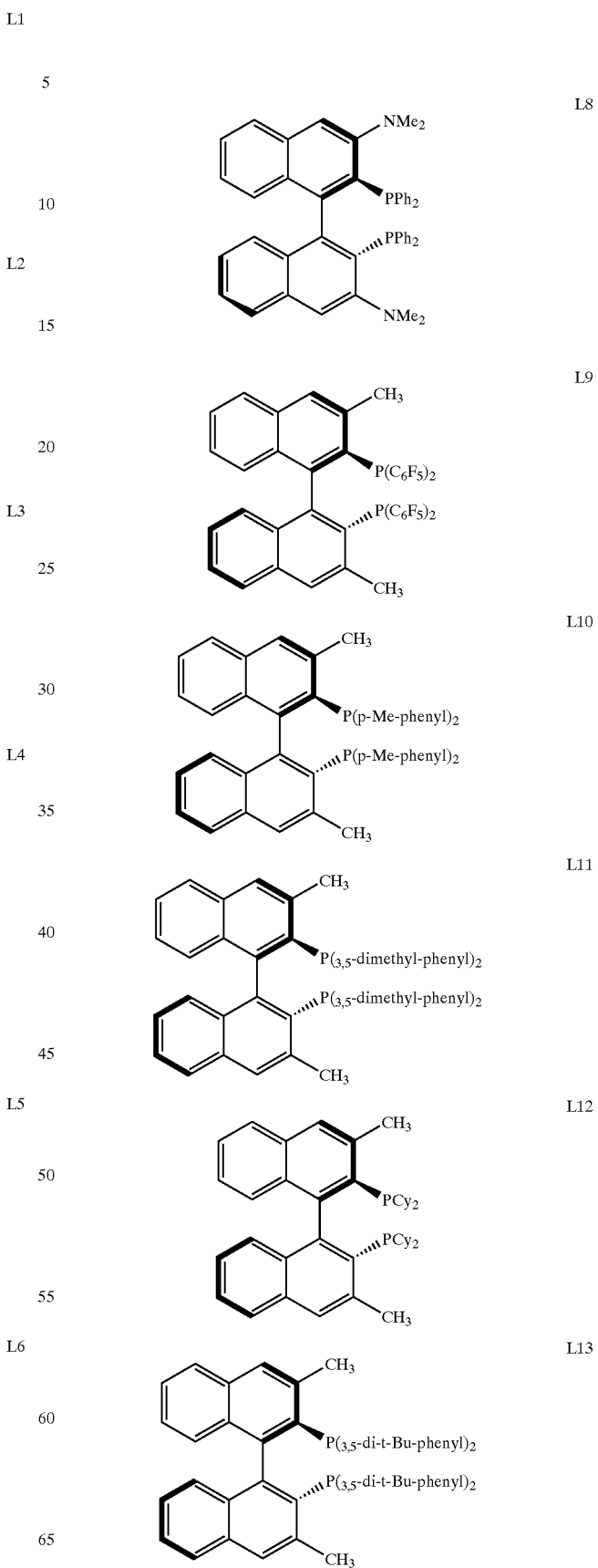

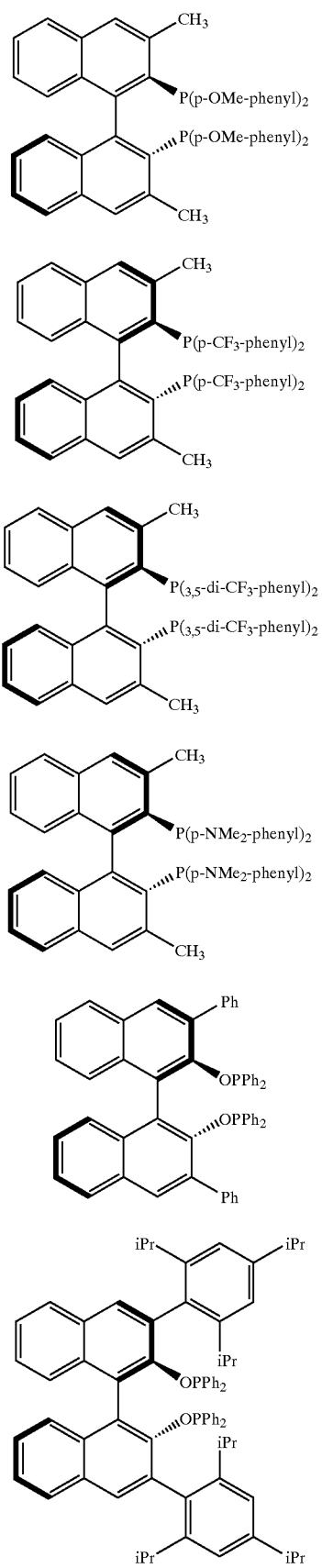

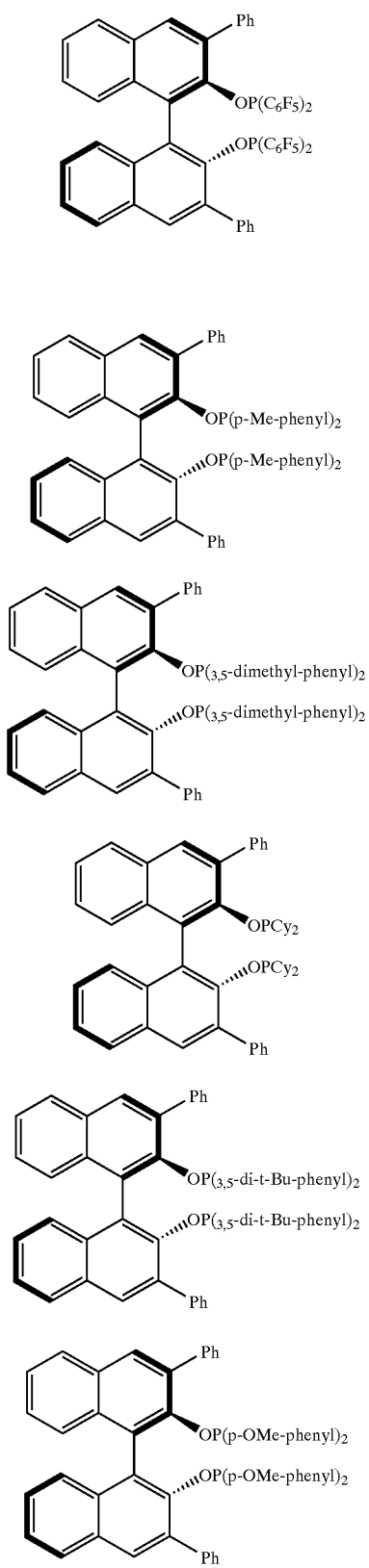
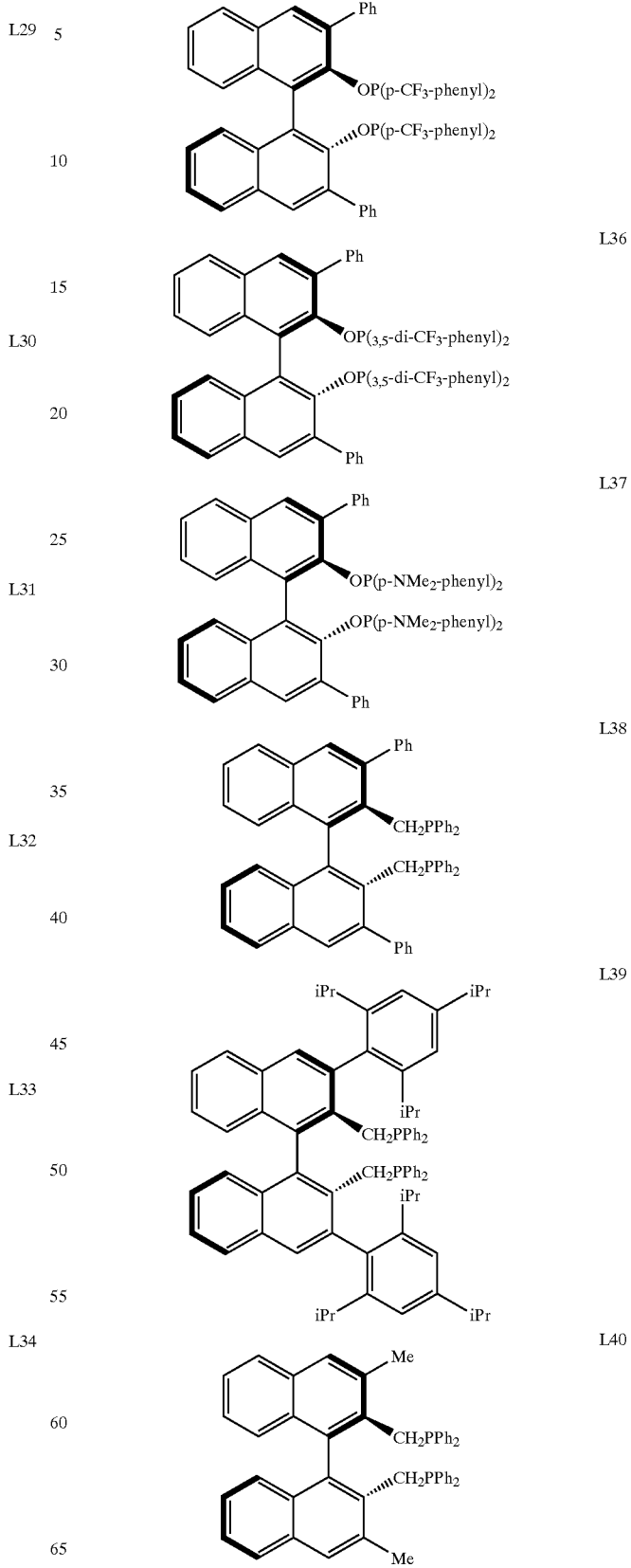

-continued
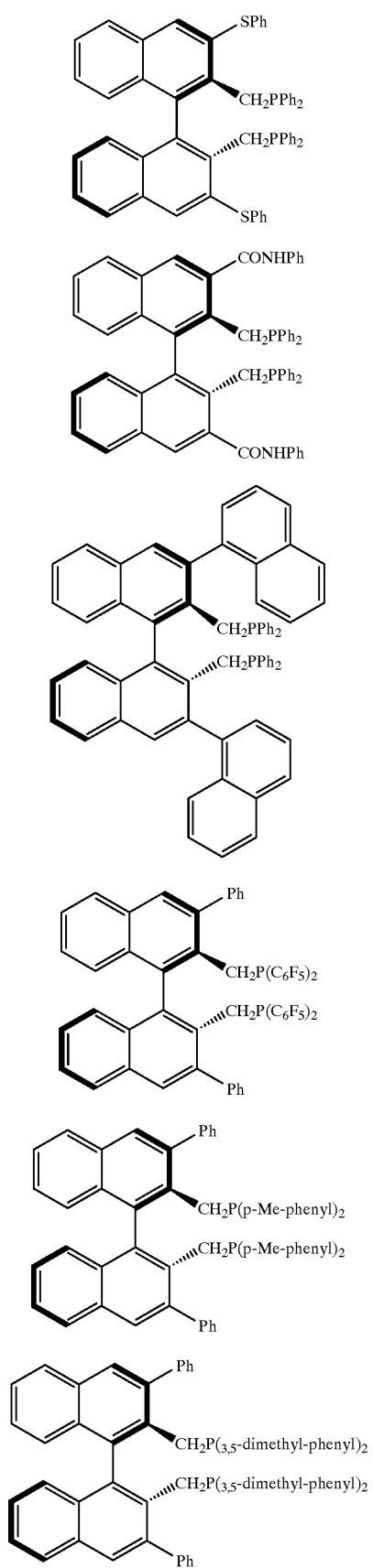
L41
L42
L45
L46
L47
L48
-continued
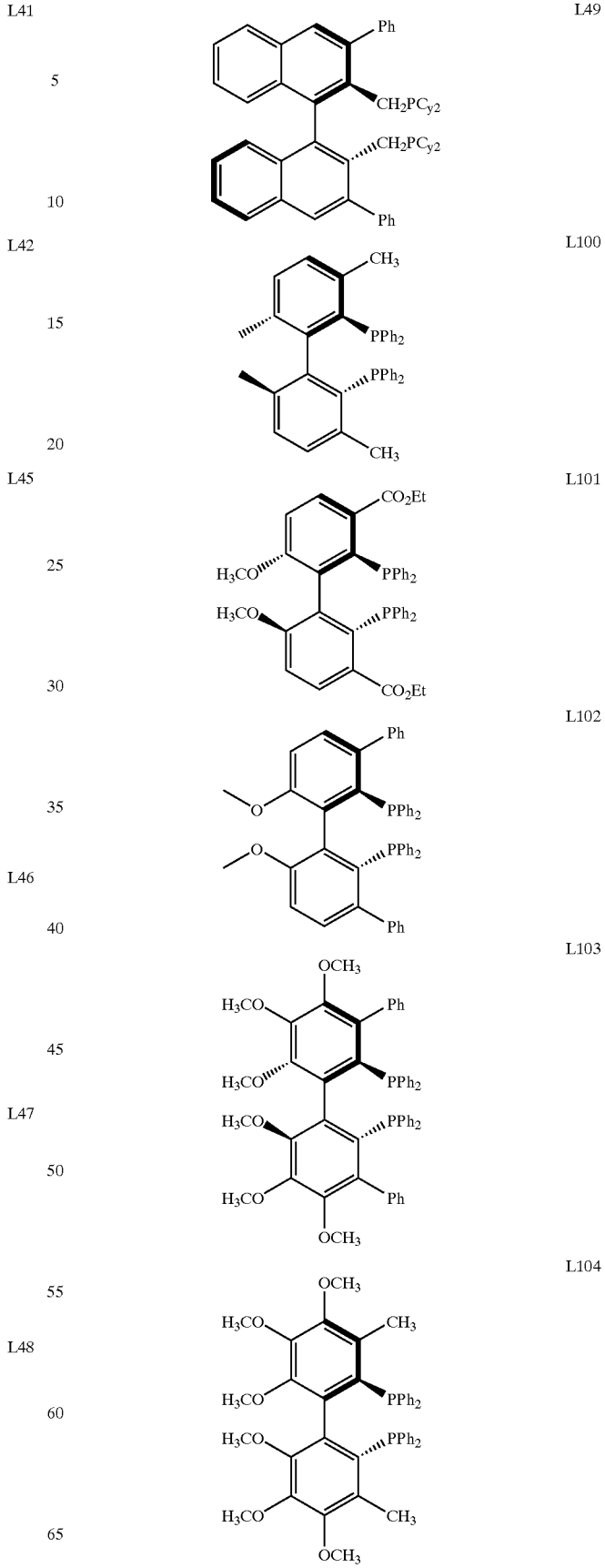
L49
L100
L101
L102
L103
L104

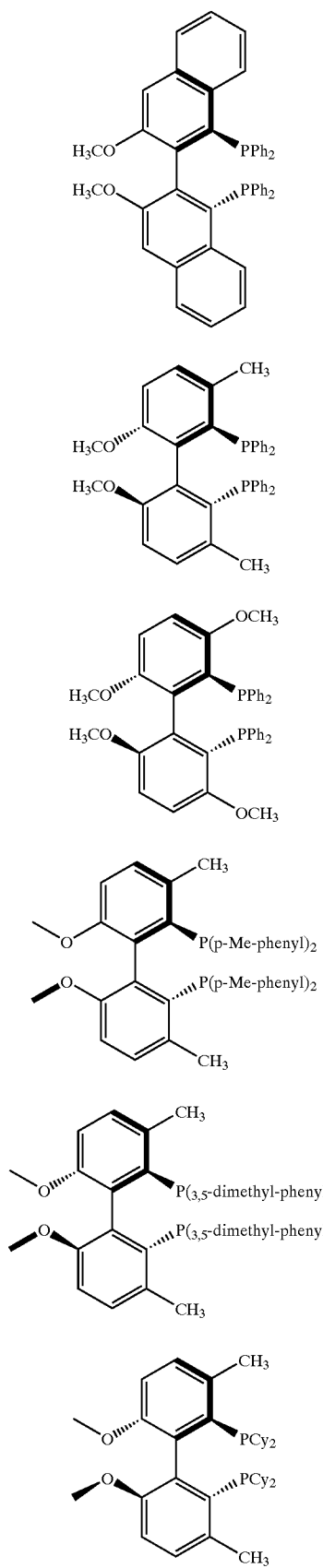
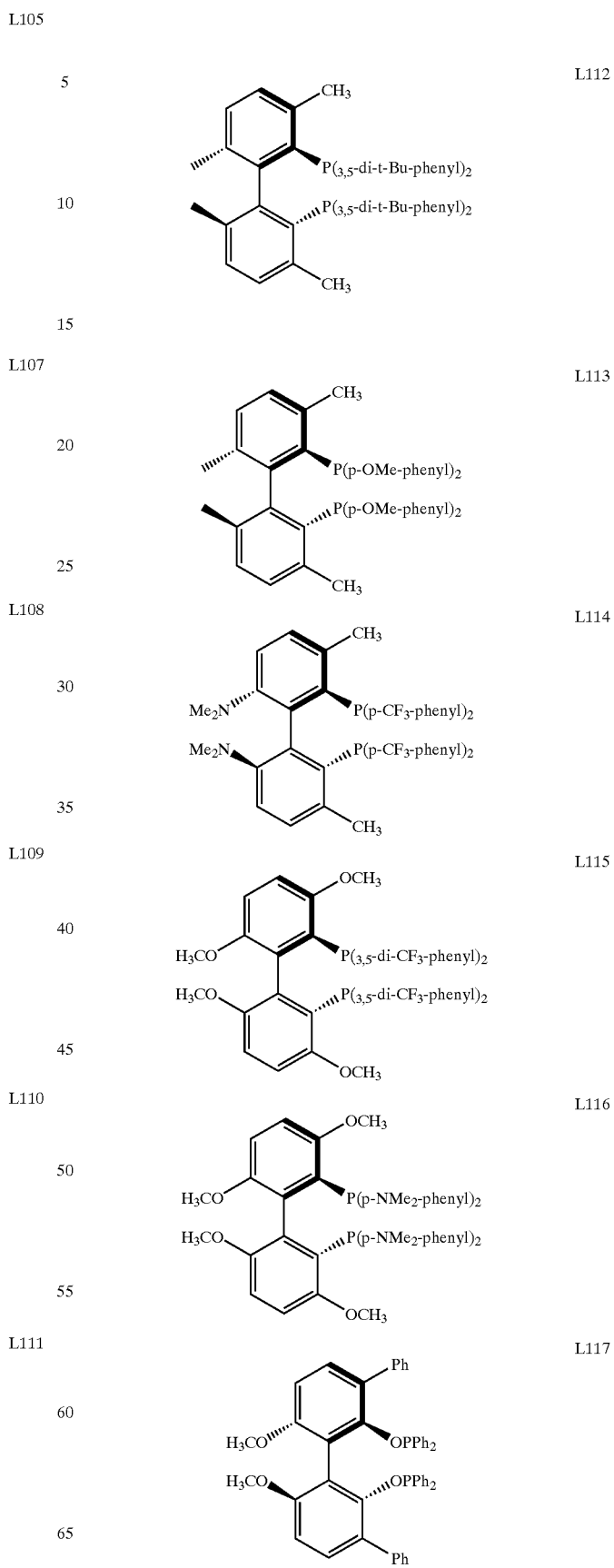

-continued
L118 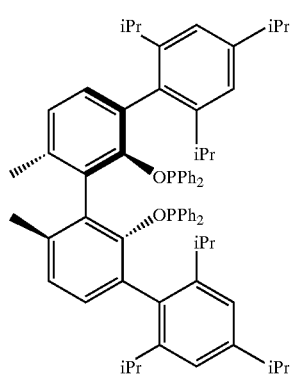
L119 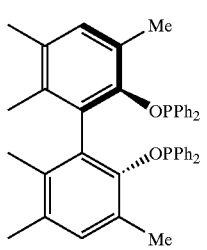
L120 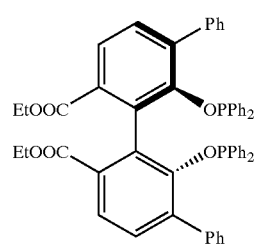
L121 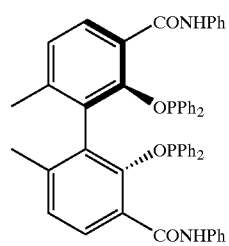
L122 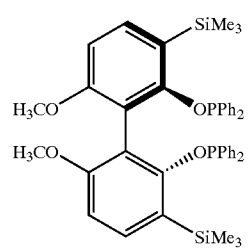
L123 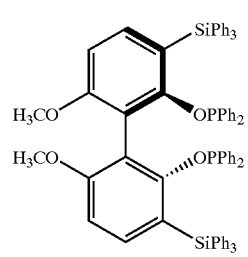
-continued
L124 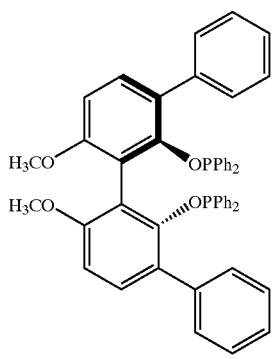
L125 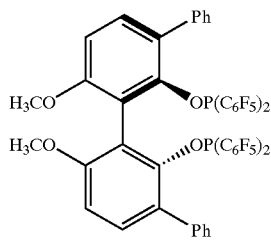
L126 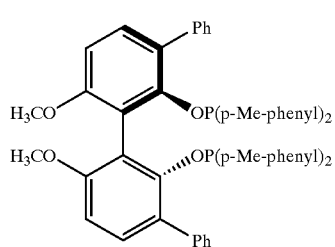
L127 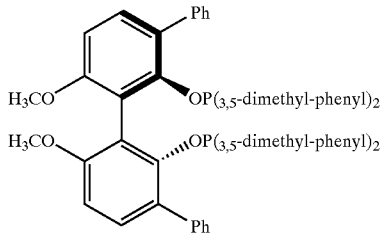
L128 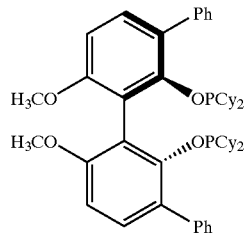
L129 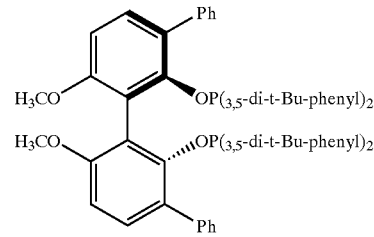

-continued
L130
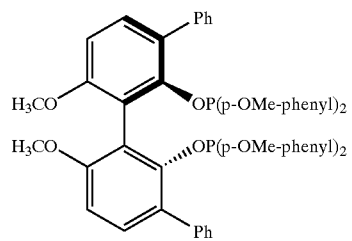
L131
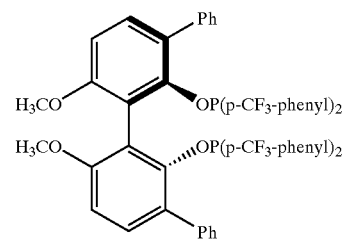
L132
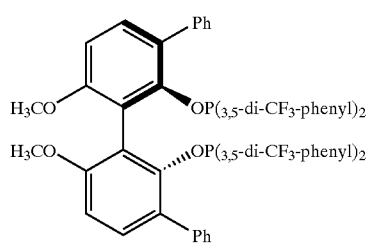
L133
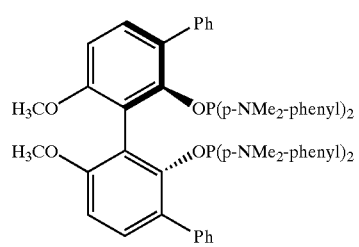
L134
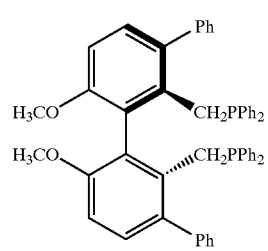
L135
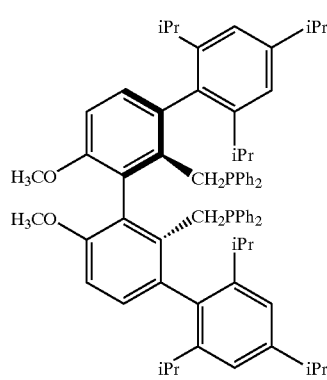
-continued
L136
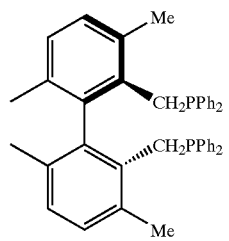
L137
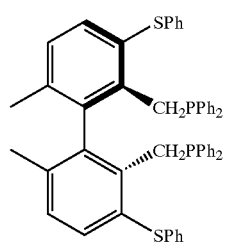
L138
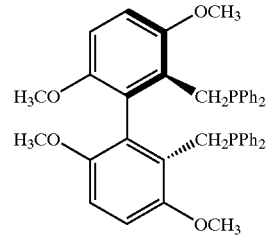
L141
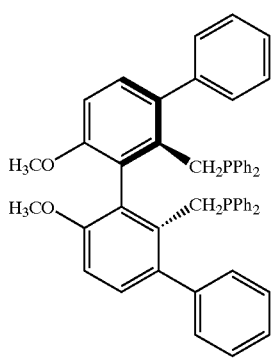
L142
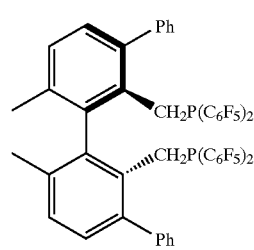
L143
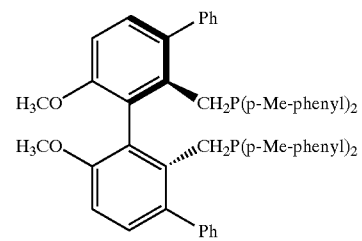

L144
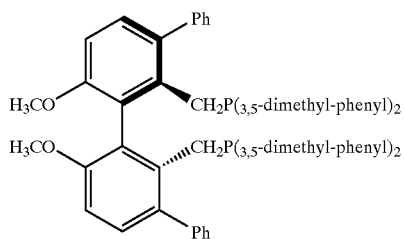
L145
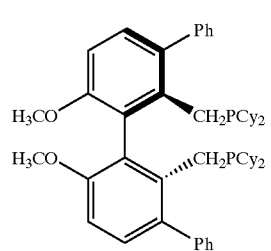
L146
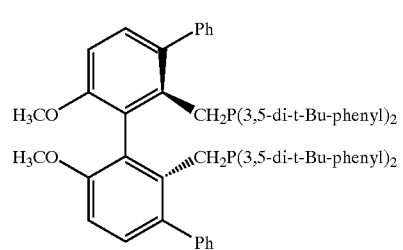
L147
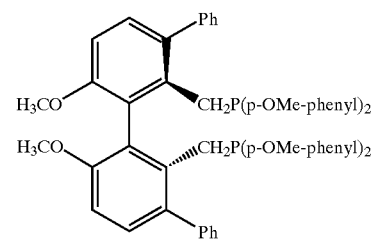
L148
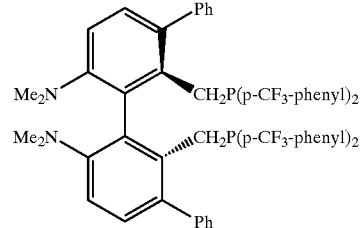
L149
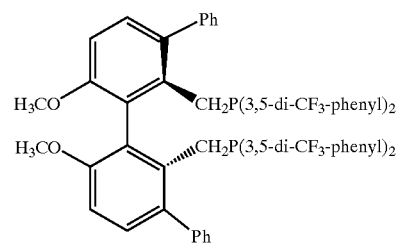
L150
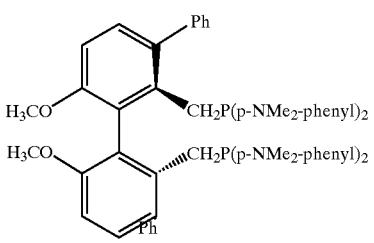
L196
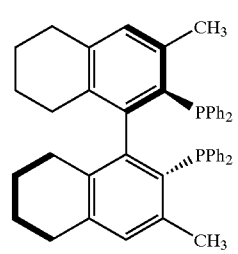
L197
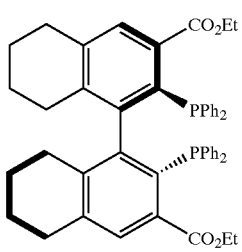
L198
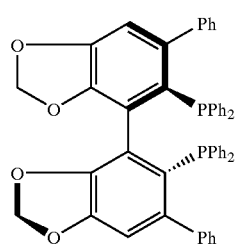
L199
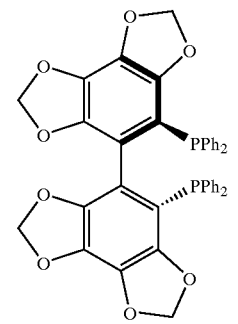
L200
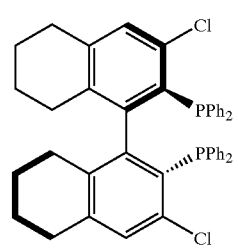

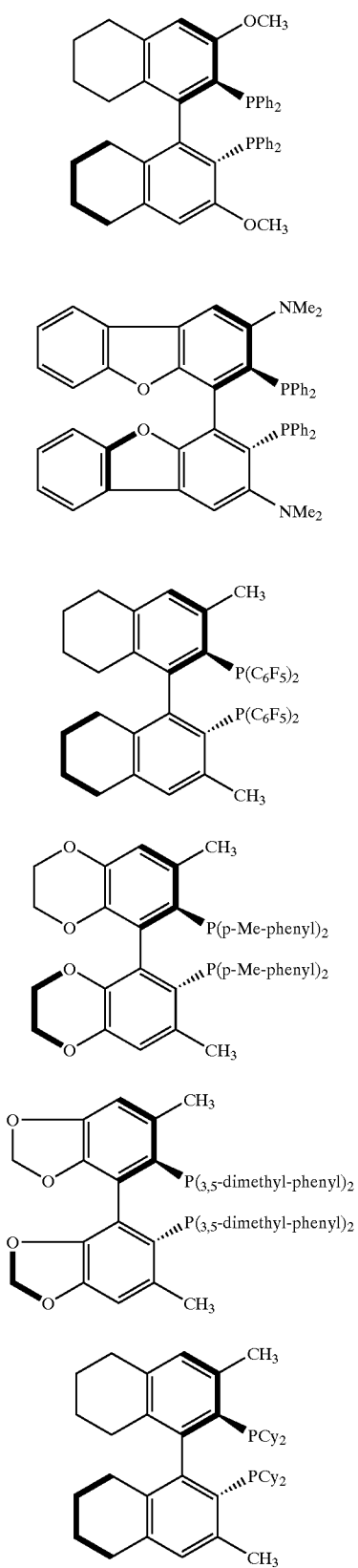
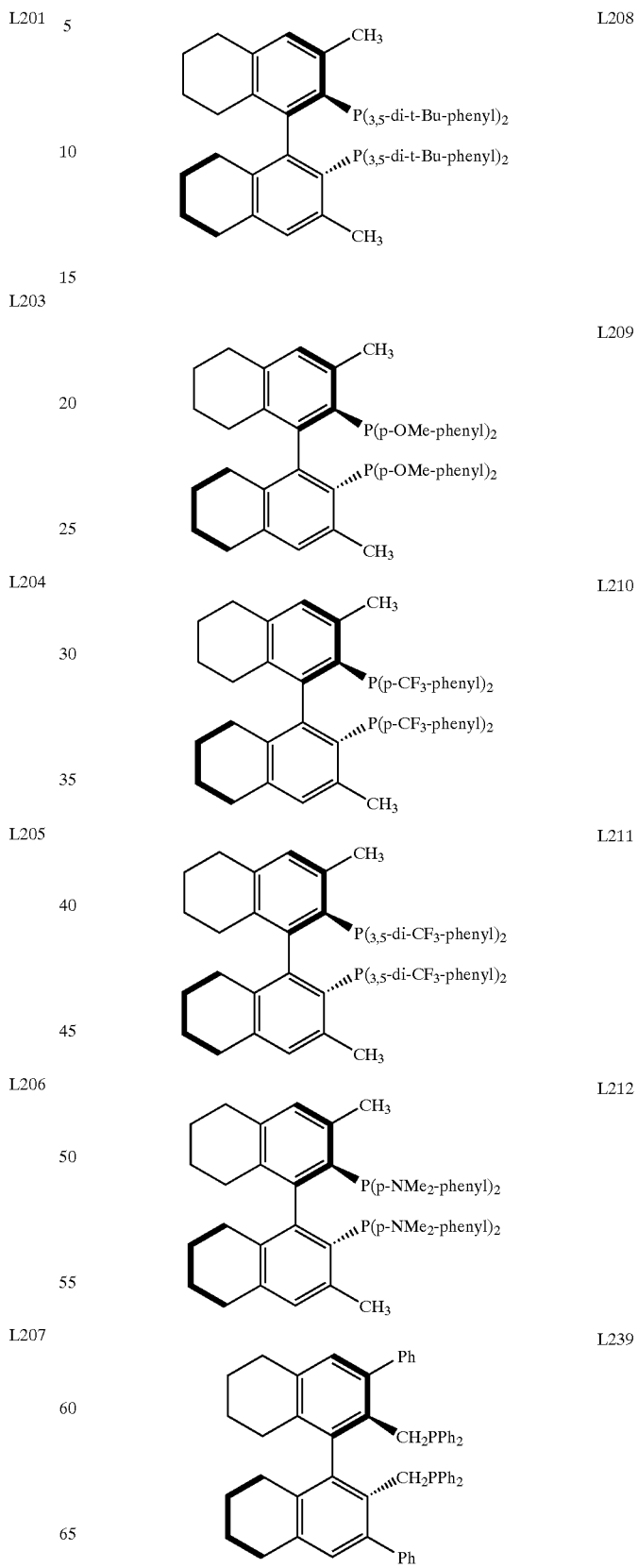

-continued
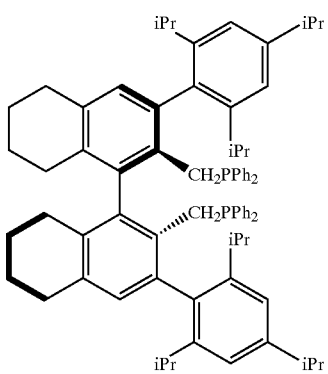
L240
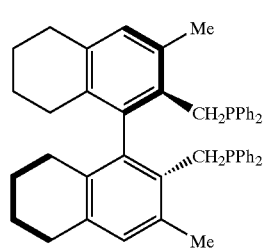
L241
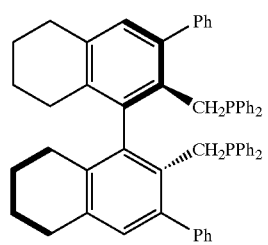
L242
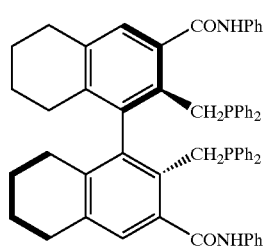
L243
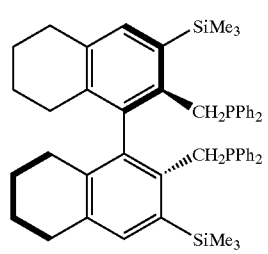
L244
-continued
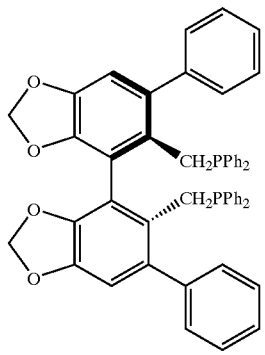
L246
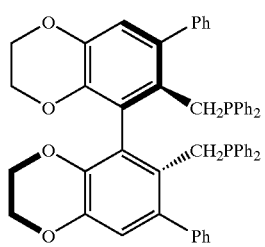
L247
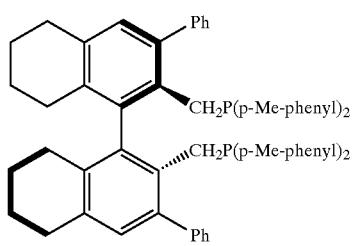
L248
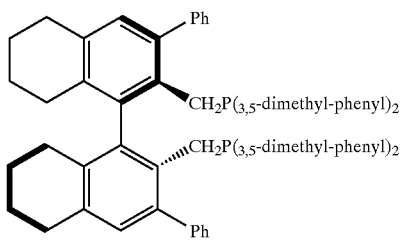
L249
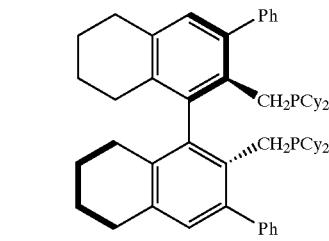
L250
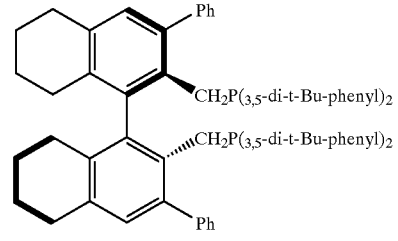
L251

-continued
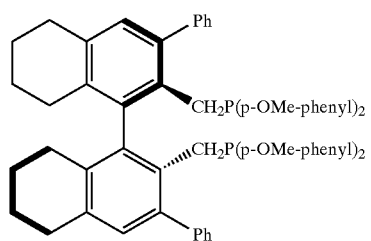 L252
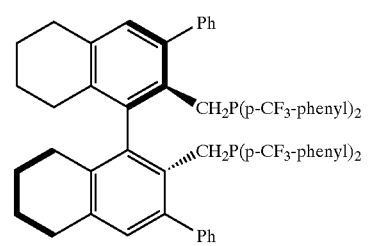 L253
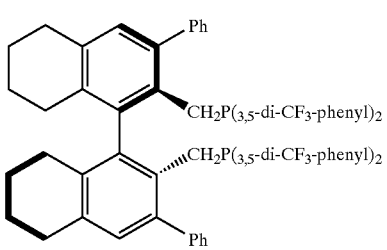 L254
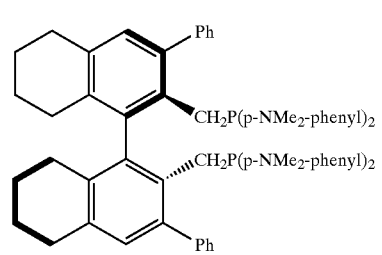 L255
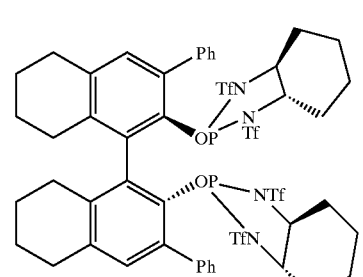 L300
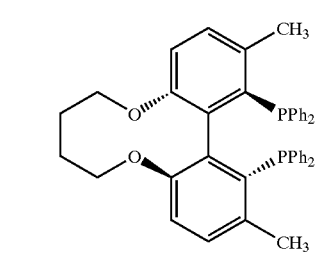 L301
-continued
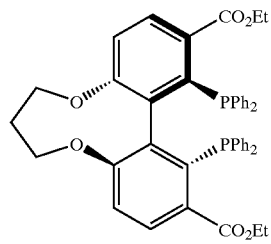 L302
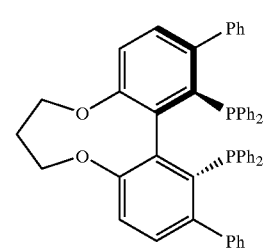 L303
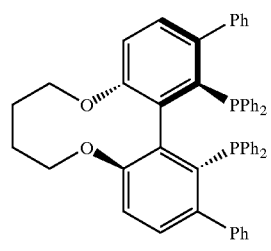 L304
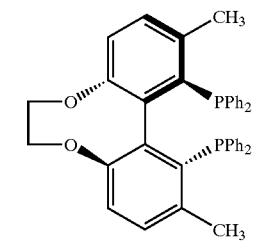 L305
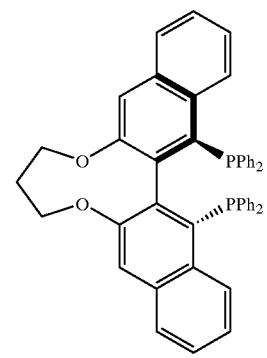 L306
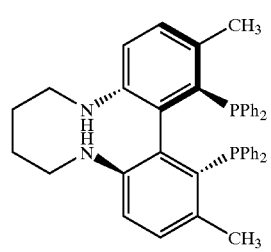 L308

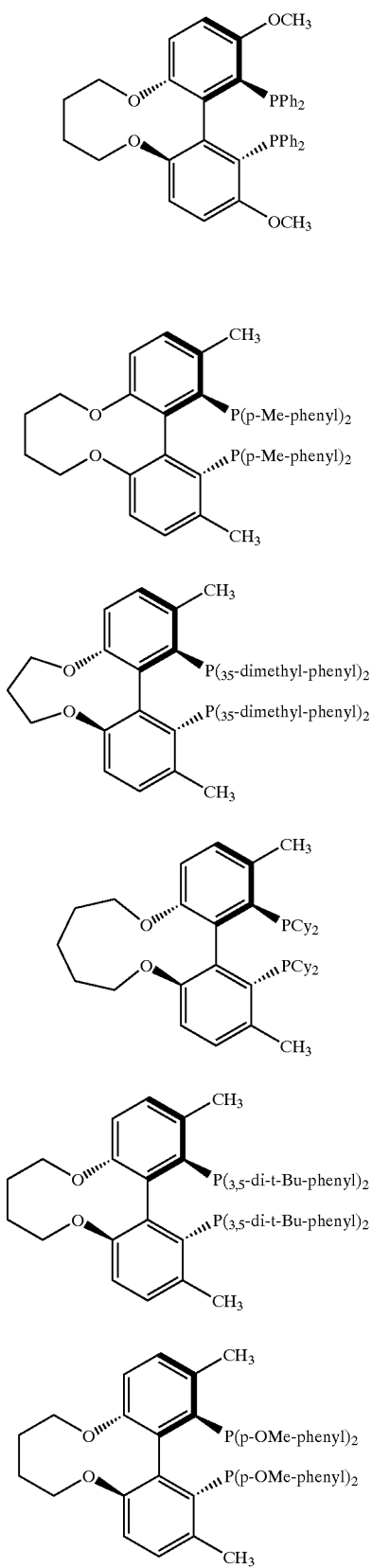
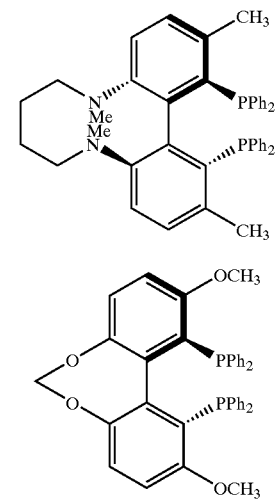

-continued
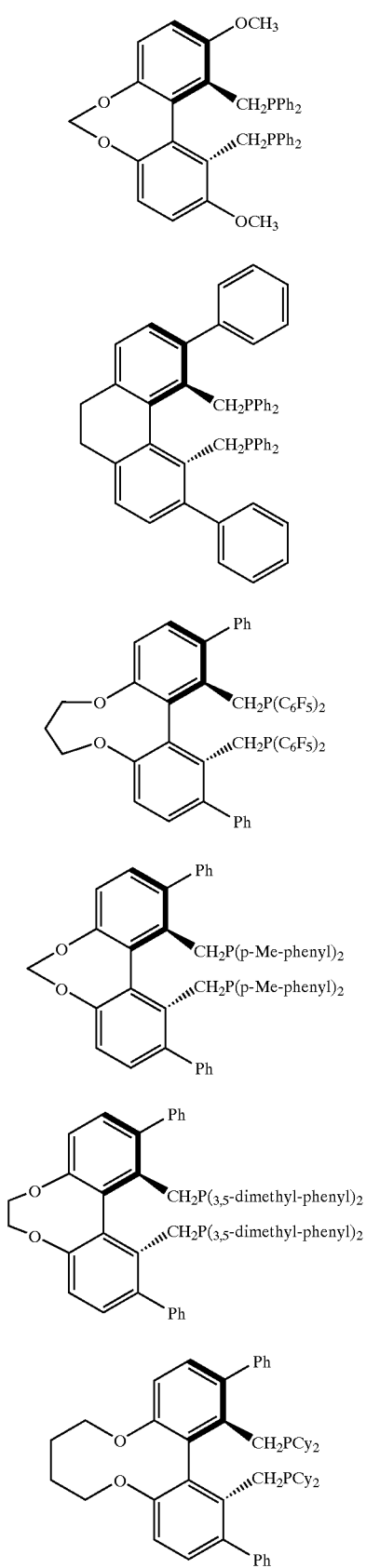
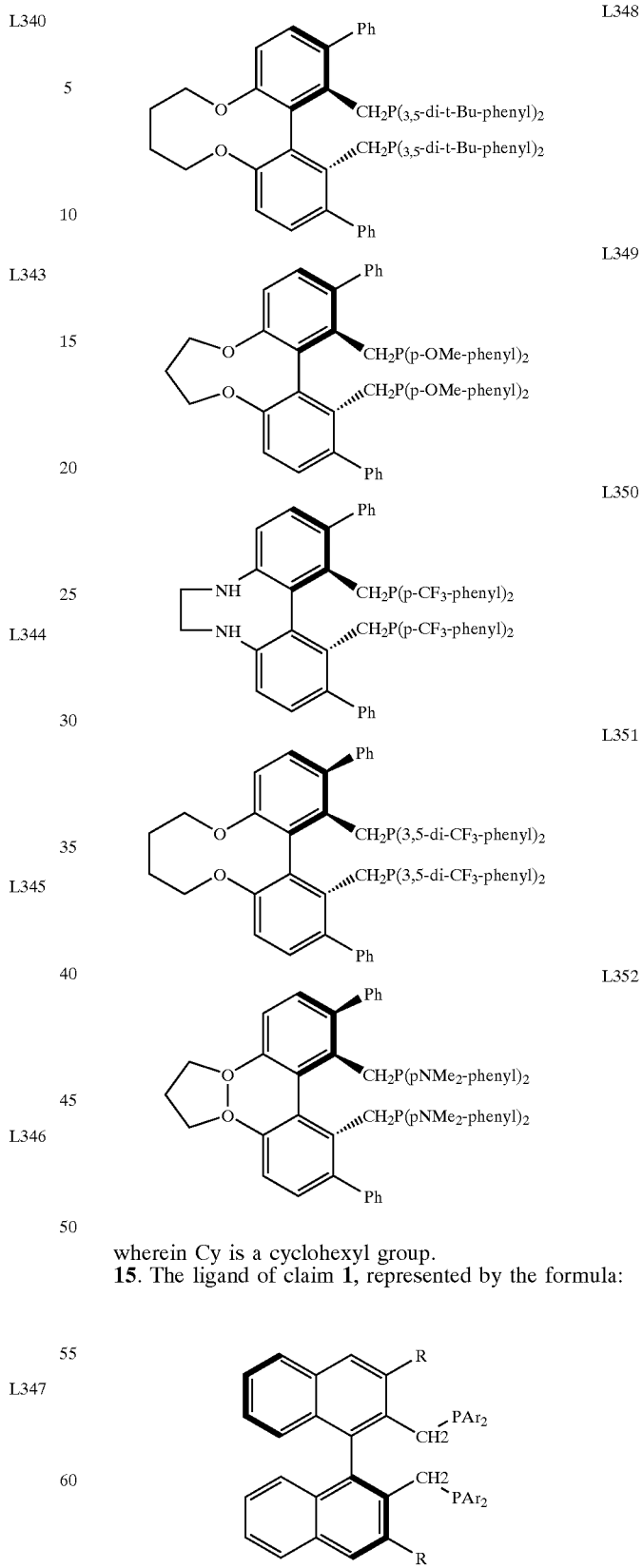
wherein Cy is a cyclohexyl group.
15. The ligand of claim 1, represented by the formula:
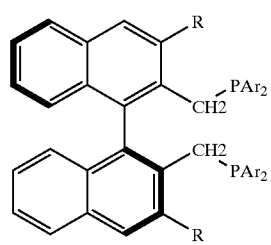
wherein each R is independently selected from the group consisting of: alkyl, aryl, substituted alkyl, and substituted aryl; and wherein each Ar is idependently selected from the group consisting of: phenyl, substituted phenyl, aryl and substituted aryl.
16. The ligand of claim 1, represented by the formula:
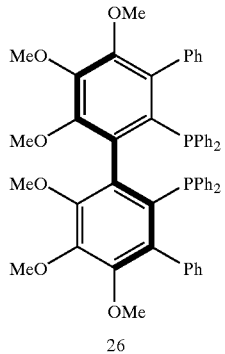
26
17. The ligand of claim 1, represented by the formula:
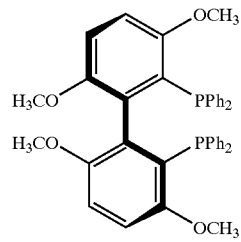
32
* * * * *

UNITED STATES PATENT AND TRADEMARK OFFICE
CERTIFICATE OF CORRECTION

PATENT NO. : 6,653,485 B2
DATED : November 25, 2003
INVENTOR(S) : Xumu Zhang

It is certified that error appears in the above-identified patent and that said Letters Patent is hereby corrected as shown below:

Column 112,
Line 34, "a d" should read -- and --.
Line 39, "S" should read -- SR --.

Column 113,
Line 16, "toms" should read -- atoms --.

Column 114,
Third column, first Ligand structure,

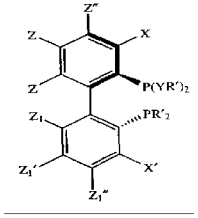

The upper "Z" in top ring should read -- Z' -- (Z prime) as follows:

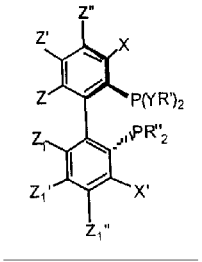

Column 115,
Line 31, "S" should read -- SR --.
Line 42, "C0" should read -- CO --.
Line 50, "alkylen" should read -- alkylene --.
Line 55, "toms" should read -- atoms --.

Column 116,
Line 47, "S" should read -- SR --.
Line 54, "C0" should read -- CO --.

UNITED STATES PATENT AND TRADEMARK OFFICE
CERTIFICATE OF CORRECTION

PATENT NO. : 6,653,485 B2
DATED : November 25, 2003
INVENTOR(S) : Xumu Zhang

It is certified that error appears in the above-identified patent and that said Letters Patent is hereby corrected as shown below:

Column 119,
Ligand structure L18 should be deleted.
Ligand structure L19 should be deleted.

Column 120,
Ligand structures, L20 to L26 should be deleted.

Column 121,
Ligand structures L29 to L34 should be deleted.

Column 122,
Ligand structures L35 to L37 should be deleted.

Column 124,
After Ligand structure L49, Ligand structures L51 to L54 should be added.

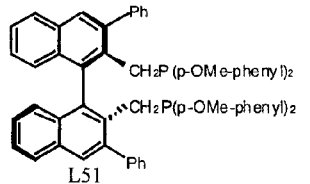
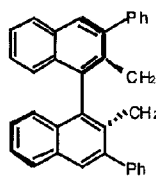
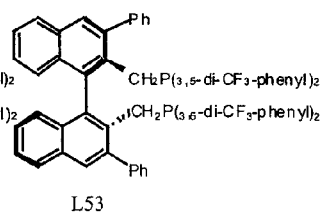
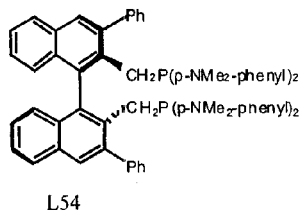

Column 126,
Ligand structure L117 should be deleted.

Column 127,
Ligand structure L118 to L123 should be deleted.

UNITED STATES PATENT AND TRADEMARK OFFICE
CERTIFICATE OF CORRECTION

PATENT NO. : 6,653,485 B2
DATED : November 25, 2003
INVENTOR(S) : Xumu Zhang

It is certified that error appears in the above-identified patent and that said Letters Patent is hereby corrected as shown below:

Column 128,
Ligand structures L124 to L129 should be deleted.

Column 129,
Ligand structures L130 to L133 should be deleted.

Column 132,
Ligand structure L150,

the bottom "Ph" should be moved and connected to the bottom ring with a bond -Ph as follows:

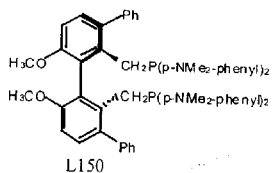

Column 137,
Ligand structure L300 should be deleted.

Column 142,
Ligand structure L352,

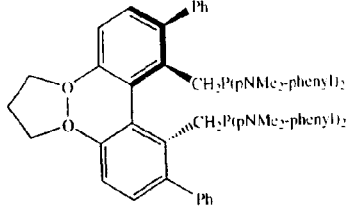

UNITED STATES PATENT AND TRADEMARK OFFICE
CERTIFICATE OF CORRECTION

PATENT NO. : 6,653,485 B2
DATED : November 25, 2003
INVENTOR(S) : Xumu Zhang

It is certified that error appears in the above-identified patent and that said Letters Patent is hereby corrected as shown below:

Column 142, cont'd,
should have the bond connecting O's deleted as follows:

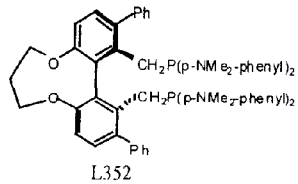

Signed and Sealed this

Ninth Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,653,485 B2
DATED : November 25, 2003
INVENTOR(S) : Xumu Zhang

It is certified that error appears in the above-identified patent and that said Letters Patent is hereby corrected as shown below:

Column 1,
Line 10, after "Jun. 27, 2001" please add the following heading and paragraph:
-- FEDERALLY SPONSORED RESEARCH AND DEVELOPMENT This invention was made with support from the Government under Grant No. 1R01-GM58832. The Government has certain rights in the invention. --

Signed and Sealed this

Eighth Day of June, 2004

JON W. DUDAS
*Acting Director of the United States Patent and Trademark Office*